(12) United States Patent
Bonny

(10) Patent No.: US 9,180,159 B2
(45) Date of Patent: Nov. 10, 2015

(54) USE OF CELL-PERMEABLE PEPTIDE INHIBITORS OF THE JNK SIGNAL TRANSDUCTION PATHWAY FOR THE TREATMENT OF CHRONIC OR NON-CHRONIC INFLAMMATORY DIGESTIVE DISEASES

(75) Inventor: Christophe Bonny, Lausanne (CH)

(73) Assignee: Xigen Inflammation Ltd., Limassol (CY)

( * ) Notice: Subject to any disclaimer, the term of this patent is extended or adjusted under 35 U.S.C. 154(b) by 614 days.

(21) Appl. No.: 12/995,197

(22) PCT Filed: Jun. 2, 2009

(86) PCT No.: PCT/EP2009/003936
§ 371 (c)(1),
(2), (4) Date: Apr. 15, 2011

(87) PCT Pub. No.: WO2009/144038
PCT Pub. Date: Dec. 3, 2009

(65) Prior Publication Data
US 2011/0207677 A1 Aug. 25, 2011

(30) Foreign Application Priority Data
May 30, 2008 (WO) ................. PCT/EP2008/004340

(51) Int. Cl.
*A61K 38/08* (2006.01)
(52) U.S. Cl.
CPC ..................................... *A61K 38/08* (2013.01)
(58) Field of Classification Search
None
See application file for complete search history.

(56) References Cited

U.S. PATENT DOCUMENTS

| | | | |
|---|---|---|---|
| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,630,351 B1 | 10/2003 | Monahan et al. |
| 6,653,443 B2 | 11/2003 | Zhang et al. |
| 6,673,908 B1 | 1/2004 | Stanton, Jr. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,034,109 B2 | 4/2006 | Bonny |
| 7,148,215 B2 | 12/2006 | Ratcliffe et al. |
| 7,166,692 B2 | 1/2007 | Karas |
| 7,635,681 B2 | 12/2009 | Bonny |
| 7,943,574 B2 | 5/2011 | Bonny |
| 8,236,924 B2 | 8/2012 | Bonny |
| 8,278,413 B2 | 10/2012 | Bonny |
| 2002/0042423 A1 | 4/2002 | Richert et al. |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |

(Continued)

FOREIGN PATENT DOCUMENTS

| | | |
|---|---|---|
| EP | 0 375 040 | 12/1989 |
| EP | 0 679 716 A1 | 11/1995 |

(Continued)

OTHER PUBLICATIONS

Mitsuyama et al, Pro-inflammatory signaling by Jun-N-terminal kinase in inflammatory bowel disease. Int J Mol Med. Mar. 2006;17(3):449-55.*

Hommes et al, Inhibition of stress-activated MAP kinases induces clinical improvement in moderate to severe Crohn's disease. Gastroenterology. Jan. 2002;122(1):7-14.*

Killick et al, Clusterin regulates b-amyloid toxicity via Dickkopf-1-driven induction of the wnt-PCP-JNK pathway. Molecular Psychiatry (2014) 19, 88-98.*

InVivoGen, Inc. SP600125 MAP Kinase Inhibitor—Autophagy Inhibitor—JNK inhibitor. Downloaded Jun. 9, 2014.*

(Continued)

*Primary Examiner* — Sheridan Swope
(74) *Attorney, Agent, or Firm* — Morgan, Lewis & Bockius LLP

(57) ABSTRACT

The present invention refers to the use of protein kinase inhibitors and more specifically to the use of inhibitors of the protein kinase c-Jun amino terminal kinase, JNK inhibitor sequences, chimeric peptides, or of nucleic acids encoding same as well as pharmaceutical compositions containing same, for the treatment of non-chronic or chronic inflammatory digestive diseases, such as colitis, including e.g. Ulcerative colitis, Crohn's disease, diversion colitis, ischemic colitis, infectious colitis, fulminant colitis, chemical colitis, microscopic colitis, lymphocytic colitis, and atypical colitis, etc.

11 Claims, 23 Drawing Sheets

(56) References Cited

U.S. PATENT DOCUMENTS

| | | |
|---|---|---|
| 2003/0108539 A1* | 6/2003 | Bonny .................. 424/94.63 |
| 2003/0124113 A1 | 7/2003 | Hillman et al. |
| 2003/0148395 A1 | 8/2003 | Liu et al. |
| 2003/0220480 A1 | 11/2003 | Bonny |
| 2004/0058875 A1 | 3/2004 | Gamache |
| 2004/0082509 A1 | 4/2004 | Bonny |
| 2004/0265879 A1 | 12/2004 | Iversen et al. |
| 2005/0059597 A1 | 3/2005 | Tymianski |
| 2005/0106695 A1 | 5/2005 | Bonny |
| 2006/0094753 A1 | 5/2006 | Pang et al. |
| 2006/0223807 A1 | 10/2006 | Davis et al. |
| 2006/0258706 A1 | 11/2006 | Saindane |
| 2006/0270646 A1 | 11/2006 | Graczyk et al. |
| 2007/0003531 A1 | 1/2007 | Mukherji et al. |
| 2007/0015779 A1 | 1/2007 | Griffin et al. |
| 2007/0060514 A1* | 3/2007 | Bonny .................. 514/12 |
| 2008/0008749 A1 | 1/2008 | Pearlman et al. |
| 2012/0101046 A1 | 4/2012 | Hirai et al. |
| 2012/0258982 A1 | 10/2012 | Cheung et al. |

FOREIGN PATENT DOCUMENTS

| | | |
|---|---|---|
| EP | 0 897 002 A2 | 2/1999 |
| EP | 1 364 949 A1 | 11/2003 |
| EP | 1676574 A2 | 7/2006 |
| JP | 58-146538 | 9/1983 |
| JP | 02-221294 | 4/1990 |
| JP | 2-221294 | 9/1990 |
| WO | 92-18138 A1 | 10/1992 |
| WO | 93-18759 A1 | 9/1993 |
| WO | 94-04562 A1 | 3/1994 |
| WO | 94-04686 A1 | 3/1994 |
| WO | 94-05311 A1 | 3/1994 |
| WO | 94-23751 A1 | 10/1994 |
| WO | 95-34295 A | 12/1995 |
| WO | 96/34093 | 10/1996 |
| WO | 97-05265 A | 2/1997 |
| WO | 97-10836 A | 3/1997 |
| WO | 98-11907 A | 3/1998 |
| WO | 98-23781 A1 | 6/1998 |
| WO | 98-44106 A1 | 10/1998 |
| WO | 98-47913 A1 | 10/1998 |
| WO | 98-49188 A1 | 11/1998 |
| WO | 98-51325 A2 | 11/1998 |
| WO | 98-51825 A1 | 11/1998 |
| WO | 98-52614 A | 11/1998 |
| WO | 99-07728 A2 | 2/1999 |
| WO | 99-16787 A1 | 4/1999 |
| WO | 9920624 A1 | 4/1999 |
| WO | 99-49879 A | 10/1999 |
| WO | 99-50282 A2 | 10/1999 |
| WO | 99-58561 A1 | 11/1999 |
| WO | 99-67284 A2 | 12/1999 |
| WO | 00-12587 A2 | 3/2000 |
| WO | 00-41719 A1 | 7/2000 |
| WO | 01-10888 A1 | 2/2001 |
| WO | 01-13957 A2 | 3/2001 |
| WO | 01-15511 A2 | 3/2001 |
| WO | 01-27268 A2 | 4/2001 |
| WO | 01/39784 | 6/2001 |
| WO | 01/82975 | 11/2001 |
| WO | 02-31109 A2 | 4/2002 |
| WO | 02/32437 | 4/2002 |
| WO | 02-061105 A2 | 8/2002 |
| WO | 02-062396 A2 | 8/2002 |
| WO | 02-065986 A2 | 8/2002 |
| WO | 02-069930 A1 | 9/2002 |
| WO | 02-081504 A2 | 10/2002 |
| WO | 02-081505 A2 | 10/2002 |
| WO | 03/008553 | 1/2003 |
| WO | 03/057725 | 7/2003 |
| WO | 03-075917 A1 | 9/2003 |
| WO | 03-103698 A1 | 12/2003 |
| WO | 03-103718 A2 | 12/2003 |
| WO | 03/106491 | 12/2003 |
| WO | 2004-022580 A2 | 3/2004 |
| WO | 2004-035793 A1 | 4/2004 |
| WO | 2004/037196 | 5/2004 |
| WO | 2004-045535 A2 | 6/2004 |
| WO | 2004-054501 A2 | 7/2004 |
| WO | 2004060318 A2 | 7/2004 |
| WO | 2004-070052 A2 | 8/2004 |
| WO | 2004-092339 A2 | 10/2004 |
| WO | 2005-084158 A2 | 9/2005 |
| WO | 2005-097116 A1 | 10/2005 |
| WO | 2006/001582 | 1/2006 |
| WO | 2006021458 A2 | 3/2006 |
| WO | 2006/050930 | 5/2006 |
| WO | 2007-031098 A1 | 3/2007 |
| WO | 2007/031280 | 3/2007 |
| WO | 2008-028860 A1 | 3/2008 |
| WO | 2008095943 A1 | 8/2008 |
| WO | 2008094208 A3 | 10/2008 |
| WO | 2009/137602 | 11/2009 |
| WO | 2009-143864 A1 | 12/2009 |
| WO | 2009-143865 A1 | 12/2009 |
| WO | 2009/144038 | 12/2009 |
| WO | 2009144037 A1 | 12/2009 |
| WO | 2010/065850 | 6/2010 |
| WO | 2011/160653 A1 | 12/2011 |
| WO | 2011/160827 A2 | 12/2011 |
| WO | 2012/048721 A1 | 4/2012 |
| WO | 2012/048893 A1 | 4/2012 |
| WO | 2013/091670 | 6/2013 |
| WO | 2013/091896 | 6/2013 |
| WO | 2014206426 A1 | 12/2014 |

OTHER PUBLICATIONS

Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.

Adler, et al.—Regulation of JNK Signaling by GSTp—The EMBO Journal—Mar. 1, 1999—pp. 1321-1334—vol. 18—No. 5—European Molecular Biology Organization—USA.

Brady, Leo and Dodson, Guy—Reflections on a Peptide—Nature—News and Views—Drug Design—Apr. 21, 1994—pp. 692-693—vol. 368 (6473)—Nature Publishing Group—USA.

Briand et al—A Retro-Inverso Peptide Corresponding to the GH Loop of Foot-and-Mouth Disease Virus Elicits High Levels of Long-Lasting Protective Neutralizing Antibodies—Proceedings of National Academy of Sciences—Immunology—Nov. 1997—pp. 12545-12550—vol. 94—National Academy of Sciences—USA.

Brugidou et al.—The Retro-Inverso Form of a Homeobox-Derived Short Peptide is Rapidly Internalized by Cultured Neurons: A New Basis for an Efficent Intracellular Delivery System—Biochemical and Biophysical Research Communications—Sep. 14, 1995—pp. 685-693—vol. 214—No. 2—Academic Press, Inc.—USA.

Chie et al.—Identification of the Site of Inhibition of Oncogenic ras-p21-Induced Signal Transduction by a Peptide from a Ras Effector Domain—Journal of Protein Chemistry—Nov. 4, 1999—pp. 881-884—vol. 18—No. 8—USA.

Chorev et al.—A Dozen Years of Retro-Inverso Peptidomimetics—Accounts of Chemical Research—1993—pp. 266-273—vol. 26—American Chemical Society—USA.

Chorev et al.—Recent Developments in Retro Peptides and Proteins—An Ongoing Topochemical Exploration—Oct. 1995—pp. 438-445—vol. 13—No. 10—TIBTECH (Trends in Biotechnology) Elsevier Science Ltd.—USA.

Dang et al.—Nuclear and Nucleolar Targeting Sequences of c-erb-A, c-myb, N-myc, p53, HSP70, and HIV tat Proteins—Journal of Biological Chemistry—Oct. 25, 1989—pp. 18019-18023—vol. 264—No. 30—The American Society for Biochemistry and Molecular Biology, Inc.—USA.

Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP 002044485—USA.

(56) References Cited

OTHER PUBLICATIONS

Elliott et al.—Intercellular Trafficking and Protein Delivery by a Herpesvirus Structural Protein—Cell—Jan. 24, 1997—pp. 223-233—vol. 88—No. 2—Cell Press—United Kingdom.
Frankel et al.—Activity of Synthetic Peptides from the Tat Protein of Human Immunodeficiency Virus Type 1—Proceedings of National Academy of Sciences—Biochemistry—Oct. 1989—pp. 7397-7401—vol. 86—National Academy of Sciences—USA.
Giorello et al—Inhibition of Cancer Cell Growth and c-Myc Transcriptional Activity by a c-Myc Helix 1-Type Peptide Fused to an Internalization Sequence—Cancer Research—Aug. 15, 1998—pp. 3654-3659—vol. 58—USA.
Guichard et al.—Partially Modified Retro-Inverso Pseudopeptides as Non-Natural Ligands for the Human Class I Histocompatibility Molecule HLA-A2—Journal of Medicinal Chemistry—1996—pp. 2030-2039—vol. 39—American Chemical Society—USA.
Hauber et al.—Mutational Analysis of the Conserved Basic Domain of Human Immunodeficiency Virus tat Protein—Journal of Virology—Mar. 1989—pp. 1181-1187—vol. 63—No. 3—Americal Society of Microbiology—USA.
Inhibit.Dictionary.com—The American Heritage® Stedman's Medical Dictionary—Houghton Mifflin Company—One Page—Internet document: http://dictionary.reference.com/browse/inhibit—Accessed on Oct. 10, 2007—USA.
Jackson et al.—Heat Shock Induces the Release of Fibroblast Growth Factor 1 from NIH 3T3 Cells—Proceedings of National Academy of Sciences—Cell Biology—Nov. 1992—pp. 10691-10695—vol. 89—National Academy of Sciences—USA.
Jameson et al.—A Rationally Designed CD4 Analogue Inhibits Experimental Allergic Encephalomyelitis—Nature—Letters to Nature—Apr. 21, 1994—pp. 744-746—vol. 368 Nature Publishing Group—USA.
Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.
Kida et al.—Design and Synthesis of a Tat-related Gene Transporter: A Tool for Carrying the Adenovirus Vector into Cells—Bioorganic and Medicinal Chemistry Letters—Dec. 6, 2005—pp. 743-745—vol. 16—ScienceDirect—Elsevier Ltd—USA.
Kieber-Emmons et al.—Therapeutic Peptides and Peptidomimetics—Current Opinion in Biotechnology—1997—pp. 435-441—vol. 8—Current Biology Ltd.—USA.
Kishan, K.V. Radha and Agrawal, Vishal—SH3-like Fold Proteins are Structurally Conserved and Functionally Divergent—Current Protein and Peptide Science—1995—pp. 143-150—vol. 6—Nentham Science Publishers Ltd.—USA.
Kisselev, Lev—Polypeptide Release Factors in Prokaryotes and Eukaryotes: Same Function, Different Structure—Jan. 2002—pp. 8-9—vol. 10—Structure—Elsevier Science Ltd—USA.
Lebleu, Bernard—Delivering Information-Rich Drugs—Prospects and Challenges—Meeting Report—Apr. 1996—pp. 109-110—vol. 14—No. 4—TIBTECH (Trends in Biotechnology) Elsevier Science Ltd.—USA.
Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.
Lewis et al.—Lymphoma Cell Uptake of Radiometal- and Fluorescent-Labelled BCL-2 Antisense PNA Conjugates is Mediated by a Retro-Inverso Delivery Peptide—Abstracts—Journal of Label Compounds and Radiopharmaceuticals—2003—p. S13—vol. 46—S1/S403—XP-002347557—USA
Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.
Lim et al.—Penetration Enhancement in Mouse Skin and Lipolysis in Adipocytes by TAT-GKH, A New Cosmetic Ingredient—Journal of Cosmetic Science—Sep./Oct. 2003—pp. 483-491—vol. 54—USA.
Lin et al.—Inhibition of Nuclear Translocation of Transcription Factor NF-kappa B by a Synthetic Peptide Containing a Cell Membrane-Permeable Motif and Nuclear Localization Sequence - Journal of Biological Chemistry - Jun. 16, 1995—pp. 14255-14258—vol. 270—No. 24—The American Society for Biochemistry and Molecular Biology, Inc.—USA.
Lloyd-Williams et al.—Chapter 5—Chemical Approaches to the Synthesis of Peptides and Proteins—1997—Formation of Disulfide Bridges—pp. 209-236—CRC Press LLC—USA.
Lloyd-Williams et al.—Chapter 6—Chemical Approaches to the Synthesis of Peptides and Proteins—1997—Peptide Libraries—pp. 237 and 264-267—CRC Press LLC—USA.
Mann, David A. and Frankel, Alan D.—Endocytosis and Targeting of Exogenous HIV-1 Tat Protein—The EMBO Journal—1991—pp. 1733-1739—vol. 10—No. 7—Oxford University Press—United Kingdom.
Marino et al.—Inhibition of Experimental Autoimmune Encephalomyelitis in SJL Mice by Oral Administration of Retro-Inverso Derivative of Encephalitogenic Epitope P87-99—European Journal of Immunology—1999—pp. 2560-2566—vol. 29—Wiley-VCH Verlag GmbH—Weinheim—Germany.
Marks et al.—Protein Targeting by Tyrosine- and Di-leucine-based Signals: Evidence for Distinct Saturable Components - the Journal of Cell Biology—Oct. 1, 1996—pp. 341-354—vol. 135—No. 2—The Rockefeller University Press—USA.
Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd—USA.
Mazur, Dan J. and Perrino, Fred W.—Identification and Expression of the TREX1 and TREX2 cDNA Sequences Encoding Mammalian 3'→5' Exonucleases—The Journal of Biological Chemistry—Jul. 9, 1999—pp. 19655-19660—vol. 274—No. 28—The American Society for Biochemistry and Molecular Biology, Inc.—USA.
Melikov, K. and Chernomordik, L.V.—Review—Arginine-rich Cell Penetrating Peptides: From Endosomal Uptake to Nuclear Delivery—Cellular and Molecular Life Sciences—Oct. 18, 2005—pp. 2739-2749—vol. 62—Birkhauser Verlag—Switzerland.
Messer, Jr., Dr. William S.—MBC 3320 Posterier Pituitary Hormones—Vasopression and Oxytocin—Apr. 3, 2000—pp. 1-5—,http://www.neurosci.pharm.utoledo.edu/MBC3320/vasopressin.htm>—USA.
Mi et al.—Characterization of a Class of Cationic Peptides able to Facilitate Efficient Protein Transduction in Vitro and in Vivo—Article—Molecular Therapy—Oct. 2000—pp. 339-347—vol. 2—No. 4—The American Society of Gene Therapy—USA.
Milano et al.—A Peptide Inhibitor of c-Jun NM2-terminal Kinase Reduces Myocardial Ischemia-reperfusion Injury and Infarct Size in Vivo—American Journal of Physiology—Heart Circulation Physiology—Apr. 2007—pp. H1828-H1835—vol. 292—www.ajpheart.org—The American Physiological Society—USA.
Mooi et al.—Regulation and Structure of an *Escherichia coli* Gene Coding for an Outer Membrane Protein involved in Export of K88ab Fimbrial Subunits—Nucleic Acids Research—1996—pp. 2443-2457—vol. 14—No. 6—IRL Press Linited—United Kingdom.
Moon et al. Bcl-2 Overexpression Attenuates SP600125-induced Apoptosis in Human Leukemia U937 Cells—Cancer Letters—Feb. 3, 2008—pp. 316-325—vol. 264—ScienceDirect—Elsevier Ireland Ltd—Ireland.
Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.
Moulin, Nathalie and Widman, Christian—Islet-Brain (IB)/JNK-Interacting Proteins (JIPs): Future Targets for the Treatment of Neurodegenerative Diseases?—Current Neurovascular Research—2004—pp. 111-127—vol. 1—No. 2—Institut de Biologie Cellulaire et de Morphologie (IBCM)—Université de Lusanne—Switzerland—Bentham Science Publishers Ltd.—USA.

(56) References Cited

OTHER PUBLICATIONS

Nagahara et al.—Transduction of Full-Length TAT Fusion Proteins into Mammalian Cells: TAT-p27Kip1 Induces Cell Migration—Nature Medicine—Dec. 1998—pp. 1449-1452—vol. 4—No. 12—Nature America Inc.—USA.
Negri at al.—Design of a Novel Peptide Inhibitor of the JNK Signaling Pathway—1217-P—Journal—Diabetes—Abstract Book—61st Scientific Session—Jun. 2001—p. A294—vol. 50—Supplement No. 2—American Diabetes Association—USA.
Neundorf et al.—Detailed Analysis Concerning the Biodistribution and Metabolism of Human Calcitonin-Derived Cell-Penetrating Peptides—Bioconjugate Chemistry—Jul. 24, 2008—pp. 1596-1603—vol. 19—No. 8—American Chemical Society—USA.
Ngo et al.—Computational Complexity, Protein Structure Prediction, and the Levinthal Paradox—The Protein Folding Problem and Tertiary Structure Prediction—Merz et al. (Editors)—1994—pp. 433, 492-495—Birkhauser Boston—USA.
Noguchi et al.—Regulation of c-Myc through Phosphorylation at Ser-62 and Ser-71 by c-Jun N-Terminal Kinase—Journal of Biological Chemistry—Nov. 12, 1999—pp. 32580-32587—vol. 274—No. 46—The American Society for Biochemistry and Molecular Biology, Inc.—USA.
Nori et ai.—Tat-Conjugated Synthetic Macromolecules Facilitate Cytoplasmic Drug Delivery to Human Ovarian Carcinoma Cells—Bioconjugate Chemistry—Nov. 16, 2002—pp. 44-50—vol. 14—No. 1—American Chemical Society—USA.
Witkowski et al.—Conversion of a β-Ketoacyl Synthase to a Malonyl Decarboxylase by Replacement of the Active-Site Cysteine with Glutamine—Biochemistry—Aug. 18, 1999—pp. 11643-11650—vol. 38—American Chemical Society—USA.
Wyszko et al.—Interaction of Native RNAs with Tat Peptides—NATO Science Series, 3: High Technology 1999, 70 (RNA Biochemistry and Biotechnology), Sep. 9, 2002—pp. 277-290—Institute of Bioorganic Chemistry of the Polish Academy of Sciences, Poznan—Poland—Kluwer Academic Publishers—Chemical Abstracts Database Accession No. 133:204452 CA—XP002554007—Poland.
Yamamoto et al.—Molecular Design of Bioconjugated Cell Adhesian Peptide with a Water-Soluble Polymeric Modifer for Enhancement of Antimetastatic Effect—Current Drug Targets—2002—pp. 123-130—vol. 3—Bentham Science Publishers Ltd.—USA.
Yang et al.—Differential Targeting of MAP Kinases to the ETS-Domain Transcription Factor Elk-1—The EMBO Journal—1998—pp. 1740-1749—vol. 17—No. 6—European Molecular Biology Organisation—Oxford University Press—United Kingdom.
Yasuda et al.—The JIP Group of Mitogen-Activated Protein Kinase Scaffold Proteins—Molecular and Cellular Biology—Oct. 1999—pp. 7245-7254—vol. 19—No. 10—American Society for Microbiology—USA.
Zhang et al.—Preparation of Functionally Active Cell-Permeable Peptides by Single-Step Ligation of Two Peptide Modules—Proceedings of National Academy of Sciences—Biochemistry—Aug. 1998—pp. 9184-9189—vol. 95—National Academy of Sciences—USA.
Zoukhri et al.—c-Jun NH2-Terminal Kinase Mediates Interleukin-1 β-Induced Inhibition of Lacrimal Gland Secretion—Journal of Neurochemistry—2006—pp. 126-135—vol. 96—International Society for Neurochemistry—USA.
NCBI Sequence Viewer—Accession No. AAD20443—Reports—Islet-Brain 1 (*Homo sapiens*)—Two References—Mooser et al.—Mar. 17, 1999—2 pages—USA.
NCBI Sequence Viewer—Accession No. AAD22543—Reports—Islet-Brain 1 (*Rattus norvegicus*)—Three References—Bonny et al.—Mar. 1, 2006—2 pages—USA.
NCBI Sequence Viewer—Accession No. AAF32323—Reports—Islet-Brain 2 (*Homo sapiens*)—Two References—Negri et al.—Feb. 9, 2000—2 pages—USA.
NCBI Sequence Viewer—Accession No. AF074091—Reports—*Homo sapiens* Islet-Brain 1 mRNA—Complete Cds.—Two References—Mooser et al.—Mar. 17, 1999—2 pages—USA.
NCBI Sequence Viewer—Accession No. AF108959—Reports—*Rattus norvegicus* Islet-Brain 1 (IB1) mRNA—Complete Cds.—Three References—Bonny et al.—Mar. 1, 2006—2 pages—USA.
NCBI Sequence Viewer—Accession No. AF218778—Reports—*Homo sapiens* Islet-Brain 2 mRNA—Complete Cds—Three References—Kristensen et al.—Mar. 2, 2006—2 pages—USA.
NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.
Ahmed, Shafiq Uddin and Milner, Jo—Basal Cancer Cell Survival Involves JNK2 Suppression of a Novel JNK1/c-Jun/Bcl-3 Apoptotic Network—PLoS One—Oct. 2009—pp. 1-13—vol. 4—Issue 10—University of York—United Kingdom.
Ahmed et al., "Basal cancer cell survival involves JNK2 suppression of a novel JNK1/c-Jun/Bcl-3 apoptotic network," Plos One 4(10): e7305 (2009).
Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).
Bost et al., "The Jun kinase 2 isoform is preferentially required for epidermal growth factor-induced transformation of human A549 lung carcinoma cells," Molecular and Cellular Biology, 19(3): 1938-1949 (1999).
Chang Lufen et al., JNK1 is required for maintenance of neuronal microtubules and controls phosphorylation of microtubule-associated proteins, Developmental Cell, 4(4): 521-533 (2003).
Hunot Stephan et al., "JNK-mediated induction of cyclooxygenase 2 is required for neurodegeneration in a mouse model of Parkinson's disease," Proceedings of the National Academy of Sciences of the United States of America,101 (2): 665-670 (2004).
Jaeschke et al., "Disruption of the Jnk2 (Mapk9) gene reduces destructive insulitis and diabetes in a mouse model of type I diabetes," Proceedings of the National Academy of Sciences of the United States of America, 102(19): 6931-6935.
Kaneto et al., "Possible novel therapy for diabetes with cell-permeable JNK-inhibitory peptide," Nature Medicine, 10 (10):1128-1132 (2004).
Kuan et al., "A critical role of neural-specific JNK3 for ischemic apoptosis," Proceedings of the National Academy of Sciences of the United States of America, 100(25): 15184-15189 (2003).
Polyakov et al., "Novel Tat-peptide chelates for direct transduction of technetium-99m and rhenium into human cells for imaging and radiotherapy" Bioconjugate Chem., 11: 762-771 (2000).
Saar et al., "Cell-penetrating peptides: a comparative membrane toxicity study," Analytical Biochemistry, 345(1):55-65 (2005).
Sabapathy, "Role of the JNK pathway in human diseases," Progress in Molecular Biology and Translational Science, 106:145-169 (2012).
Salh, "c-Jun N-terminal kinases as potential therapeutic targets," Expert Opin Ther Targets, 11(10):1339-1353 (2007).
Seki et al., "A liver full of JNK: signaling in regulation of cell function and disease pathogenesis, and clinical approaches," Gastroenterology, 143(2):307-320 (2012).
Sumara et al., "Jnking atherosclerosis," Cellular and Molecular Life Sciences, Birkhauser Verlag, 62(21): 2487-2494 (2005).
Tachibana et al., "JNK1 is required to preserve cardiac function in the early response to pressure overload, Biochemical and Biophysical Research Communications," 343(4): 1060-1066 (2006).
Westwick et al., "Activatin of Jun kinase is an early event in hepatic regeneration," The Journal of the Clinical Investigation, 95(2): 803-810 (1995).
Tan, Selective Inhibition of ErbB2-Overexpressing Breast Cancer In vivo by a Novel TAT-Based ErbB2-Targeting Signal Transducers and Activators of Transcription 3-Blocking Peptide, Cnacer Res, 66:3764-3775, 2008.
De Paiva, Essential Role for c-Jun N-Terminal Kinase 2 in Corneal Epithelial Response to Desiccating Stress, Arch Ophthalmol., 127:12, 1625-1631, 2009.

(56) References Cited

OTHER PUBLICATIONS

Bowie et al., "Deciphering the message in protein sequences: tolerance to amino acid substitutions," Science, 247 (4948): 1306-1310 (1990).
Database WPI, Thompson Scientific, Accession No. 2010-M79716, 2010, 3 pages; XP002643212.
Ferrandi et al., "Inhibition of c-Jun N-terminal kinase decreases cardiomyocyte apoptosis and infarct size after myocardial ischemia and reperfusion in anaesthetized rats," British Journal of Pharmacology, 142(6): 953-960 (2004).
Hirt et al., "D-JNKI1, a cell-penetrating c-Jun-N-terminal kinase inhibitor, protects against cell death in severe cerebral ischemia," Stroke, 35(7): 1738-1743 (2004).
Kugler et al., "MAP kinase pathways involved in glioblastoma response to erucylphosphocholine," International Journal of Oncology, 25(6):1721-1727 (2004).
Stedman's Online Dictionary Definition of "inflammation", Obtained from www.pdrel.com, last viewed on Dec. 18, 2010, 2 pages.
Wang et al., "A single amino acid determines lysophospholipid specificity of the S1P1 (EDG1) and LPA1 (EDG2) phospholipid growth factor receptors," Journal of Biological Chemistry, 276(52): 49213-49220 (2001).
Wells, "Additivity of mutational effects in proteins," Biochemistry, 29(37): 8509-8517 (1990).
Aarts et al.—Treatment of Ischemic Brain Damage by Perturbing NMDA Receptor—PSD-95 Protein Interactions—Science—Oct. 25, 2002—pp. 846-850—vol. 298—www.sciencemag.org—USA.
Abaza et al.—Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin—Journal of Protein Chemistry—1992—pp. 433-444—vol. 11—No. 5—USA.
Agrawal, Vishal and Kishan, K.V. Radha—Promiscuous Binding Nature of SH3 Domains to their Target Proteins—Protein and Peptide Letters—2002—pp. 185-193—vol. 9—No. 3—Bentham Science Publishers Ltd.—USA.
Aldrian-Herrada et al.—A Peptide Nucleic Acid (PNA) is More Rapidly Internalized in Cultured Neurons when Coupled to a Retro-Inverso Delivery Peptide. The Antisense Activity Depresses the Target mRNA and Protein in Magnocellular Oxytocin Neurons—Nucleic Acids Research—1998—pp. 4910-4916—vol. 26—No. 21—Oxford University Press—UK.
Assi et al.—The Specific JNK Inhibitor SP600125 Targets Tumour Necrosis Factor-α Production and Epithelial Cell Apoptosis in Acute Murine Colitis—Immunology—2006—pp. 112-121—Blackwell Publishing Ltd.—USA.
Barr et al.—Identification of the Critical Features of a Small Peptide Inhibitor of JNK Activity—Mar. 20, 2002—pp. 10987-10997—vol. 277—No. 13—USA.
Berendsen, Herman J.C.—A Glimpse of the Holy Grail?—Oct. 23, 1998—pp. 642-643—vol. 282—No. 5389—Science—Research Library—USA.
Bessalle et al.—All-D-Magainin: Chirality, Antimicrobial Activity and Proteolytic Resistance—FEBS Letters—Nov. 12, 1990—pp. 151-155—vol. 274—Nos. 1/2—Federation of European Biochemical Societies—Elsevier Science Publishes B.V.—The Netherlands.
Bonny et al.,—Cell-Permeable Peptide Inhibitors of JNK: Novel Blockers of Beta-Cell Death—Diabetes—Jan. 2001—pp. 77-82—vol. 50—No. 1—USA.
Bonny et al.—IB1, A JIP-1-Related Nuclear Protein Present in Insulin-Secreting Cells—Journal of Biological Chemistry—Jan. 23, 1998—pp. 1843-1846—vol. 273—No. 4—USA.
Bonny et al.—Pancreatic-Specific Expression of the Glucose Transporter Type 2 Gene: Identification of cis-Elements and Islet-Specific trans-Acting Factors—MOL ENDO—Molecular Endocrinology—1995—pp. 1413-1426—vol. 9—No. 10—The Endocrine Society—USA.
Bonny et al.—Targeting the JNK Pathway as a Therapeutic Protective Strategy for Nervous Systems Diseases—2005—pp. 57-67—vol. 16—No. 1—Freund & Pettman—United Kingdom.
Borsello et al.—A Peptide Inhibitor of c-Jun N-Terminal Kinase Protects Against Excitotoxicity and Cerebral Ischemia—Aug. 24, 2003 (Sep. 2003)—pp. 1180-1186—vol. 9—No. 9—Nature Medicine—USA.
Borsello, Tiziana and Bonny, Christophe—Use of Cell-Permeable Peptides to Prevent Neuronal Degeneration—Trends in Molecular Medicine—May 2004—pp. 239-244—vol. 10—No. 5—Elsevier Ltd—www.sciencedirect.com—USA.
Bradley, Christina Marchette and Barrick, Doug—Limits of Cooperativity in a Structurally Modular Protein: Response of the Notch Ankyrin Dpmaon to Analogous Alanine Substitutions in Each Repeat—JMB —Journal of Molecular Biology—Nov. 22, 2002—pp. 373-386—vol. 324—USA.
Branden et al.—A Peptide Nucleic Acid-Nuclear Localization Signal Fusion that Mediates Nuclear Transport of DNA—Nature Biotechnology—Aug. 1999—pp. 784-787—vol. 17—Nature America Inc.—USA.
Branden, Carl and Tooze, Carl—Introduction to Protein—Second Edition—1999—Garland Publishing, Inc.—p. 382—USA.
Branden, Carl and Tooze, Carl—Introduction to Protein—1991—Garland Publishing, Inc.—p. 247—USA.
Cardozo et al.—Cell-Permeable Peptides Induce Dose- and Length-Dependent Cytotoxic Effects—Biochimica et Biophysica Acta—Jun. 14, 2007—pp. 2222-2234—No. 1768—ScienceDirect—Elsevier B.V.—The Netherlands.
Chaloin et al.—Design of Carrier Peptide-Oligonucleotide Conjugates with Rapid Membrane Translocation and Nuclear Localization Properties—Biochemical and Biophysical Research Communications—Article No. RC978050—1998—pp. 601-608—vol. 243—No. 2—Academic Press—Elsevier B.V.—The Nethlands.
Creighton, Thomas E. (Editor)—Janin, Jaël—Protein—Protein Interactions—Encyclopedia of Molecular Biology—1999—pp. 2027-2033—vol. 1—A Wiley-Interscience Publication—John Wiley & Sons, Inc.—USA.
Derossi et al.—Cell Internalization of the Third Helix of the Antennapedia Homeodomain Is Receptor-independent—The Journal of Biological Chemistry—Jul. 26, 1996—pp. 18188-18193—vol. 271—No. 30—The American Society for Biochemistry and Molecular Biology, Inc.—USA.
Designing Custom Peptides—Sigma Genosys—Technical Bulletin—Dec. 16, 2004—2 pages—<http://www.sigma-genosys.com/peptide_design.asp>—USA.
Dickens et al.—Database—Uniprot—Retrieved from EBI—Database Accession No. Q9WVI9—Abstracts—Feb. 28, 2003—Document No. XP-002366175—USA.
Dickens et al.—A Cytoplasmic Inhibitor of the JNK Signal Transduction Pathway—Science—Aug. 1, 1997—pp. 693-696—vol. 277—No. 5326—Science Magazine—USA.
Dietz, Gunner P.H. and Bahr, Mathias—Review—Delivery of Bioactive Molecules into the Cell: The Trojan Horse Approach—Molecular and Cellular Neuroscience—2004—pp. 85-131—vol. 27—Elsevier Inc.—The Netherlands.
Dominguez-Bendala et al.—TAT-Mediated Neurogenin 3 Protein Transduction Stimulates Pancreatic Endocrine Differentiation In Vitro—Diabetes—Mar. 2005—pp. 720-726—vol. 54—The American Diabetes Association—USA.
Fawell et al.—Tat-Mediated Delivery of Heterologous Proteins into Cells—Cell Biology—Proceedings of the National Academy of Sciences—Jan. 8, 1994—pp. 664-668—vol. 91—Biogen Inc.—USA.
Fornoni et al.—The L-Isoform but not D-Isoforms of a JNK Inhibitory Peptide Protects Pancreatic β-cells—Biochemical and Biophysical Research Communications—Jan. 2, 2007—pp. 227-233—vol. 354—ScienceDirect—Elsevier Inc.—USA.
Frankel, Alan D. and Pabo, Carl O.—Cellular Uptake of the Tat Protein from Human Immunodeficiency Virus—Cell—Dec. 23, 1988—pp. 1189-1193—vol. 55—Cell Press—USA.

(56) References Cited

OTHER PUBLICATIONS

Fujita et al.—Prophylactic or Therapeutic Agent for Retinal Diseases and Method for Preventing or Treating Retinal Diseases, Each Comprising JNK (C-JUN N-Terminal Kinase)-Inhibiting Peptide, and Use of the Peptide—International Application No. PCT/JP2010/55208—Santen Pharmaceutical Co., Ltd.—Database WPI—Thompson Scientific—pp. 1-4—XP-002643212—USA.

Futaki et al.—Arginine-rich Peptides—An Abundant Source of Membrane-Permeable Peptides Having Potential as Carriers for Intracellular Protein Delivery—The Journal of Biological Chemistry—Feb. 23, 2001—pp. 5836-5840—vol. 276—No. 8—The American Society of Biochemistry and Molecular Biology, Inc.—USA.

Gammon et al.—Quantitative Analysis of Permeation Peptide Complexes Labeled with Technetium-99m: Chiral and Sequence-Specific Effects on Net Cell Uptake—Bioconjugate Chemistry—Mar. 4, 2003—pp. 368-376—vol. 14—No. 2—American Chemical Society—USA.

Gotthardt et al.—Interactions of the Low Density Lipoprotein Receptor Gene Family with Cytosolic Adaptor and Scaffold Proteins Suggest Diverse Biological Functions in Cellular Communications and Signal Transduction—The Journal of Biological Chemistry—Aug. 18, 2000—pp. 25616-25624—vol. 275—No. 33—The American Society for Biochemistry and Molecular Biology, Inc.—USA.

Guichard et al.—Antigenic Mimicry of Natural L-Peptides with Retro-Inverso-Peptidomimetics—Proceedings of the National Academy of Sciences—Immunology—Oct. 1994—pp. 9765-9769—vol. 91—The National Academy of Sciences—USA.

Gunaseelan et al.—Synthesis of Poly(ethylene glycol)-Based Saquinavir Prodrug Conjugates and Assessment of Release and Anti-HIV-1 Bioactivity Using a Novel Protease Inhibition Assay—Bioconjugate Chemistry—Oct. 28, 2004—pp. 1322-1333—vol. 15—No. 6—American Chemical Society—USA.

Gura, Trisha—Cancer Models: Systems for Identifying New Drugs Are Often Faulty—Science—Nov. 7, 1997—pp. 1041-1042—No. 278 (5340)—USA.

Hawiger, Jacek—Noninvasive Intracellular Delivery of Functional Peptides and Proteins—Current Opinion in Chemical Biology—1999—pp. 89-94—vol. 3—Elsevier Science Ltd—USA.

Hayashi et al.—Development of Oligoarginine-Drug Conjugates Linked to New Peptidic Self-Cleavable Spacers Toward Effective Intestinal Absorption—Bioorganic and Medicinal Chemistry Letters—Jul. 7, 2007—pp. 5129-5132—vol. 17—ScienceDirect—Elsevier Ltd—USA.

Heemskerk et al.—From Chemical to Drug: Neurodegeneration Drug Screening and the Ethics of Clinical Trials—Commentary—Nature Neuroscience Supplement—Nov. 2002—pp. 1027-1029—vol. 5—Nature Publishing Group—http://www.nature.com./natureneuroscience—USA.

Herve et al.—On the Immunogenic Properties of Retro-Inverso Peptides. Total Retro-Inversion of T-Cell Epitopes Causes a Loss of Binding to MHC II Molecules—Molecular Immunology—1997—pp. 157-163—vol. 34—No. 2—Elsevier Science Ltd.—United Kingdom.

Hillier et al.—*Homo sapiens*—The WashU-Merck EST Project—EMBL Sequence Database—R85141—Aug. 17, 1995—p. 1—XP-002076858—USA.

Ho et al.—Synthetic Protein Transduction Domains: Enhanced Transduction Potential in Vitro and in Vivo—Advances in Brief—Cancer Research—Jan. 15, 2001—pp. 474-477—vol. 61—USA.

Holinger et al.—Bak BH3 Peptides Antagonize Bcl-xL Function and Induce Apoptosis through Cytochrome c-independent Activation of Caspases—The Journal of Biological Chemistry—May 7, 1999—pp. 13298-13304—vol. 274—No. 19—The American Society for Biochemistry and Molecular Biology, Inc.—USA.

Holzberg et al.—Disruption of the c-JUN-JNK Complex by a Cell-permeable Peptide Containing the c-Jun δ Domain Induces Apoptosis and Affects a Distinct Set of Interleukin-1-induced Inflammatory Genes—The Journal of Biological Chemistry—Oct. 10, 2003—pp. 40213-40223—vol. 278—No. 41—The American Society for Biochemistry and Molecular Biology, Inc.—USA.

Houghten, Richard A.—General Method for the Rapid Solid-Phase Synthesis of Large Numbers of Peptides: Specificty of Antigen-Antibody Interaction at the Level of Individual Amino Acids—Proceedings of the National Academy of Sciences—Immunology—Aug. 1985—pp. 5131-5135—vol. 82—The National Academy of Sciences—USA.

Huq et al.—Specific Recognition of HIV-1 TAR RNA by a D-Tat Peptide—Comment—Nature Structural Biology—Nov. 1997—pp. 881-882—vol. 4—No. 11—Nature Publishing Group—http://www.nature.com/nsmb—USA.

Johnson, Gary L. and Nakamura, Kazuhiro—The c-jun Kinase/Stress-Activated Pathway: Regulation, Function and Role in Human Disease—Biochimica et Biophysica Acta—Jan. 4, 2007—pp. 1341-1348—vol. 1773—ScienceDirect—Elsevier B.V.—The Netherlands.

Jung, Günther (Editor)—Chapter 5—The Versatility of Nonsupport-Bound Combinatorial Libraries—Pinilla et al.—Combinatorial Peptide and Nonpeptide Libraries—A Handbook—May 1997—pp. 139-171—Wiley-VCH—USA.

Jung, Günther (Editor)—Chapter 11—Cyclic Peptide Libraries: Recent Developments—Spatola, Arno F. and Romanovskis, Peteris—Combinatorial Peptide and Nonpeptide Libraries—A Handbook—May 1997—pp. 327-347—Wiley-VCH—USA.

Nori, Aparna and Kopecek, Jindrich—Intracellular Targeting of Polymer-Bound Drugs for Cancer Chemotherapy—Advanced Drug Delivery Reviews—Dec. 24, 2004—pp. 609-636—vol. 57—ScienceDirect—Elsevier B.V.—The Netherlands.

Okitsu et al.—Protein Transduction Domains Enable Isolated Islets to Efficiently Internalize the Target Protein—Transplantation Proceedings—Feb. 2003—p. 479—vol. 35—Elsevier Science inc.—USA.

Pan et al.—Small Peptide Inhibitor of JNKs Protects Against MPTP-Induced Nigral Dopaminergic Injury via Inhibiting the JNK-SIgnaling Pathway—Laboratory Investigation—Feb. 2010—pp. 156-167—vol. 90—USCAP, Inc.—USA.

Parkinson's Disease: Challenges, Progress, and Promise—Publication—National Institute of Neurological Disorders and Stroke—National Institutes of Health—2004—22 pages—No. 05-5595—<http://www.ninds.nih.gov/disorders/parkinsons_disease/parkinsons_research_pr.htm.

Penco et ai.—Identification of an Import Signal for, and the Nuclear Localization of, Human Lactoferrin—Biotechnology and Applied Biochemistry—Dec. 2001—pp. 151-159—vol. 34—Portland Press Ltd—United Kingdom.

Pennington, Michael W. and Dunn, Ben M. (Editors)—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc.—USA.

Pennington, Michael W. and Dunn, Ben M. (Editors)—Chapter 12—Solid-Phase Synthesis of Peptides Containing the CH2NH Reduced Bond Surrogate—Pennington, Michael W.—Methods in Molecular Biology—vol. 35—Peptide Synthesis Protocols—1994—pp. 241-247—Humana Press Inc.—USA.

Pirvola et al.—Rescue of Hearing, Auditory Hair Cells, and Neurons by CEP-1347/KT7515, an Inhibitor of c-Jun N-Terminal Kinase Activation—The Journal of Neuroscience—01-01-200—pp. 43-50—vol. 20—No. 1—Society of Neuroscience—USA.

Pratner et al.—Synthesis and Characterization of a Gd-DOTA-D-Permeation Peptide for Magnetic Resonance Relaxation Enhancement of Intracellular Targets—Research Article—Massachusetts Institute of Technology—Molecular Imaging—Oct. 2003—pp. 333-341—vol. 2—No. 4—The Society of Molecular Imaging—USA.

Ramage, Robert and Epton, Roger (Editors)—Chapters 165 and 166—Guichard et al.—Chapter 167—Gur'Yanov et al.—EPS—Proceedings of the Twenty-Fourth European Peptide Symposium, Sep. 8-13, 1996, Edinburgh, Scotland—pp. 447-451—The European Peptide Society—Mayflower Scientific Ltd.—United Kingdom.

Ramage, Robert and Epton, Roger (Editors)—Chapter—183—Horvath et al.—Chapter 184—Hruby et al.—EPS—Proceedings of the Twenty-Fourth European Peptide Symposium, Sep. 8-13, 1996,

(56) References Cited

OTHER PUBLICATIONS

Edinburgh, Scotland—pp. 483-486—The European Peptide Society—Mayflower Scientific Ltd.—United Kingdom.
Ramanathan et al.—Targeting the Sodium-Dpendent Multivitamin Transporter (SMVT) for Improving the Oral Absorption Properties of a Retro-Inverso Tat Nonapeptide—Pharmaceutical Research—Jul. 2001—pp. 950-956—vol. 18—No. 7—USA.
Ribeiro et al.—Heme Oxygenase-1 Fused to a TAT Peptide Transduces and Protects Pancreatic β-Cells—BBRC—Biochemical and Biophysical Research Communications—Apr. 4, 2003—pp. 876-881—vol. 305—ScvienceDirect—Academic Press—Elsevier Science (USA)—USA.
Rickels et al.—Phage Display Selection of Ligand Residues Important for Src Homology 3 Domain Binding Specificity—Biochemistry—Proceedings of the National Academy of Science—Nov. 1995—pp. 10909-10913—vol. 92—National Academy of Science—USA.
Robinson et al.—Properties and Structure-Activity Studies of Cyclic β-hairpin Peptidomimetics Based on the Cationic Antimicrobial Peptide Protegrin I—Bioorganic & Medicinal Chemistry—Jan. 7, 2005—pp. 2055-2064—vol. 13—ScienceDirect—Elsevier Ltd.—USA.
Roduit, Raphaël and Schorderet, Daniel F.—MAP Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.
Rojas et al.—Controlling Epidermal Growth Factor (EGF)-Stimulated Ras Activation in Intact Cells by a Cell-Permeable Peptide Mimicking Phosphorylated EGF Receptor—Journal of Biological Chemistry—Nov. 1, 1996—pp. 27456-27461—vol. 271—No. 44—The American Society for Biochemistry and Molecular Biology, Inc.—USA.
Roy et al.—Role of the JNK Signal Transduction Pathway in Inflammatory Bowel Disease—World Journal of Gastroenterol—Jan. 14, 2008—pp. 200-202—vol. 14—No. 2—www.wjgnet.com—USA.
Ruben et al.—Structural and Functional Characterization of Human Immunodeficiency Virus tat Protein—Journal of Virology—Jan. 1989—pp. 1-8—vol. 63—No. 1—American Society for Microbiology—USA.
Rudikoff et al.—Single Amino Acid Substitution Altering Antigen-Binding Specificity—Immunology—Proceedings of the National Academy of Science—Mar. 1982—pp. 1979-1983—vol. 79—National Academy of Science—USA.
Rudinger, J.—Characteristics of the Amino Acids as Components of a Peptide Hormone Sequence—Peptide Hormones—1976—pp. 1-7—University Park Press, Baltimore—USA.
Saito, Naoyuki G. and Paterson, Yvonne—Contribution of Peptide Backbone Atoms to Binding of an Antigenic Peptide to Class 1 Major Histocompatibility Complex Module—Molecular Immunology—Nov. 13, 199—pp. 1133-1145—vol. 34—No. 16-17—Pergamon—Elsevier Science Ltd.—United Kingdom.
Schimmer et al—The BH3 Domain of BAD Fused to the Antennapedia Peptide Induces Apoptosis via its Alpha Helical Structure and Independent of Bcl-2—Cell Death and Differentiation—Feb. 18, 2001 pp. 725-733—vol. 8—No. 7—Canada.
Schinzel, R. and Drueckes, P.—The Phosphate Recognition Site of *Escherichia Coli* Maltodextrin Phosphorylase—FEBS Letters—Jul. 29, 1991—pp. 125-128—vol. 286—No. 1 and 2—Federation of European Biochemical Societies—Elsevier Science Publishers B.V.—The Netherlands.
Schwarze et al.—In Vivo Protein Transduction: Delivery of a Biologically Active Protein into the Mouse—Science—Sep. 3, 1999—pp. 1569-1572—vol. 285—Science Magazine—USA.
Sebestyen et al.—DNA Vector Chemistry: The Covalent Attachment of Signal Peptides to Plasmid DNA—Research—Nature Biotechnology—Jan. 16, 1998—pp. 80-85—vol. 16—USA.
Selective Dimerisation of Cysteines to form Heterodimers—Aim—Chemistry—Procedure—NJE—Feb. 3, 1997—One Page—USA.
Smilek et al.—A Single Amino Acid Change in a Myelin Basic Protein Peptide Confers the Capacity to Prevent Rather than Induce Experimental Autoimmune Encephalomyelitis—Immunology—Proceedings of the National Acadamy of Science—Nov. 1, 1991—pp. 9633-9637—vol. 88—No. 21—The National Academy of Science—USA.
Stevens et al.—Efficient Generation of Major Histocompatibility Complex Class I-Peptide Complexes Using Synthetic Peptide Libraries—The Journal of Biological Chemistry—Jan. 3, 1998—pp. 2874-2884—vol. 273—No. 5—The American Society for Biochemistry and Molecular Biology, Inc.—USA.
Stevens et al.—Peptide Length Preferences for Rat and Mouse MHC Class I Molecules Using Random Peptide Libraries—European Journal of Immunology—Apr.—pp. 1272-1279—vol. 28—No. 4—WILEY-VCH Verlag GmbH—Germany.
Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.
Thoren et al.—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.
Torchilin et al.—Fluorescence Microscopy to Follow the Targeting of Liposomes and Micelles to Cells and their Intracellular Fate—Advanced Drug Delivery Reviews—Jan. 2005—pp. 95-109—vol. 57—ScienceDirect Elsevier B.V.—The Netherlands.
Torgerson et al.—Regulation of NF-kappa B, AP-1, NFAT, and STAT1 Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.
Touchard et al.—A Peptide Inhibitor of c-Jun N-Terminal Kinase for the Treatment of Endotoxin-Induced Uveitis—Immunology and Microbiology—Investigative Ophthalmology & Visual Science—Sep. 2010—pp. 4683-4693—vol. 51—No. 9—Association for Research in Vision and Ophthalmology—USA.
Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.
Van Regenmortel et al.—D-Peptides as Immunogens and Diagnostic Reagents—Protein Engineering—Current Opinion of Biotechnology—1998—pp. 377-382—vol. 8—Current Biology Publications—France.
Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.
Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.
Vocero-Akbani et al.—Killing HIV-Infected Cells by Transduction with an HIV Protease-Activated Caspase-3 Protein—Nature Medicine—Jan. 1999—pp. 29-33—vol. 5—No. 1—Nature America Inc.—USA.
Voet, Donald and Voet, Judith G.—Abnormal Hemoglobins—1995—pp. 235-241—Biochemistry Second Edition—John Wiley & Sons, Inc.—USA.
Wadia et al.—Delivery of Novel Anti-Cancer Peptides by Protein Transduction Domains—Peptides—May 2004—pp. 65-69—American Pharmaceutical Review—USA.
Waldmeier et al.—Recent Clinical Failures in Parkinson's Disease with Apoptosis Inhibitors Underline the Need for a Paradigm Shift in Drug Discovery for Neurodegenerative Diseases—Biochemical Pharmacology—Nov. 15, 2006—pp. 1197-1206—vol. 72—No. 10—ScienceDirect—Elsevier Inc.—USA.
Walsh et al.—Erythrocyte Survival is Promoted by Plasma and Suppressed by a Bak-Derived BH3 Peptide that Interacts with Membrane-Associated Bcl-XL—Red Cells—Blood—May 1, 2002 pp. 3439-3448—vol. 99—No. 9—The American Society of Hematology—USA.

(56) References Cited

OTHER PUBLICATIONS

Wender et al.—The Design, Synthesis, and Evaluation of Molecules that Enable or Enhance Cellular Uptake: Peptoid Molecular Transporters—Proceedings of the National Academy of Science—Nov. 21, 2000—pp. 13003-13008—vol. 97—No. 24—The National Academy of Science—USA.

Whitmarsh et al.—A Mammalian Scaffold Complex that Selectively Mediates MAP Kinase Activation—Science—Sep. 11, 1998—pp. 1671-1674—vol. 281—5383—www.sciencemag.org—USA.

Whitmarsh, A.J. and Davis, R.J.—Transcription Factor AP-1 Regulation by Mitogen-Activated Protein Kinase Signal Transduction Pathways—Review—Journal of Molecular Medicine Oct. 7, 1996—pp. 589-607—vol. 74—No. 10—Springer-Verlag—USA.

Wilson, David—Preventing Nerve Cell Death in ALS—Internet document—<http://www.als.caJ_news/57.aspx>—Dec. 5, 2001—2 pages—USA.

Wishart et al.—A Single Mutation Converts a Novel Phosphotyrosine Binding Domain into a Dual-specificity Phosphatase—Communication—The Journal of Biological Chemistry—Nov. 10, 1995—pp. 26782-26785—vol. 270—No. 45—The American Society for Biochemistry and Molecular Biology, Inc.—USA.

Patel et al., "Getting into the brain-approaches to enhance brain drug delivery," CNS Drugs, 23(1): 35-58 (2009).

Parenteau et al., "Free uptake of cell-penetrating peptides by fission yeast," FEBS Letters, 579: 4873-4878 (2005).

Bogoyevitch et al., "Taking the cell by stealth or storm? Protein transduction domains (PTDs) as versatile vectors for delivery," DNA Cell Biol., 21(12):879-894 (2002).

Chemical Abstracts Accession No. 2004:27781 and CAS Registry File CN 647864-97-9.

InVivoGen, Inc., SP600125: MAP Kinase Inhibitor—Autophagy Inhibitor—JNK inhibitor, Downloaded Jun. 9, 2014.

Kelekar et al., "Bcl-2-family proteins: the role of the BH3 domain in apoptosis," Trends Cell Biol., 8(8):324-330 (1998).

Killick et al, "Clusterin regulates β-amyloid toxicity via Dickkopf-1-driven induction of the wnt-PCP-JNK pathway," Mol Psychiatry., 19(1):88-98 (2014).

Du H. et al., JNK inhibition reduces apoptosis and neovascularization in a murine model of age-related macular degeneration, Proc Natl Acad Sci U S A. Feb. 5, 2013;110(6):2377-82. Epub Jan. 22, 2013.

Iyer S. et al., RDP58, a rationally designed peptide, inhibits multiple forms of pathogenic inflammation through the inhibition of p38MAPK and JNK, Biopolymers, vol. 71, No. 3, 061, p. 298, Jan. 2013.

Noguchi H. et al., Cell Permeable Peptide of JNK Inhibitor Prevents Islet Apoptosis Immediately After Isolation and Improves Islet Graft Function, American Journal of Transplantation, vol. 5, No. 8, pp. 1848-1855, Aug. 2005.

Noguchi H. et al., Effect of JNK Inhibitor During Islet Isolation and Transplantation, Transplantation proceedings, vol. 40, No. 2, pp. 379-381, Mar. 2008.

Sakane T. et al., Current Concepts: Behcet's disease, The New England Journal of Medicine, vol. 341, No. 17, pp. 1284-1291, Oct. 21, 1999.

\* cited by examiner

Peptide sequences, Human, Mouse and Rat

```
                              :: **.:
A   IB2       :   IPSPSVEEPHKHRPTTLRL---TTLGAQDS       SEQ ID NO: 14
    IB1       :   PGTGCGDTYRPKRPTTLNLFPQVPRSQDT        SEQ ID NO: 13
    c-jun     :   GAYGYSNPKILKQSMTLNLADPVGNLKPH        SEQ ID NO: 15
    ATF2      :   TNEDHLAVHKHKHEMTLKFGPARNDSVIV        SEQ ID NO: 16

:  . .***** *      **:
B   L-IB1(s)  :   ----RPKRPTTLNLFPQVPRSQD              SEQ ID NO: 1
    L-IB1     :   DTYRPKRPTTLNLFPQVPRSQDT              SEQ ID NO: 17
                      o o o

C   L-TAT         :   NH2-GRKKRRQRRR-COOH                                      SEQ ID NO: 5
    L-TAT-IB1(s)  :   NH2-GRKKRRQRRRP----RPKRPTTLNLFPQVPRSQD-COOH              SEQ ID NO: 9
    L-TAT-IB1     :   NH2-GRKKRRQRRRPPDTYRPKRPTTLNLFPQVPRSQDT-COOH             SEQ ID NO: 23

D-TAT         :   NH2-RRRQRRKKRG-COOH                                      SEQ ID NO: 6
    D-TAT-IB1(s)  :   NH2--DQSRPVQPFLNLTPRKPR----PPRRRQRRKKRG-COOH             SEQ ID NO: 11
    D-TAT-IB1     :   NH2-TDQSRPVQPFLNLTPRKPRYTDPPRRRQRRKKRG-COOH              SEQ ID NO: 25
```

Fig. 1

Generic Sequences, Human, Mouse and Rat

| | | |
|---|---|---|
| L-generic-TAT(s) : | $NH_2-X_n^b-RKKRRQRRR-X_n^b-COOH$ | SEQ ID NO: 7 |
| L-TAT-IB (generic) (s): | $NH_2-X_n^b-RKKRRQRRR-X_n^b-X_n^a-RPTTLXLXXXXXQD-X_n^b-COOH$ | SEQ ID NO: 10 |
| L-TAT-IB (generic) : | $NH_2-XXXXXXRKKRRQRRRXXXXXXXXRPTTLXLXXXXXXQDS/TX-COOH$ | SEQ ID NO: 24 |
| D-generic-TAT(s) : | $NH_2-X_n^b-RRRQRRKKR-X_n^b-COOH$ | SEQ ID NO: 8 |
| D-TAT-IB (generic) (s): | $NH_2-X_n^b-DQXXXXXXLXLTTPR-X_n^a-X_n^b-RRRQRRKKR-X_n^b-COOH$ | SEQ ID NO: 12 |
| D-TAT-IB (generic) : | $NH_2-XT/SDQXXXXXXLXLTTPRXXXXXXXXRRRQRRKKRXXXXXX-COOH$ | SEQ ID NO: 26 |

Fig. 2

Macrophage
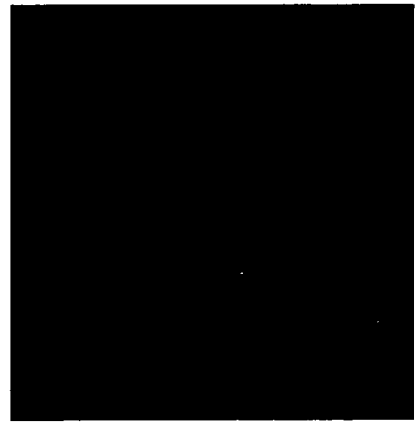
DMEM Control
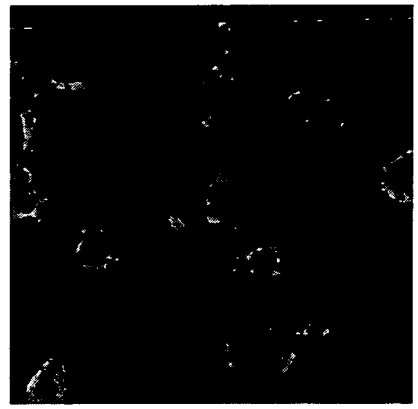
XG-102
Fig. 8

```
ccgccccagc tcagtccgaa ccccgcggcg gcggcggcct cctccacacg cctccacctc    60
cgccgccgcc gccgccgccg ccgcctcccg cgccgctctc cgcccggatg gccaggctga   120
gcccgggaat ggcggagcga gagagcggcc tgagcggggg tgccgcgtcc ccaccggccg   180
cttcccccatt cctgggactg cacatcgcgt cgcctcccaa tttcaggctc acccatgata   240
tcagcctgga ggagtttgag gatgaagacc tttcggagat cactgatgag tgtggcatca   300
gcctgcagtg caaagacacc ttgtctctcc ggcccccgcg cgccgggcta ctgtctgcgg   360
gtagcagcgg tagcgcgggg agccggctgc aggcggagat gctgcagatg gacctgatcg   420
acgcggcaag tgacactccg ggcgccgagg acgacgaaga ggacgacgac gagctcgctg   480
cccaacggcc aggagtgggg ccttccaaag ccgagtctgg ccaggagccg gcgtctcgca   540
gccagggtca gggccagggc cccggcacag gctgcggaga cacctaccgg cccaagaggc   600
ctaccacgct caacctttc ccgcaggtgc cgcggtctca ggacacgctg aataataact   660
ctttaggcaa aaagcacagt tggcaggacc gtgtgtctcg atcatcctcc cctctgaaga   720
caggggagca gacgcctcca catgaacata tctgcctgag tgatgagctg ccgccccagg   780
gcagtcctgt tcccacccag gatcgtggca cttccaccga cagcccttgt cgccgtactg   840
cagccaccca gatggcacct ccaagtggtc cccctgccac tgcacctggt ggccggggcc   900
actcccatcg agatcggtcc atatcagcag atgtgcggct cgaggcgact gaggagatct   960
acctgacccc agtgcagagg cccccagacc ctgcagaacc cacctccacc ttcttgccac  1020
ccactgagag ccggatgtct gtcagctcgg atcctgaccc tgccgcttac tctgtaactg  1080
cagggcgacc gcacccttcc atcagtgaag aggatgaggg cttcgactgt ctgtcatccc  1140
cagagcaagc tgagccacca ggtggagggt ggcggggaag cctcggggag ccaccaccgc  1200
ctccacgggc ctcactgagc tcggacacca gcgcactgtc ctacgactct gtcaagtaca  1260
cactggtggt ggatgagcat gcccagcttg agttggtgag cctgcggcca tgttttggag  1320
attacagtga cgaaagcgac tctgccactg tctatgacaa ctgtgcctct gcctcctcgc  1380
cctacgagtc agccattggt gaggaatatg aggaggcccc tcaaccccgg cctcccacct  1440
gcctgtcaga ggactccaca ccggatgagc ctgacgtcca cttctctaag aagtttctga  1500
atgtcttcat gagtggccgc tctcgttcct ccagtgccga gtcctttggg ctgttctcct  1560
gtgtcatcaa tggggaggag catgagcaaa cccatcgggc tatattcagg tttgtgcctc  1620
ggcatgaaga tgaacttgag ctggaagtgg acgaccctct gctggtggag ctgcaggcag  1680
```

Fig. 14

```
aagactattg gtatgaggcc tataacatgc gcactggagc ccgtggtgtc tttcctgcct    1740
actatgccat tgaggtcacc aaggagcctg agcacatggc agcccttgcc aaaaacagcg    1800
actggattga ccagttccgg gtgaagttcc tgggctctgt ccaggttcct tatcacaagg    1860
gcaatgatgt cctctgtgct gctatgcaaa agatcgccac cacccgccgg ctcaccgtgc    1920
actttaaccc gccctccagc tgtgtccttg aaatcagcgt tagggtgtc  aagataggtg    1980
tcaaagctga tgaagctcag gaggccaagg gaaataaatg tagccacttt ttccagctaa    2040
aaaacatctc tttctgtggg taccatccaa agaacaacaa gtactttggg tttatcacta    2100
agcaccctgc tgaccaccgg tttgcctgcc atgtctttgt gtctgaagat tccaccaaag    2160
ccctggcaga gtctgtgggg cgtgcatttc agcagttcta caagcaattt gtggaatata    2220
cctgtcctac agaagatatc tacttggagt agcagcaacc cccctctctg cagcccctca    2280
gccccaggcc agtactagga cagctgactg ctgacaggat gttgtactgc cacgagagaa    2340
tgggggagtg agggctgttg gggtcggggg gcagggggttt ggggagaggc agatgcagtt    2400
tattgtaata tatggggtta gattaatcta tggaggacag tacaggctct ctcggggctg    2460
gggaagggca gggctgggg ggggggtcagg catctggcca caaaggggtc ccctagggac    2520
agaggcgctg caccatcctg ggcttgtttc atactagagg ccctggcttt ctggctcttg    2580
ggtcctgcct tgacaaagcc cagccacctg gaagtgtcac cttcccttgt ccacctcacc    2640
cagtgccctg agctcatgct gagcccaagc acctccgaag gactttccag taaggaaatg    2700
gcaacatgtg acagtgagac cctgttctca tctgtggggc tccggcagct ccgaccccca    2760
gcctggccag cacgctgacc ctggcaagct tgtgtgttca aagaaggaga gggccacagc    2820
aagccctgcc tgccagggaa ggttccctct cagctggccc cagccaactg gtcactgtct    2880
tgtcacctgg ctactactat taaagtgcca tttcttgtct gaaaaaaaaa aaaaaaaaa    2940
aaaaaaactc gag                                                      2953
```

Fig. 14 (cont.)

Met Ala Arg Leu Ser Pro Gly Met Ala Glu Arg Glu Ser Gly Leu Ser
1                 5                  10                15

Gly Gly Ala Ala Ser Pro Pro Ala Ala Ser Pro Phe Leu Gly Leu His
            20              25               30

Ile Ala Ser Pro Pro Asn Phe Arg Leu Thr His Asp Ile Ser Leu Glu
        35              40                  45

Glu Phe Glu Asp Glu Asp Leu Ser Glu Ile Thr Asp Glu Cys Gly Ile
    50              55              60

Ser Leu Gln Cys Lys Asp Thr Leu Ser Leu Arg Pro Pro Arg Ala Gly
65              70              75              80

Leu Leu Ser Ala Gly Ser Ser Gly Ser Ala Gly Ser Arg Leu Gln Ala
            85          90              95

Glu Met Leu Gln Met Asp Leu Ile Asp Ala Ala Ser Asp Thr Pro Gly
            100             105             110

Ala Glu Asp Asp Glu Glu Asp Asp Glu Leu Ala Ala Gln Arg Pro
            115             120             125

Gly Val Gly Pro Ser Lys Ala Glu Ser Gly Gln Glu Pro Ala Ser Arg
130             135             140

Ser Gln Gly Gln Gly Gln Gly Pro Gly Thr Gly Cys Gly Asp Thr Tyr
145             150             155             160

Arg Pro Lys Arg Pro Thr Thr Leu Asn Leu Phe Pro Gln Val Pro Arg
            165             170             175

Ser Gln Asp Thr Leu Asn Asn Asn Ser Leu Gly Lys Lys His Ser Trp
            180             185             190

Gln Asp Arg Val Ser Arg Ser Ser Pro Leu Lys Thr Gly Glu Gln
        195             200             205

Thr Pro Pro His Glu His Ile Cys Leu Ser Asp Glu Leu Pro Pro Gln
    210             215             220

Gly Ser Pro Val Pro Thr Gln Asp Arg Gly Thr Ser Thr Asp Ser Pro
225             230             235             240

Cys Arg Arg Thr Ala Ala Thr Gln Met Ala Pro Pro Ser Gly Pro Pro
            245             250             255

Fig. 15

Ala Thr Ala Pro Gly Gly Arg Gly His Ser His Arg Asp Arg Ser Ile
              260              265              270

Ser Ala Asp Val Arg Leu Glu Ala Thr Glu Glu Ile Tyr Leu Thr Pro
        275              280              285

Val Gln Arg Pro Pro Asp Pro Ala Glu Pro Thr Ser Thr Phe Leu Pro
    290              295              300

Pro Thr Glu Ser Arg Met Ser Val Ser Ser Asp Pro Asp Pro Ala Ala
305              310              315              320

Tyr Ser Val Thr Ala Gly Arg Pro His Pro Ser Ile Ser Glu Glu Asp
              325              330              335

Glu Gly Phe Asp Cys Leu Ser Ser Pro Glu Gln Ala Glu Pro Pro Gly
            340              345              350

Gly Gly Trp Arg Gly Ser Leu Gly Glu Pro Pro Pro Pro Arg Ala
        355              360              365

Ser Leu Ser Ser Asp Thr Ser Ala Leu Ser Tyr Asp Ser Val Lys Tyr
370              375              380

Thr Leu Val Val Asp Glu His Ala Gln Leu Glu Leu Val Ser Leu Arg
385              390              395              400

Pro Cys Phe Gly Asp Tyr Ser Asp Glu Ser Asp Ser Ala Thr Val Tyr
            405              410              415

Asp Asn Cys Ala Ser Ala Ser Ser Pro Tyr Glu Ser Ala Ile Gly Glu
            420              425              430

Glu Tyr Glu Glu Ala Pro Gln Pro Arg Pro Pro Thr Cys Leu Ser Glu
        435              440              445

Asp Ser Thr Pro Asp Glu Pro Asp Val His Phe Ser Lys Lys Phe Leu
450              455              460

Asn Val Phe Met Ser Gly Arg Ser Arg Ser Ser Ser Ala Glu Ser Phe
465              470              475              480

Gly Leu Phe Ser Cys Val Ile Asn Gly Glu Glu His Glu Gln Thr His
            485              490              495

Arg Ala Ile Phe Arg Phe Val Pro Arg His Glu Asp Glu Leu Glu Leu
            500              505              510

Fig. 15 (cont.)

```
Glu Val Asp Asp Pro Leu Leu Val Glu Leu Gln Ala Glu Asp Tyr Trp
            515                             525

Tyr Glu Ala Tyr Asn Met Arg Thr Gly Ala Arg Gly Val Phe Pro Ala
    530                 535                 540

Tyr Tyr Ala Ile Glu Val Thr Lys Glu Pro Glu His Met Ala Ala Leu
545             550                 555                     560

Ala Lys Asn Ser Asp Trp Ile Asp Gln Phe Arg Val Lys Phe Leu Gly
                565                 570                 575

Ser Val Gln Val Pro Tyr His Lys Gly Asn Asp Val Leu Cys Ala Ala
            580                 585                 590

Met Gln Lys Ile Ala Thr Thr Arg Arg Leu Thr Val His Phe Asn Pro
        595                 600                 605

Pro Ser Ser Cys Val Leu Glu Ile Ser Val Arg Gly Val Lys Ile Gly
    610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
                645                 650                 655

Asn Lys Tyr Phe Gly Phe Ile Thr Lys His Pro Ala Asp His Arg Phe
            660                 665                 670

Ala Cys His Val Phe Val Ser Glu Asp Ser Thr Lys Ala Leu Ala Glu
        675                 680                 685

Ser Val Gly Arg Ala Phe Gln Gln Phe Tyr Lys Gln Phe Val Glu Tyr
    690                 695                 700

Thr Cys Pro Thr Glu Asp Ile Tyr Leu Glu
705                 710
```

Fig. 15 (cont.)

Met Ala Glu Arg Glu Ser Gly Gly Leu Gly Gly Gly Ala Ala Ser Pro
1           5                   10                  15

Pro Ala Ala Ser Pro Phe Leu Gly Leu His Ile Ala Ser Pro Pro Asn
            20                  25              30

Phe Arg Leu Thr His Asp Ile Ser Leu Glu Glu Phe Glu Asp Glu Asp
        35                  40                  45

Leu Ser Glu Ile Thr Asp Glu Cys Gly Ile Ser Leu Gln Cys Lys Asp
    50                  55                  60

Thr Leu Ser Leu Arg Pro Arg Ala Gly Leu Leu Ser Ala Gly Gly
65              70                  75                  80

Gly Gly Ala Gly Ser Arg Leu Gln Ala Glu Met Leu Gln Met Asp Leu
            85                  90                  95

Ile Asp Ala Thr Gly Asp Thr Pro Gly Ala Glu Asp Asp Glu Glu Asp
            100             105                 110

Asp Asp Glu Glu Arg Ala Ala Arg Arg Pro Gly Ala Gly Pro Pro Lys
        115             120                 125

Ala Glu Ser Gly Gln Glu Pro Ala Ser Arg Gly Gln Gly Gln Ser Gln
    130             135                 140

Gly Gln Ser Gln Gly Pro Gly Ser Gly Asp Thr Tyr Arg Pro Lys Arg
145             150             155                 160

Pro Thr Thr Leu Asn Leu Phe Pro Gln Val Pro Arg Ser Gln Asp Thr
            165             170                 175

Leu Asn Asn Asn Ser Leu Gly Lys Lys His Ser Trp Gln Asp Arg Val
            180             185             190

Ser Arg Ser Ser Ser Pro Leu Lys Thr Gly Glu Gln Thr Pro Pro His
    195             200             205

Glu His Ile Cys Leu Ser Asp Glu Leu Pro Pro Gln Ser Gly Pro Ala
    210             215             220

Pro Thr Thr Asp Arg Gly Thr Ser Thr Asp Ser Pro Cys Arg Arg Ser
225             230             235                 240

Thr Ala Thr Gln Met Ala Pro Pro Gly Gly Pro Pro Ala Ala Pro Pro
            245             250             255

Fig. 16

Gly Gly Arg Gly His Ser His Arg Asp Arg Ile His Tyr Gln Ala Asp
            260                 265                 270

Val Arg Leu Glu Ala Thr Glu Glu Ile Tyr Leu Thr Pro Val Gln Arg
        275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Glu Gly Phe
                325                 330                 335

Asp Cys Leu Ser Ser Pro Glu Arg Ala Glu Pro Pro Gly Gly Gly Trp
            340                 345                 350

Arg Gly Ser Leu Gly Glu Pro Pro Pro Pro Arg Ala Ser Leu Ser
        355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
            420                 425                 430

Glu Ala Pro Arg Pro Gln Pro Pro Ala Cys Leu Ser Glu Asp Ser Thr
        435                 440                 445

Pro Asp Glu Pro Asp Val His Phe Ser Lys Lys Phe Leu Asn Val Phe
    450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
                485                 490                 495

Phe Arg Phe Val Pro Arg His Glu Asp Glu Leu Glu Leu Glu Val Asp
            500                 505                 510

Fig. 16 (cont.)

Asp Pro Leu Leu Val Glu Leu Gln Ala Glu Asp Tyr Trp Tyr Glu Ala
        515                 520                 525

Tyr Asn Met Arg Thr Gly Ala Arg Gly Val Phe Pro Ala Tyr Tyr Ala
        530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
                580                 585                 590

Ile Ala Thr Thr Arg Arg Leu Thr Val His Phe Asn Pro Pro Ser Ser
        595                 600                 605

Cys Val Leu Glu Ile Ser Val Arg Gly Val Lys Ile Gly Val Lys Ala
        610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
                660                 665                 670

Val Phe Val Ser Glu Asp Ser Thr Lys Ala Leu Ala Glu Ser Val Gly
        675                 680                 685

Arg Ala Phe Gln Gln Phe Tyr Lys Gln Phe Val Glu Tyr Thr Cys Pro
        690                 695                 700

Thr Glu Asp Ile Tyr Leu Glu
705                 710

Fig. 16 (cont.)

| | | | | | |
|---|---|---|---|---|---:|
| atggcggagc | gagaaagcgg | cggcctggga | ggggggggccg | cgtccccgcc | 60 |
| | | | | cgccgcctcc | |
| ccgttcctgg | ggctgcacat | cgcttcgcct | cccaatttca | ggctcaccca | 120 |
| | | | | tgacatcagc | |
| ctggaggagt | ttgaggatga | agacctctcg | gagatcactg | atgagtgtgg | 180 |
| | | | | catcagctta | |
| cagtgcaaag | acaccctgtc | cttacggccc | ccgcgcgccg | ggctgctctc | 240 |
| | | | | tgcggcggc | |
| ggcggcgcgg | ggagccggtt | gcaggccgag | atgctgcaga | tggacctgat | 300 |
| | | | | cgacgcgacg | |
| ggggacactc | ccggggccga | ggacgacgag | gaggacgacg | acgaggagcg | 360 |
| | | | | cgcggcccgg | |
| cggccgggag | cggggccgcc | caaggccgag | tccggccagg | agccggcgtc | 420 |
| | | | | ccgcggccag | |
| ggccagagcc | aaggccagag | ccagggcccg | ggcagcgggg | acacgtaccg | 480 |
| | | | | gcccaagcgg | |
| cccaccacgc | tcaacctctt | tccgcaggtg | ccgcggtctc | aggacacact | 540 |
| | | | | gaataataat | |
| tctctgggca | aaaagcacag | ttggcaggat | cgggtgtctc | gatcatcctc | 600 |
| | | | | accctgaag | |
| acaggggagc | agacaccacc | gcatgaacac | atctgcctga | gcgatgagct | 660 |
| | | | | gccccccag | |
| agcggccccg | cccccaccac | agatcgaggc | acctccaccg | acagcccttg | 720 |
| | | | | ccgccgcagc | |
| acagccaccc | agatggcacc | tccgggtggt | cccctgctg | ccccgcctgg | 780 |
| | | | | gggtcggggc | |
| cactcgcatc | gagaccgaat | ccactaccag | gcgatgtgc | gactagaggc | 840 |
| | | | | cactgaggag | |
| atctacctga | ccccagtgca | gaggccccca | gacgctgcag | agcccacctc | 900 |
| | | | | cgccttcctg | |
| ccgcccactg | agagccggat | gtcagtcagc | tccgatccag | accctgccgc | 960 |
| | | | | ctaccccct | |
| acggcagggc | ggccgcaccc | ctccatcagt | gaagaggaag | agggcttcga | 1020 |
| | | | | ctgcctgtcg | |
| tccccagagc | gggctgagcc | cccaggcgga | gggtggcggg | ggagcctggg | 1080 |
| | | | | ggagccgccg | |
| ccacctccac | gggcctctct | gagctcggac | accagcgccc | tgtcctatga | 1140 |
| | | | | ctctgtcaag | |
| tacacgctgg | tggtagatga | gcatgcacag | ctggagctgg | tgagcctgcg | 1200 |
| | | | | gccgtgcttc | |
| ggagactaca | gtgacgagag | tgactctgcc | accgtctatg | acaactgtgc | 1260 |
| | | | | ctccgtctcc | |
| tcgccctatg | agtcggccat | cggagaggaa | tatgaggagg | ccccgcggcc | 1320 |
| | | | | ccagcccct | |
| gcctgcctct | ccgaggactc | cacgcctgat | gaacccgacg | tccatttctc | 1380 |
| | | | | caagaaattc | |
| ctgaacgtct | tcatgagtgg | ccgctcccgc | tcctccagtg | ctgagtcctt | 1440 |
| | | | | cgggctgttc | |
| tcctgcatca | tcaacgggga | ggagcaggag | cagacccacc | gggccatatt | 1500 |
| | | | | caggtttgtg | |
| cctcgacacg | aagacgaact | tgagctggaa | gtggatgacc | ctctgctagt | 1560 |
| | | | | ggagctccag | |
| gctgaagact | actggtacga | ggcctacaac | atgcgcactg | gtgcccgggg | 1620 |
| | | | | tgtctttcct | |
| gcctattacg | ccatcgaggt | caccaaggag | cccgagcaca | tggcagccct | 1680 |
| | | | | ggccaaaaac | |
| agtgactggg | tggaccagtt | ccgggtgaag | ttcctgggct | cagtccaggt | 1740 |
| | | | | tccctatcac | |

Fig. 17

```
aagggcaatg  acgtcctctg  tgctgctatg  caaaagattg  ccaccacccg  ccggctcacc     1800
gtgcacttta  acccgccctc  cagctgtgtc  ctggagatca  gcgtgcgggg  tgtgaagata     1860
ggcgtcaagg  ccgatgactc  ccaggaggcc  aagggaata   aatgtagcca  cttttttccag    1920
ttaaaaaaca  tctctttctg  cggatatcat  ccaaagaaca  acaagtactt  tgggttcatc     1980
accaagcacc  cgccgacca   ccggtttgcc  tgccacgtct  ttgtgtctga  agactccacc     2040
aaagccctgg  cagagtccgt  ggggagagca  ttccagcagt  tctacaagca  gtttgtggag     2100
tacacctgcc  ccacagaaga  tatctacctg  gagtag                                 2136
```

USE OF CELL-PERMEABLE PEPTIDE INHIBITORS OF THE JNK SIGNAL TRANSDUCTION PATHWAY FOR THE TREATMENT OF CHRONIC OR NON-CHRONIC INFLAMMATORY DIGESTIVE DISEASES

RELATED APPLICATIONS

The present application is a U.S. National Phase Application of International Application No. PCT/EP2009/003936 (filed 2 Jun. 2009) which claims priority to International Application No. PCT/EP2008/004340 (filed 30 May 2008) both of which are hereby incorporated by reference in their entirety.

SEQUENCE LISTING

A computer readable text file, entitled "067802-5028_SequenceListing.txt," created on or about Nov. 29, 2010 with a file size of about 70 kb contains the sequence listing for this application and is hereby incorporated by reference in its entirety.

The present invention refers to the use of protein kinase inhibitors and more specifically to the use of inhibitors of the protein kinase c-Jun amino terminal kinase, JNK inhibitor sequences, chimeric peptides, or of nucleic acids encoding same as well as pharmaceutical compositions containing same, for the treatment of non-chronic or chronic inflammatory digestive diseases, such as colitis, including e.g. ulcerative colitis, Crohn's colitis, diversion colitis, ischemic colitis, infectious colitis, fulminant colitis, chemical colitis, microscopic colitis, lymphocytic colitis, and atypical colitis, etc.

The number of digestive diseases, particularly of non-chronic and chronic digestive diseases has significantly increased during the last decades in Western Civilizations and represents a considerable challenge for their public health care system. Digestive diseases are diseases that pertain to the gastrointestinal tract. This includes diseases of the esophagus, stomach, first, second, third and fourth part of the duodenum, jejunum, ileum, the ileo-cecal complex, large intestine, (ascending, transverse and descending colon) sigmoid colon and rectum. Chronic inflammatory digestive diseases occur frequently and are characterized by an inflammation of the colon, such as colitis, including e.g. Colitis ulcerosa (ulcerative colitis), Morbus Crohn (Crohn's disease), diversion colitis, ischemic colitis, infectious colitis, fulminant colitis, chemical colitis, microscopic colitis, lymphocytic colitis, collageneous colitis, indeterminate colitis and atypical colitis, etc., wherein Colitis ulcerosa (ulcerative colitis) and Morbus Crohn (Crohn's disease) represent the two major chronic inflammatory digestive diseases and two major types of inflammatory bowel disease. Both, Morbus Crohn and Colitis ulcerosa, are diseases the occurrence of which has rapidly increased during last decades. E.g., in Germany it is estimated that about 0.01% to about 0.1% of the population, i.e. about 10 to 100 people from about 100.000, suffer from Morbus Crohn or Colitis ulcerosa. Furthermore, about 1 to about 8 incidences of Morbus Crohn or Colitis ulcerosa occur each year with increasing rate. Women are affected sligthly more often by Morbus Crohn and the male:female ratio of Colitis ulcerosa is about 1:1. The peak age of onset of Colitis ulcerosa and Morbus Chrohn is between 15 and 30 years. The second peak occurs between ages of 60 and 80 years.

Colitis ulcerosa is a form of inflammatory bowel disease (IBD) and, as a subtype of colitis, a disease of the intestine, specifically of the large intestine or colon. The symptoms of Colitis ulcerosa typically include characteristic ulcers or open sores in the colon. Colitis ulcerosa ususally starts in the rectum and spreads continually into the proximal sections of the large intestine or colon, wherein the upper gastrointestinal tract is normally not affected. The main symptoms of active disease is usually diarrhea mixed with blood, of gradual onset, wherein patients typically suffer from cramplike abdominal pain. Colitis ulcerosa is associated with a variety of extraintestinal manifestations (dermatologic rheumatology, ocular and others). It is an intermittent disease, with periods of exacerbated symptoms, and periods that are relatively symptom-free. Although Colitis ulcerosa has no known cause, there is a presumed genetic component to susceptibility. Furthermore, it is assumed, that the disease may be triggered in a susceptible person by environmental factors. However, the symptoms of Colitis ulcerosa rarely diminish on their own but rather require treatment to go into remission, particularly, when the disease switches into a chronic disease state.

Therapy of Colitis ulcerosa typically depends of the degree and distribution of the disease and usually involves treatment with anti-inflammatory drugs, immunosupression, and biological therapy targeting specific components of the immune response. In disease states with minor or medium inflammatory activity (mild and moderate distal colitis), typically if the disease is restricted to the rectum, a common therapy usually includes administration of 5-aminosalicylates, such as Pentasa® or Salofalk®. Alternatively, local medication using suppositories or enemas may be applied. In addition, administration of steroid containing medications including e.g. hydrocortison, Budenosid, Beclomethason (Betnesol®) or Prednison (Rectodelt®) may be used, especially in acute therapy. In disease states with high inflammatory activity, typically, if Colitis ulcerosa spreads into the proximal sections of the large intestine or colon, administration of glucocorticoides, such as Beclomethason (Betnesol®) or Prednison (Rectodelt®) or derivatives thereof, using intraveneous injection or administration in rectal or oral forms, or administration of immunosuppressiva, such as e.g. azathioprin, methothrexat (MTX) or cyclosporin A are typically used. In few cases, antibody therapy using antibodies, e.g. against TNF-alpha (INFLIXIMAB) or anti-CD4, may be applied. In cases of severe chronic disease states, which do not respond to medication therapy, a colorectomy, i.e. a partial or total removal of the large bowel through surgery, is occasionally necessary and is considered to be a cure for the disease in cases. These therapies typically decrease the symptoms of an acute attack due to Colitis ulcerosa. However, none of these therapies appears to allow effective and enduring cure of this disease.

Morbus Crohn, or Crohn's disease (also known as regional enteritis) is a further important chronic inflammatory digestive disease. It is a subtype of a chronic, episodic, inflammatory bowel disease (IBD) that affects the entire wall of the bowel and intestines. In contrast to colitis ulcerosa Morbus Crohn can affect any part of the complete gastrointestinal tract, and as a result, the symptoms of Morbus Crohn vary among afflicted individuals. The disease is characterized by areas of inflammation with areas of normal lining between in a symptom known as skip lesions. The main gastrointestinal symptoms are abdominal pain, diarrhea, constipation, vomiting and weight loss or gain. Morbus Crohn can also cause complications outside of the gastrointestinal tract such as skin rashes, arthritis, and inflammation of the eye. Morbus Crohn affects between 400,000 and 600,000 people in North America (Loftus, E. V.; P. Schoenfeld, W. J. Sandborn (January 2002). "The epidemiology and natural history of Crohn's disease in population-based patient cohorts from North America: a systematic review". *Alimentary Pharmacology & Therapeutics* 16 (1): 51-60.). Prevalence estimates for Northern Europe have ranged from 27-48 per 100,000 (Bernstein, Charles N. (July 2006). "The Epidemiology of Inflammatory Bowel Disease in Canada: A Population-Based Study". *The American Journal of Gastroenterology* 101 (7): 1559-1568). Furthermore, Morbus Crohn tends to present initially in the teens and twenties, with another peak incidence in the fifties to seventies, although the disease can occur at any age (Hanauer, Stephen B. (March 1996). "Inflammatory bowel disease". *New England Journal of Medicine* 334 (13): 841-848; Gopal, Latha; Senthil Nachimuthu (2006 May 23). Chrohns Disease, eMedicine). The cause of Morbus Crohn is not known, however, it is believed to be an autoimmune disease that is genetically linked. The highest relative risk occurs in siblings, affecting females slightly more frequently, wherein smokers are three times more likely to get Morbus Crohn. A number of medical treatments are utilized with the goal of putting and keeping the disease in remission. Such medical treatments include, inter alia, 5-aminosalicylic acid (5-ASA) formulations (Pentasa® capsules, Asacol tablets, Lialda tablets, Rowasa retention enemas), steroid medications, the administration of immunomodulators (such as e.g. azathioprine, mercaptopurine (6-MP), and methotrexate), and newer biological medications, such as anti-TNAalpha antibodies (e.g. INFLIXIMAB® and ADALIMUMAB®). Similarly as discussed above for Colitis ulcerosa these therapies typically decrease the symptoms of an acute attack due to Morbus Crohn. However, none of these therapies appears to allow effective and long lasting cure of Morbus Crohn's disease (with the exception of anti-TNF-alpha, which, however, exhibits an increased risk of side effects).

Other forms of colitis include e.g. diversion colitis, ischemic colitis, infectious colitis, fulminant colitis, chemical colitis, microscopic colitis, lymphocytic colitis, collageneous colitis, indeterminate colitis and atypical colitis, etc. However, there is no effective and long lasting cure without the risk of side effects for any of these diseases. Accordingly there exists an ongoing urgent need in the art to provide alternative or improved medicaments, which allow new and preferably improved therapies of the above diseases.

The object of the present invention is thus to provide alternative or improved therapies, which allow new and preferably improved cure of non-chronic or chronic (inflammatory) digestive diseases, such as colitis, including e.g. ulcerative colitis, Crohn's colitis, diversion colitis, ischemic colitis, infectious colitis, fulminant colitis, chemical disease, microscopic colitis, lymphocytic colitis, and atypical colitis, etc.

This object is solved by the use of a JNK inhibitor sequence comprising less than 150 amino acids in length for the preparation of a pharmaceutical composition for treating non-chronic or chronic inflammatory digestive diseases in a subject.

The term "non-chronic or chronic inflammatory digestive disease" as used herein typically denotes non-chronic or chronic inflammatory diseases that pertain to the gastrointestinal tract. This includes diseases of the esophagus, stomach, first, second, third and fourth part of the duodenum, jejunum, ileum, the ileo-cecal complex, large intestine, (ascending, transverse and descending colon) sigmoid colon and rectum. Preferably included in this respect are chronic inflammatory digestive diseases, which are characterized by an inflammation of the colon, such as colitis, including e.g. Colitis ulcerosa (ulcerative colitis), Morbus Crohn (Crohn's disease), diversion colitis, ischemic colitis, infectious colitis, fulminant colitis, chemical colitis, microscopic colitis, lymphocytic colitis, collageneous colitis, indeterminate colitis and atypical colitis, etc.

The present inventors surprisingly found, that such JNK inhibitor sequences are suitable for treating such chronic or non-chronic inflammatory digestive diseases in a subject. This was neither obvious nor suggested by the prior art, even though JNK inhibitor sequences in general have been known from the art.

JNK is the abbreviation for "c-Jun amino terminal kinase", which is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These cell surface receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well effecting programmed cell death in cells identified for destruction by the immune system. This unique property made JNK signaling a promising target for developing pharmacological intervention. However, up to now a pharmacological effect of JNK inhibitor sequences has been shown only for a limited number of diseases, including several neurological disorders such as ischemic stroke and Parkinson's disease, wherein such JNK inhibitor sequences may include upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (D-JNKI and I-JIP) (see e.g. Kuan et al., Current Drug Targets—CNS & Neurological Disorders, February 2005, vol. 4, no. 1, pp. 63-67(5)). In this context, the upstream kinase inhibitor CEP-1347 (KT7515) is a semisynthetic inhibitor of the mixed lineage kinase family. CEP-1347 (KT7515) promotes neuronal survival at dosages that inhibit activation of the c-Jun amino-terminal kinases (JNKs) in primary embryonic cultures and differentiated PC12 cells after trophic withdrawal and in mice treated with 1-methyl-4-phenyl tetrahydropyridine. Further, CEP-1347 (KT7515) was observed to promote long term-survival of cultured chick embryonic dorsal root ganglion, sympathetic, ciliary and motor neurons (see e.g. Borasio et al, Neuroreport. 9(7): 1435-1439, May 11 1998.). The small chemical JNK inhibitor SP600125 was found to reduce the levels of c-Jun phosphorylation, to protect dopaminergic neurons from apoptosis, and to partly restore the level of dopamine in MPTP-induced PD in C57BU6N mice (Wang et al., Neurosci Res. 2004 February; 48(2); 195-202). These results indicated that JNK pathway is the major mediator of the neurotoxic effects of MPTP in vivo and inhibiting JNK activity may represent a new and effective strategy to treat PD. A further example of small chemical inhibitors is the aforementioned JNK-Inhibitor AS601245. AS601245 inhibits the JNK signaling pathway and promotes cell survival after cerebral ischemia. In vivo, AS601245 provided significant protection against the delayed loss of hippocampal CA1 neurons in a gerbil model of transient global ischemia. This effect is mediated by JNK inhibition and therefore by c-Jun expression and phosphorylation (see e.g. Carboni et al., J Pharmacol Exp Ther. 2004 July; 310(1):25-32. Epub 2004 Feb. 26). However, summarizing the above, the shown pharmacological effects of those JNK inhibitor sequences only proved usability for a limited number of diseases, particularly several neurological disorders such as ischemic stroke and Parkinson's disease. Thus, it was a surprising result, that JNK inhibitor sequences may be used for the treatment of non-chronic or chronic inflammatory digestive diseases.

In the context of the present invention, a INK inhibitor sequence as defined above may be typically derived from a human or rat IB1 sequence, preferably from an amino acid sequence as defined or encoded by any of sequences according to SEQ ID NO: 102 (depicts the IB1 cDNA sequence from rat and its predicted amino acid sequence), SEQ ID NO: 103 (depicts the IB1 protein sequence from rat encoded by the exon-intron boundary of the rIB1 gene-splice donor), SEQ ID NO: 104 (depicts the IB1 protein sequence from *Homo sapiens*), or SEQ ID NO: 105 (depicts the IB1 cDNA sequence from *Homo sapiens*), more preferably from an amino acid sequence as defined or encoded by any of sequences according to SEQ ID NO: 104 (depicts the IB1 protein sequence from *Homo sapiens*), or SEQ ID NO: 105 (depicts the IB1 cDNA sequence from *Homo sapiens*), or from any fragments or variants thereof. In other words, the JNK inhibitor sequence comprises a fragment, variant, or variant of such fragment of a human or rat IB1 sequence. Human or rat IB sequences are defined or encoded, respectively, by the sequences according to SEQ ID NO: 102, SEQ ID NO: 103, SEQ ID NO: 104 or SEQ ID NO: 105.

Preferably, such a JNK inhibitor sequence as used herein comprises a total length of less than 150 amino acid residues, preferably a range of 5 to 150 amino acid residues, more preferably 10 to 100 amino acid residues, even more preferably 10 to 75 amino acid residues and most preferably a range of 10 to 50 amino acid residues, e.g. 10 to 30, 10 to 20, or 10 to 15 amino acid residues.

More preferably, such a JNK inhibitor sequence and the above ranges may be selected from any of the above mentioned sequences, even more preferably from an amino acid sequence as defined according to SEQ ID NO: 104 or as encoded by SEQ ID NO: 105, even more preferably in the region between nucleotides 420 and 980 of SEQ ID NO: 105 or amino acids 105 and 291 of SEQ ID NO: 104, and most preferably in the region between nucleotides 561 and 647 of SEQ ID NO: 105 or amino acids 152 and 180 of SEQ ID NO: 104.

According to a particular embodiment, a JNK inhibitor sequence as used herein typically binds JNK and/or inhibits the activation of at least one JNK activated transcription factor, e.g. c-Jun or ATF2 (see e.g. SEQ ID NOs: 15 and 16, respectively) or Elk1.

Likewise, the JNK inhibitor sequence as used herein preferably comprises or consists of at least one amino acid sequence according to any one of SEQ ID NOs: 1 to 4, 13 to 20 and 33 to 100, or a fragment, derivative or variant thereof. More preferably, the JNK inhibitor sequence as used herein may contain 1, 2, 3, 4 or even more copies of an amino acid sequence according to SEQ ID NOs: 1 to 4, 13 to 20 and 33 to 100, or a variant, fragment or derivative thereof. If present in more than one copy, these amino acid sequences according to SEQ ID NOs: 1 to 4, 13 to 20 and 33 to 100, or variants, fragments, or derivatives thereof as used herein may be directly linked with each other without any linker sequence or via a linker sequence comprising 1 to 10, preferably 1 to 5 amino acids. Amino acids forming the linker sequence are preferably selected from glycine or proline as amino acid residues. More preferably, these amino acid sequences according to SEQ ID NOs: 1 to 4, 13 to 20 and 33 to 100, or fragments, variants or derivatives thereof, as used herein, may be separated by each other by a hinge of two, three or more proline residues.

The JNK inhibitor sequences as used herein may be composed of L-amino acids, D-amino acids, or a combination of both. Preferably, the JNK inhibitor sequences as used herein comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK inhibitor sequences as used herein in a blockwise, a non-blockwise or in an alternate manner.

According to one preferred embodiment the JNK inhibitor sequences as used herein may be exclusively composed of L-amino acids. The JNK inhibitor sequences as used herein may then comprise or consist of at least one "native JNK inhibitor sequence" according to SEQ ID NO: 1 or 3. In this context, the term "native" or "native JNK inhibitor sequence(s)" is referred to non-altered JNK inhibitor sequences according to any of SEQ ID NOs: 1 or 3, as used herein, entirely composed of L-amino acids.

Accordingly, the JNK inhibitor sequence as used herein may comprise or consist of at least one (native) amino acid sequence NH$_2$—X$_n^b$—X$_n^a$-RPTTLXLXXXXXXXQD-X$_n^b$—COOH (L-IB generic(s)) [SEQ ID NO: 3] and/or the JNK binding domain (JBDs) of IB1 XRPTTLX-LXXXXXXXQDS/TX (L-IB (generic)) [SEQ ID NO: 19]. In this context, each X typically represents an amino acid residue, preferably selected from any (native) amino acid residue. X$_n^a$ typically represents one amino acid residue, preferably selected from any amino acid residue except serine or threonine, wherein n (the number of repetitions of X) is 0 or 1. Furthermore, each X$_n^b$ may be selected from any amino acid residue, wherein n (the number of repetitions of X) is 0-5, 5-10, 10-15, 15-20, 20-30 or more, provided that if n (the number of repetitions of X) is 0 for X$_n^a$, X$_n^b$ does preferably not comprise a serine or threonine at its C-terminus, in order to avoid a serine or threonine at this position. Preferably, X$_n^b$ represents a contiguous stretch of peptide residues derived from SEQ ID NO: 1 or 3. X$_n^a$ and X$_n^b$ may represent either D or L amino acids. Additionally, the JNK inhibitor sequence as used herein may comprise or consist of at least one (native) amino acid sequence selected from the group comprising the JNK binding domain of IB1 DTYRPKRPTTLNLFPQVPR-SQDT (L-IB1) [SEQ ID NO: 17]. More preferably, the JNK inhibitor sequence as used herein further may comprise or consist of at least one (native) amino acid sequence NH$_2$-RPKRPTTLNLFPQVPRSQD-COOH (L-IB1(s)) [SEQ ID NO: 1]. Furthermore, the JNK inhibitor sequence as used herein may comprise or consist of at least one (native) amino acid sequence selected from the group comprising the JNK binding domain of IB1 L-IB1 (s1) (NH$_2$-TLNLFPQVPR-SQD-COOH, SEQ ID NO: 33); L-IB1(s2) (NH$_2$-TTLNLF-PQVPRSQ-COOH, SEQ ID NO: 34); L-IB1(s3) (NH$_2$-PT-TLNLFPQVPRS-COOH, SEQ ID NO: 35); L-IB1(s4) (NH$_2$-RPTTLNLFPQVPR-COOH, SEQ ID NO: 36); L-IB1(s5) (NH$_2$-KRPTTLNLFPQVP-COOH, SEQ ID NO: 37); L-IB1 (s6) (NH$_2$-PKRPTTLNLFPQV-COOH, SEQ ID NO: 38); L-IB1(s7) (NH$_2$-RPKRPTTLNLFPQ-COOH, SEQ ID NO: 39); L-IB1(s8) (NH$_2$-LNLFPQVPRSQD-COOH, SEQ ID NO: 40); L-IB1(s9) (NH$_2$-TLNLFPQVPRSQ-COOH, SEQ ID NO: 41); L-IB1(s10) (NH$_2$-TTLNLFPQVPRS-COOH, SEQ ID NO: 42); L-IB1(s11) (NH$_2$-PTTLNLFPQVPR-COOH, SEQ ID NO: 43); L-IB1(s12) (NH$_2$-RPTTLNLF-PQVP-COOH, SEQ ID NO: 44); L-IB1(s13) (NH$_2$-KRPT-TLNLFPQV-COOH, SEQ ID NO: 45); L-IB1(s14) (NH$_2$-PKRPTTLNLFPQ-COOH, SEQ ID NO: 46); L-IB1(s15)

(NH$_2$-RPKRPTTLNLFP-COOH, SEQ ID NO: 47); L-IB1 (s16) (NH$_2$-NLFPQVPRSQD-COOH, SEQ ID NO: 48); L-IB1(s17) (NH$_2$-LNLFPQVPRSQ-COOH, SEQ ID NO: 49); L-IB1(s18) (NH$_2$-TLNLFPQVPRS-COOH, SEQ ID NO: 50); L-IB1(s19) (NH$_2$-TTLNLFPQVPR-COOH, SEQ ID NO: 51); L-IB1(s20) (NH$_2$-PTTLNLFPQVP-COOH, SEQ ID NO: 52); L-IB1(s21) (NH$_2$-RPTTLNLFPQV-COON, SEQ ID NO: 53); L-IB1(s22) (NH$_2$-KRPTTLNLFPQ-COOH, SEQ ID NO: 54); L-IB1(s23) (NH$_2$-PKRPTTLNLFP-COOH, SEQ ID NO: 55); L-IB1(s24) (NH$_2$-RPKRPTTLNLF-COOH, SEQ ID NO: 56); L-IB1(s25) (NH$_2$-LFPQVPRSQD-COOH, SEQ ID NO: 57); L-IB1(s26) (NH$_2$-NLFPQVPRSQ-COOH, SEQ ID NO: 58); L-IB1(s27) (NH$_2$-LNLFPQVPRS-COOH, SEQ ID NO: 59); L-IB1(s28) (NH$_2$-TLNLFPQVPR-COOH, SEQ ID NO: 60); L-IB1(s29) (NH$_2$-TTLNLFPQVP-COOH, SEQ ID NO: 61); L-IB1(s30) (NH$_2$-PTTLNLFPQV-COOH, SEQ ID NO: 62); L-IB1(s31) (NH$_2$—RPTTLNLFPQ-COOH, SEQ ID NO: 63); L-IB1 (s32) (NH$_2$-KRPTTLNLFP-COOH, SEQ ID NO: 64); L-IB1 (s33) (NH$_2$-PKRPTTLNLF-COOH, SEQ ID NO: 65); and L-IB1(s34) (NH$_2$-RPKRPTTLNL-COOH, SEQ ID NO: 66).

Additionally, the JNK inhibitor sequence as used herein may comprise or consist of at least one (native) amino acid sequence selected from the group comprising the (long) JNK binding domain (JBDs) of IB1 PGTGCGDTYRPKRPT-TLNLFPQVPRSQDT (IB1-long) [SEQ ID NO: 13], the (long) INK binding domain of IB2 IPSPSVEEPHKHRPT-TLRLTTLGAQDS (IB2-long) [SEQ ID NO: 14], the JNK binding domain of c-Jun GAYGYSNPKILKQSMTLNLAD-PVGNLKPH (c-Jun) [SEQ ID NO: 15], the JNK binding domain of ATF2 TNEDHLAVHKHKHEMTLKFG-PARNDSVIV (ATF2) [SEQ ID NO: 16] (see e.g. FIGS. 1A-1C). In this context, an alignment revealed a partially conserved 8 amino acid sequence (see e.g. FIG. 1A) and a further comparison of the JBDs of IB1 and IB2 revealed two blocks of seven and three amino acids that are highly conserved between the two sequences.

According to another preferred embodiment the JNK inhibitor sequences as used herein may be composed in part or exclusively of D-amino acids as defined above. More preferably, these JNK inhibitor sequences composed of D-amino acids are non-native D retro-inverso sequences of the above (native) JNK inhibitor sequences. The term "retro-inverso sequences" refers to an isomer of a linear peptide sequence in which the direction of the sequence is reversed and the chirality of each amino acid residue is inverted (see e.g. Jameson et al., Nature, 368, 744-746 (1994); Brady et al, Nature, 368, 692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or peptide as used according to the present invention may be converted into an D retro-inverso sequence or peptide by synthesizing a reverse of the sequence or peptide for the corresponding native L-amino acid sequence or peptide.

The D retro-inverso sequences as used herein and as defined above have a variety of useful properties. For example, D retro-inverso sequences as used herein enter cells as efficiently as L-amino acid sequences as used herein, whereas the D retro-inverso sequences as used herein are more stable than the corresponding L-amino acid sequences.

Accordingly, the JNK inhibitor sequences as used herein may comprise or consist of at least one D retro-inverso sequence according to the amino acid sequence NH$_2$—X$_n^b$-DQXXXXXXXXLXLTTPR-X$_n^a$-X$_n^b$—COOH (D-IB1 generic (s)) [SEQ ID NO: 4] and/or XS/TDQXXXXXXX-LXLTTPRX (D-IB (generic)) [SEQ ID NO: 20]. As used in this context, X, X$_n^a$ and X$_n^b$ are as defined above (preferably, representing D amino acids), wherein X$_n^b$ preferably represents a contiguous stretch of residues derived from SEQ ID NO: 2 or 4.

Additionally, the JNK inhibitor sequences as used herein may comprise or consist of at least one D retro-inverso sequence according to the amino acid sequence comprising the JNK binding domain (JBDs) of IB1 TDQSRPVQPFLN-LTTPRKPRYTD (D-IB1) [SEQ ID NO: 18]. More preferably, the JNK inhibitor sequences as used herein may comprise or consist of at least one D retro-inverso sequence according to the amino acid sequence NH$_2$-DQSRPVQP-FLNLTTPRKPR-COOH (D-IB1(s)) [SEQ ID NO: 2]. Furthermore, the JNK inhibitor sequences as used herein may comprise or consist of at least one D retro-inverso sequence according to the amino acid sequence comprising the JNK binding domain (JBDs) of IB1 D-IB1(s1) (NH$_2$-QPFLNLT-TPRKPR-COOH, SEQ ID NO: 67); D-IB1(s2) (NH$_2$-VQP-FLNLTTPRKP-COOH, SEQ ID NO: 68); D-IB1(s3) (NH$_2$-PVQPFLNLTTPRK-COOH, SEQ ID NO: 69); D-IB1(s4) (NH$_2$-RPVQPFLNLTTPR-COOH, SEQ ID NO: 70); D-IB1 (s5) (NH$_2$-SRPVQPFLNLTTP-COOH, SEQ ID NO: 71); D-IB1(s6) (NH$_2$-QSRPVQPFLNLTT-COOH, SEQ ID NO: 72); D-IB1(s7) (NH$_2$-DQSRPVQPFLNLT-COOH, SEQ ID NO: 73); D-IB1(s8) (NH$_2$—PFLNLTTPRKPR-COOH, SEQ ID NO: 74); D-IB1(s9) (NH$_2$-QPFLNLTTPRKP-COOH, SEQ ID NO: 75); D-IB1(s10) (NH$_2$-VQPFLNLTTPRK-COOH, SEQ ID NO: 76); D-IB1(s11) (NH$_2$-PVQPFLNLT-TPR-COOH, SEQ ID NO: 77); D-IB1(s12) (NH$_2$-RPVQP-FLNLTTP-COOH, SEQ ID NO: 78); D-IB1(s13) (NH$_2$-SRPVQPFLNLTT-COOH, SEQ ID NO: 79); D-IB1(s14) (NH$_2$-QSRPVQPFLNLT-COOH, SEQ ID NO: 80); D-IB1 (s15) (NH$_2$-DQSRPVQPFLNL-COOH, SEQ ID NO: 81); D-IB1(s16) (NH$_2$-FLNLTTPRKPR-COOH, SEQ ID NO: 82); D-IB1(s17) (NH$_2$-PFLNLTTPRKP-COOH, SEQ ID NO: 83); D-IB1(s18) (NH$_2$-QPFLNLTTPRK-COOH, SEQ ID NO: 84); D-IB1(s19) (NH$_2$-VQPFLNLTTPR-COON, SEQ ID NO: 85); D-IB1(s20) (NH$_2$-PVQPFLNLTTP-COON, SEQ ID NO: 86); D-IB1(s21) (NH$_2$-RPVQPFLN-LTT-COOH, SEQ ID NO: 87); D-IB1(s22) (NH$_2$-SRPVQP-FLNLT-COOH, SEQ ID NO: 88); D-IB1 (s23) (NH$_2$-QSRPVQPFLNL-COOH, SEQ ID NO: 89); D-IB1(s24) (NH$_2$-DQSRPVQPFLN-COOH, SEQ ID NO: 90); D-IB1 (s25) (NH$_2$-DQSRPVQPFL-COOH, SEQ ID NO: 91); D-IB1(s26) (NH$_2$-QSRPVQPFLN-COOH, SEQ ID NO: 92); D-IB1(s27) (NH$_2$-SRPVQPFLNL-COOH, SEQ ID NO: 93); D-IB1(s28) (NH$_2$-RPVQPFLNLT-COOH, SEQ ID NO: 94); D-IB1(s29) (NH$_2$-PVQPFLNLTT-COOH, SEQ ID NO: 95); D-IB1(s30) (NH$_2$-VQPFLNLTTP-COOH, SEQ ID NO: 96); D-IB1(s31) (NH$_2$-QPFLNLTTPR-COOH, SEQ ID NO: 97); D-IB1(s32) (NH$_2$-PFLNLTTPRK-COOH, SEQ ID NO: 98); D-IB1(s33) (NH$_2$-FLNLTTPRKP-COOH, SEQ ID NO: 99); and D-IB1(s34) (NH$_2$-LNLTTPRKPR-COOH, SEQ ID NO: 100).

The JNK inhibitor sequences as used herein and as disclosed above are presented in Table 1 (SEQ ID NO:s 1-4, 13-20 and 33-100). The table presents the name of the JNK inhibitor sequences as used herein, as well as their sequence identifier number, their length, and amino acid sequence. Furthermore, Table 1 shows sequences as well as their generic formulas, e.g. for SEQ ID NO's: 1, 2, 5, 6, 9 and 11 and SEQ ID NO's: 3, 4, 7, 8, 10 and 12, respectively. Table 1 furthermore discloses the chimeric sequences SEQ ID NOs: 9-12 and 23-32 (see below), L-IB1 sequences SEQ ID NOs: 33 to 66 and D-IB1 sequences SEQ ID NOs: 67 to 100.

TABLE 1

| SEQUENCE/PEPTIDE NAME | SEQ ID NO | AA | SEQUENCE |
|---|---|---|---|
| L-IB1(s) | 1 | 19 | RPKRPTTLNLFPQVPRSQD (NH$_2$-RPKRPTTLNLFPQVPRSQD-COOH) |
| D-IB1 (s) | 2 | 19 | DQSRPVQPFLNLTTPRKPR (NH$_2$-DQSRPVQPFLNLTTPRKPR-COOH) |
| L-IB (generic) (s) | 3 | 19 | NH$_2$-X$_n^b$-X$_n^a$-RPTTLXLXXXXXXXQD-X$_n^b$-COOH |
| D-IB (generic) (s) | 4 | 19 | NH$_2$-X$_n^b$-DQXXXXXXXLXLTTPR-X$_n^a$-X$_n^b$-COOH |
| L-TAT | 5 | 10 | GRKKRRQRRR (NH$_2$-GRKKRRQRRR-COOH) |
| D-TAT | 6 | 10 | RRRQRRKKRG (NH$_2$-RRRQRRKKRG-COOH) |
| L-generic-TAT (s) | 7 | 11 | NH$_2$-X$_n^b$-RKKRRQRRR-X$_n^b$-COOH |
| D-generic-TAT (s) | 8 | 11 | NH$_2$-X$_n^b$-RRRQRRKKR-X$_n^b$-COOH |
| L-TAT-IB1(s) | 9 | 31 | GRKKRRQRRRPPRPKRPTTLNLFPQVPRSQD (NH$_2$-GRKKRRQRRRPPRPKRPTTLNLFPQVPRSQD-COOH) |
| L-TAT-IB (generic) (s) | 10 | 29 | NH$_2$-X$_n^b$-RKKRRQRRR-X$_n^b$-X$_n^a$-RPTTLXLXXXXXXXQD-X$_n^b$-COOH |
| D-TAT-IB1(s) | 11 | 31 | DQSRPVQPFLNLTTPRKPRPPRRRQRRKKRG (NH$_2$-DQSRPVQPFLNLTTPRKPRPPRRRQRRKKRG-COOH) |
| D-TAT-IB (generic) (s) | 12 | 29 | NH$_2$-X$_n^b$-DQXXXXXXXLXLTTPR-X$_n^a$-X$_n^b$-RRRQRRKKR-X$_n^b$-COOH |
| IB1-long | 13 | 29 | PGTGCGDTYRPKRPTTLNLFPQVPRSQDT (NH$_2$-PGTGCGDTYRPKRPTTLNLFPQVPRSQDT-COOH) |
| IB2-long | 14 | 27 | IPSPSVEEPHKHRPTTLRLTTLGAQDS (NH$_2$-IPSPSVEEPHKHRPTTLRLTTLGAQDS-COOH) |
| c-Jun | 15 | 29 | GAYGYSNPKILKQSMTLNLADPVGNLKPH (NH$_2$-GAYGYSNPKILKQSMTLNLADPVGNLKPH-COOH) |
| ATF2 | 16 | 29 | TNEDHLAVHKHKHEMTLKFGPARNDSVIV (NH$_2$-TNEDHLAVHKHKHEMTLKFGPARNDSVIV-COOH) |
| L-IB1 | 17 | 23 | DTYRPKRPTTLNLFPQVPRSQDT (NH$_2$-DTYRPKRPTTLNLFPQVPRSQDT-COOH) |
| D-IB1 | 18 | 23 | TDQSRPVQPFLNLTTPRKPRYTD (NH$_2$-TDQSRPVQPFLNLTTPRKPRYTD-COOH) |
| L-IB (generic) | 19 | 19 | XRPTTLXLXXXXXXXQDS/TX (NH$_2$-XRPTTLXLXXXXXXXQDS/TX-COOH) |
| D-IB (generic) | 20 | 19 | XS/TDQXXXXXXXLXLTTPRX (NH$_2$-XS/TDQXXXXXXXLXLTTPRX-COOH) |
| L-generic-TAT | 21 | 17 | XXXXRKKRRQRRRXXXX (NH$_2$-XXXXRKKRRQRRRXXXX-COOH) |
| D-generic-TAT | 22 | 17 | XXXXRRRQRRKKRXXXX (NH$_2$-XXXXRRRQRRKKRXXXX-COOH) |
| L-TAT-IB1 | 23 | 35 | GRKKRRQRRRPPDTYRPKRPTTLNLFPQVPRSQDT (NH$_2$-GRKKRRQRRRPPDTYRPKRPTTLNLFPQVPRSQDT-COOH) |
| L-TAT-IB (generic) | 24 | 42 | XXXXXXXRKKRRQRRRXXXXXXXXRPTTLXLXXXXXXXQDS/TX (NH$_2$-XXXXXXXRKKRRQRRRXXXXXXXXRPTTLXLXXXXXXXQDS/TX-COOH) |
| D-TAT-IB1 | 25 | 35 | TDQSRPVQPFLNLTTPRKPRYTDPPRRRQRRKKRG (NH$_2$-TDQSRPVQPFLNLTTPRKPRYTDPPRRRQRRKKRG-COOH) |
| D-TAT-IB (generic) | 26 | 42 | XT/SDQXXXXXXXLXLTTPRXXXXXXXXRRRQRRKKRXXXXXXX (NH$_2$-XT/SDQXXXXXXXLXLTTPRXXXXXXXXRRRQRRKKRXXXXXXX-COOH) |

TABLE 1-continued

| SEQUENCE/PEPTIDE NAME | SEQ ID NO | AA | SEQUENCE |
|---|---|---|---|
| L-TAT-IB1(s1) | 27 | 30 | RKKRRQRRRPPRPKRPTTLNLFPQVPRSQD (NH$_2$-RKKRRQRRRPPRPKRPTTLNLFPQVPRSQD-COOH) |
| L-TAT-IB1(s2) | 28 | 30 | GRKKRRQRRRX$_n^c$RPKRPTTLNLFPQVPRSQD (NH$_2$-GRKKRRQRRRX$_n^c$RPKRPTTLNLFPQVPRSQD-COOH) |
| L-TAT-IB1(s3) | 29 | 29 | RKKRRQRRRX$_n^c$RPKRPTTLNLFPQVPRSQD (NH$_2$-RKKRRQRRRX$_n^c$RPKRPTTLNLFPQVPRSQD-COOH) |
| D-TAT-IB1(s1) | 30 | 30 | DQSRPVQPFLNLTTPRKPRPPRRRQRRKKR (NH$_2$-DQSRPVQPFLNLTTPRKPRPPRRRQRRKKR-COOH) |
| D-TAT-IB1(s2) | 31 | 30 | DQSRPVQPFLNLTTPRKPRX$_n^c$RRRQRRKKRG (NH$_2$-DQSRPVQPFLNLTTPRKPRX$_n^c$RRRQRRKKRG-COOH) |
| D-TAT-IB1(s3) | 32 | 29 | DQSRPVQPFLNLTTPRKPRX$_n^c$RRRQRRKKR (NH$_2$-DQSRPVQPFLNLTTPRKPRX$_n^c$RRRQRRKKR-COOH) |
| L-IB1(s1) | 33 | 13 | TLNLFPQVPRSQD (NH$_2$-TLNLFPQVPRSQD-COOH) |
| L-IB1(s2) | 34 | 13 | TTLNLFPQVPRSQ (NH$_2$-TTLNLFPQVPRSQ-COOH) |
| L-IB1(s3) | 35 | 13 | PTTLNLFPQVPRS (NH$_2$-PTTLNLFPQVPRS-COOH) |
| L-IB1(s4) | 36 | 13 | RPTTLNLFPQVPR (NH$_2$-RPTTLNLFPQVPR-COOH) |
| L-IB1(s5) | 37 | 13 | KRPTTLNLFPQVP (NH$_2$-KRPTTLNLFPQVP-COOH) |
| L-IB1(s6) | 38 | 13 | PKRPTTLNLFPQV (NH$_2$-PKRPTTLNLFPQV-COOH) |
| L-IB1(s7) | 39 | 13 | RPKRPTTLNLFPQ (NH$_2$-RPKRPTTLNLFPQ-COOH) |
| L-IB1(s8) | 40 | 12 | LNLFPQVPRSQD (NH$_2$-LNLFPQVPRSQD-COOH) |
| L-IB1(s9) | 41 | 12 | TLNLFPQVPRSQ (NH$_2$-TLNLFPQVPRSQ-COOH) |
| L-IB1(s10) | 42 | 12 | TTLNLFPQVPRS (NH$_2$-TTLNLFPQVPRS-COOH) |
| L-IB1(s11) | 43 | 12 | PTTLNLFPQVPR (NH$_2$-PTTLNLFPQVPR-COOH) |
| L-IB1(s12) | 44 | 12 | RPTTLNLFPQVP (NH$_2$-RPTTLNLFPQVP-COOH) |
| L-IB1(s13) | 45 | 12 | KRPTTLNLFPQV (NH$_2$-KRPTTLNLFPQV-COOH) |
| L-IB1(s14) | 46 | 12 | PKRPTTLNLFPQ (NH$_2$-PKRPTTLNLFPQ-COOH) |
| L-IB1(s15) | 47 | 12 | RPKRPTTLNLFP (NH$_2$-RPKRPTTLNLFP-COOH) |
| L-IB1(s16) | 48 | 11 | NLFPQVPRSQD (NH$_2$-NLFPQVPRSQD-COOH) |
| L-IB1(s17) | 49 | 11 | LNLFPQVPRSQ (NH$_2$-LNLFPQVPRSQ-COOH) |
| L-IB1(s18) | 50 | 11 | TLNLFPQVPRS (NH$_2$-TLNLFPQVPRS-COOH) |
| L-IB1(s19) | 51 | 11 | TTLNLFPQVPR (NH$_2$-TTLNLFPQVPR-COOH) |

TABLE 1-continued

| SEQUENCE/PEPTIDE NAME | SEQ ID NO | AA | SEQUENCE |
|---|---|---|---|
| L-IB1(s20) | 52 | 11 | PTTLNLFPQVP (NH$_2$-PTTLNLFPQVP-COOH) |
| L-IB1(s21) | 53 | 11 | RPTTLNLFPQV (NH$_2$-RPTTLNLFPQV-COOH) |
| L-IB1(s22) | 54 | 11 | KRPTTLNLFPQ (NH$_2$-KRPTTLNLFPQ-COOH) |
| L-IB1(s23) | 55 | 11 | PKRPTTLNLFP (NH$_2$-PKRPTTLNLFP-COOH) |
| L-IB1(s24) | 56 | 11 | RPKRPTTLNLF (NH$_2$-RPKRPTTLNLF-COOH) |
| L-IB1(s25) | 57 | 10 | LFPQVPRSQD (NH$_2$-LFPQVPRSQD-COOH) |
| L-IB1(s26) | 58 | 10 | NLFPQVPRSQ (NH$_2$-NLFPQVPRSQ-COOH) |
| L-IB1(s27) | 59 | 10 | LNLFPQVPRS (NH$_2$-LNLFPQVPRS-COOH) |
| L-IB1(s28) | 60 | 10 | TLNLFPQVPR (NH$_2$-TLNLFPQVPR-COOH) |
| L-IB1(s29) | 61 | 10 | TTLNLFPQVP (NH$_2$-TTLNLFPQVP-COOH) |
| L-IB1(s30) | 62 | 10 | PTTLNLFPQV (NH$_2$-PTTLNLFPQV-COOH) |
| L-IB1(s31) | 63 | 10 | RPTTLNLFPQ (NH$_2$-RPTTLNLFPQ-COOH) |
| L-IB1(s32) | 64 | 10 | KRPTTLNLFP (NH$_2$-KRPTTLNLFP-COOH) |
| L-IB1(s33) | 65 | 10 | PKRPTTLNLF (NH$_2$-PKRPTTLNLF-COOH) |
| L-IB1(s34) | 66 | 10 | RPKRPTTLNL (NH$_2$-RPKRPTTLNL-COOH) |
| D-IB1(s1) | 67 | 13 | QPFLNLTTPRKPR (NH$_2$-QPFLNLTTPRKPR-COOH) |
| D-IB1(s2) | 68 | 13 | VQPFLNLTTPRKP (NH$_2$-VQPFLNLTTPRKP-COOH) |
| D-IB1(s3) | 69 | 13 | PVQPFLNLTTPRK (NH$_2$-PVQPFLNLTTPRK-COOH) |
| D-IB1(s4) | 70 | 13 | RPVQPFLNLTTPR (NH$_2$-RPVQPFLNLTTPR-COOH) |
| D-IB1(s5) | 71 | 13 | SRPVQPFLNLTTP (NH$_2$-SRPVQPFLNLTTP-COOH) |
| D-IB1(s6) | 72 | 13 | QSRPVQPFLNLTT (NH$_2$-QSRPVQPFLNLTT-COOH) |
| D-IB1(s7) | 73 | 13 | DQSRPVQPFLNLT (NH$_2$-DQSRPVQPFLNLT-COOH) |
| D-IB1(s8) | 74 | 12 | PFLNLTTPRKPR (NH$_2$-PFLNLTTPRKPR-COOH) |
| D-IB1(s9) | 75 | 12 | QPFLNLTTPRKP (NH$_2$-QPFLNLTTPRKP-COOH) |
| D-IB1(s10) | 76 | 12 | VQPFLNLTTPRK (NH$_2$-VQPFLNLTTPRK-COOH) |

TABLE 1-continued

| SEQUENCE/PEPTIDE NAME | SEQ ID NO | AA | SEQUENCE |
|---|---|---|---|
| D-IB1(s11) | 77 | 12 | PVQPFLNLTTPR (NH$_2$-PVQPFLNLTTPR-COOH) |
| D-IB1(s12) | 78 | 12 | RPVQPFLNLTTP (NH$_2$-RPVQPFLNLTTP-COOH) |
| D-IB1(s13) | 79 | 12 | SRPVQPFLNLTT (NH$_2$-SRPVQPFLNLTT-COOH) |
| D-IB1(s14) | 80 | 12 | QSRPVQPFLNLT (NH$_2$-QSRPVQPFLNLT-COOH) |
| D-IB1(s15) | 81 | 12 | DQSRPVQPFLNL (NH$_2$-DQSRPVQPFLNL-COOH) |
| D-IB1(s16) | 82 | 11 | FLNLTTPRKPR (NH$_2$-FLNLTTPRKPR-COOH) |
| D-IB1(s17) | 83 | 11 | PFLNLTTPRKP (NH$_2$-PFLNLTTPRKP-COOH) |
| D-IB1(s18) | 84 | 11 | QPFLNLTTPRK (NH$_2$-QPFLNLTTPRK-COOH) |
| D-IB1(s19) | 85 | 11 | VQPFLNLTTPR (NH$_2$-VQPFLNLTTPR-COOH) |
| D-IB1(s20) | 86 | 11 | PVQPFLNLTTP (NH$_2$-PVQPFLNLTTP-COOH) |
| D-IB1(s21) | 87 | 11 | RPVQPFLNLTT (NH$_2$-RPVQPFLNLTT-COOH) |
| D-IB1(s22) | 88 | 11 | SRPVQPFLNLT (NH$_2$-SRPVQPFLNLT-COOH) |
| D-IB1(s23) | 89 | 11 | QSRPVQPFLNL (NH$_2$-QSRPVQPFLNL-COOH) |
| D-IB1(s24) | 90 | 11 | DQSRPVQPFLN (NH$_2$-DQSRPVQPFLN-COOH) |
| D-IB1(s25) | 91 | 10 | DQSRPVQPFL (NH$_2$-DQSRPVQPFL-COOH) |
| D-IB1(s26) | 92 | 10 | QSRPVQPFLN (NH$_2$-QSRPVQPFLN-COOH) |
| D-IB1(s27) | 93 | 10 | SRPVQPFLNL (NH$_2$-SRPVQPFLNL-COOH) |
| D-IB1(s28) | 94 | 10 | RPVQPFLNLT (NH$_2$-RPVQPFLNLT-COOH) |
| D-IB1(s29) | 95 | 10 | PVQPFLNLTT (NH$_2$-PVQPFLNLTT-COOH) |
| D-IB1(s30) | 96 | 10 | VQPFLNLTTP (NH$_2$-VQPFLNLTTP-COOH) |
| D-IB1(s31) | 97 | 10 | QPFLNLTTPR (NH$_2$-QPFLNLTTPR-COOH) |
| D-IB1(s32) | 98 | 10 | PFLNLTTPRK (NH$_2$-PFLNLTTPRK-COOH) |
| D-IB1(s33) | 99 | 10 | FLNLTTPRKP (NH$_2$-FLNLTTPRKP-COOH) |
| D-IB1(s34) | 100 | 10 | LNLTTPRKPR (NH$_2$-LNLTTPRKPR-COOH) |

According to another preferred embodiment, the JNK inhibitor sequence as used herein comprises or consists of at least one variant, fragment and/or derivative of the above defined native or non-native amino acid sequences according to SEQ ID NOs: 1-4, 13-20 and 33-100. Preferably, these variants, fragments and/or derivatives retain biological activity of the above disclosed native or non-native JNK inhibitor sequences as used herein, particularly of native or non-native amino acid sequences according to SEQ ID NOs: 1-4, 13-20 and 33-100, i.e. binding JNK and/or inhibiting the activation of at least one JNK activated transcription factor, e.g. c-Jun, ATF2 or Elk1. Functionality may be tested by various tests, e.g. binding tests of the peptide to its target molecule or by biophysical methods, e.g. spectroscopy, computer modeling, structural analysis, etc. Particularly, an JNK inhibitor sequence or variants, fragments and/or derivatives thereof as defined above may be analyzed by hydrophilicity analysis (see e.g. Hopp and Woods, 1981. Proc Natl Acad Sci USA 78: 3824-3828) that can be utilized to identify the hydrophobic and hydrophilic regions of the peptides, thus aiding in the design of substrates for experimental manipulation, such as in binding experiments, or for antibody synthesis. Secondary structural analysis may also be performed to identify regions of an JNK inhibitor sequence or of variants, fragments and/or derivatives thereof as used herein that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, 1. Wiley and Sons, New York, N.Y.) and computer modeling (see e.g. Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

Accordingly, the INK inhibitor sequence as used herein may comprise or consist of at least one variant of (native or non-native) amino acid sequences according to SEQ ID NOs: 1-4, 13-20 and 33-100. In the context of the present invention, a "variant of a (native or non-native) amino acid sequence according to SEQ ID NOs: 1-4, 13-20 and 33-100" is preferably a sequence derived from any of the sequences according to SEQ ID NOs: 1-4, 13-20 and 33-100, wherein the variant comprises amino acid alterations of the amino acid sequences according to SEQ ID NOs: 1-4, 13-20 and 33-100. Such alterations typically comprise 1 to 20, preferably 1 to 10 and more preferably 1 to 5 substitutions, additions and/or deletions of amino acids according to SEQ ID NOs: 1-4, 13-20 and 33-100, wherein the variant exhibits a sequence identity with any of the sequences according to SEQ ID NOs: 1-4, 13-20 and 33-100 of at least about 30%, 50%, 70%, 80%, 90%, 95%, 98% or even 99%.

If variants of (native or non-native) amino acid sequences according to SEQ ID NOs: 1-4, 13-20 and 33-100 as defined above and used herein are obtained by substitution of specific amino acids, such substitutions preferably comprise conservative amino acid substitutions. Conservative amino acid substitutions may include synonymous amino acid residues within a group which have sufficiently similar physicochemical properties, so that a substitution between members of the group will preserve the biological activity of the molecule (see e.g. Grantham, R. (1974), Science 185, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Moreover, substitutions shall be avoided in variants as used herein, which lead to additional threonines at amino acid positions which are accessible for a phosphorylase, preferably a kinase, in order to avoid inactivation of the JNK-inhibitor sequence as used herein or of the chimeric peptide as used herein in vivo or in vitro.

Preferably, synonymous amino acid residues, which are classified into the same groups and are typically exchangeable by conservative amino acid substitutions, are defined in Table 2.

TABLE 2

Preferred Groups of Synonymous Amino Acid Residues

| Amino Acid | Synonymous Residue |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

A specific form of a variant of SEQ ID NOs: 1-4, 13-20 and 33-100 as used herein is a fragment of the (native or non-native) amino acid sequences according to SEQ ID NOs: 1, 1-4, 13-20 and 33-100" as used herein, which is typically altered by at least one deletion as compared to SEQ ID NOs 1-4, 13-20 and 33-100. Preferably, a fragment comprises at least 4 contiguous amino acids of any of SEQ ID NOs: 1-4, 13-20 and 33-100, a length typically sufficient to allow for specific recognition of an epitope from any of these sequences. Even more preferably, the fragment comprises 4 to 18, 4 to 15, or most preferably 4 to 10 contiguous amino acids of any of SEQ ID NOs: 1-4, 13-20 and 33-100, wherein the lower limit of the range may be 4, or 5, 6, 7, 8, 9, or 10. Deleted amino acids may occur at any position of SEQ ID NOs: 1-4, 13-20 and 33-100, preferably N- or C-terminally.

Furthermore, a fragment of the (native or non-native) amino acid sequences according to SEQ ID NOs: 1-4, 13-20 and 33-100, as described above, may be defined as a sequence sharing a sequence identity with any of the sequences according to SEQ ID NOs: 1-4, 13-20 and 33-100 as used herein of at least about 30%, 50%, 70%, 80%, 90%, 95%, 98%, or even 99%.

The JNK inhibitor sequences as used herein may further comprise or consist of at least one derivative of (native or non-native) amino acid sequences according to SEQ ID NOs: 1-4, 13-20 and 33-100 as defined above. In this context, a "derivative of an (native or non-native) amino acid sequence according to SEQ ID NOs: 1-4, 13-20 and 33-100" is preferably an amino acid sequence derived from any of the sequences according to SEQ ID NOs: 1-4, 13-20 and 33-100, wherein the derivative comprises at least one modified L- or D-amino acid (forming non-natural amino acid(s)), preferably 1 to 20, more preferably 1 to 10, and even more preferably 1 to 5 modified L- or D-amino acids. Derivatives of variants or fragments also fall under the scope of the present invention.

"A modified amino acid" in this respect may be any amino acid which is altered e.g. by different glycosylation in various organisms, by phosphorylation or by labeling specific amino acids. Such a label is then typically selected from the group of labels comprising:
(i) radioactive labels, i.e. radioactive phosphorylation or a radioactive label with sulphur, hydrogen, carbon, nitrogen, etc.;
(ii) colored dyes (e.g. digoxygenin, etc.);
(iii) fluorescent groups (e.g. fluorescein, etc.);
(iv) chemoluminescent groups;
(v) groups for immobilization on a solid phase (e.g. His-tag, biotin, strep-tag, flag-tag, antibodies, antigen, etc.); and
(vi) a combination of labels of two or more of the labels mentioned under (i) to (v).

In the above context, an amino acid sequence having a sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted.

For sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences, particularly as used herein, are well known in the art. Thus for instance, programs available in the Wisconsin Sequence Analysis Package, version 9.1 (Devereux et at, 1984, Nucleic Acids Res. 12, 387-395.), for example the programs BESTFIT and GAP, may be used to determine the % identity between two polynucleotides and the % identity and the % homology between two polypeptide sequences. BESTFIT uses the "local homology" algorithm of (Smith and Waterman (1981), J. Mol. Biol. 147, 195-197.) and finds the best single region of similarity between two sequences. Other programs for determining identity and/or similarity between sequences are also known in the art, for instance the BLAST family of programs (Altschul et at, 1990, J. Mol. Biol. 215, 403-410), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S. A 85, 2444-2448.).

JNK-inhibitor sequences as used according to the present invention and as defined above may be obtained or produced by methods well-known in the art, e.g. by chemical synthesis or by genetic engineering methods as discussed below. For example, a peptide corresponding to a portion of an JNK inhibitor sequence as used herein including a desired region of said JNK inhibitor sequence, or that mediates the desired activity in vitro or in vivo, may be synthesized by use of a peptide synthesizer.

JNK inhibitor sequence as used herein and as defined above, may be furthermore be modified by a trafficking sequence, allowing the JNK inhibitor sequence as used herein and as defined above to be transported effectively into the cells. Such modified JNK inhibitor sequence are preferably provided and used as chimeric sequences.

According to a second aspect the present invention therefore provides the use of a chimeric peptide including at least one first domain and at least one second domain, for the preparation of a pharmaceutical composition for treating non-chronic or chronic inflammatory digestive diseases in a subject, wherein the first domain of the chimeric peptide comprises a trafficking sequence, while the second domain of the chimeric peptide comprises an JNK inhibitor sequence as defined above, preferably of any of sequences according to SEQ ID NO: 1-4, 13-20 and 33-100 or a derivative or a fragment thereof.

Typically, chimeric peptides as used according to the present invention have a length of at least 25 amino acid residues, e.g. 25 to 250 amino acid residues, more preferably 25 to 200 amino acid residues, even more preferably 25 to 150 amino acid residues, 25 to 100 and most preferably amino acid 25 to 50 amino acid residues.

As a first domain the chimeric peptide as used herein preferably comprises a trafficking sequence, which is typically selected from any sequence of amino acids that directs a peptide (in which it is present) to a desired cellular destination. Thus, the trafficking sequence, as used herein, typically directs the peptide across the plasma membrane, e.g. from outside the cell, through the plasma membrane, and into the cytoplasm. Alternatively, or in addition, the trafficking sequence may direct the peptide to a desired location within the cell, e.g. the nucleus, the ribosome, the endoplasmic reticulum (ER), a lysosome, or peroxisome, by e.g. combining two components (e.g. a component for cell permeability and a component for nuclear location) or by one single component having e.g. properties of cell membrane transport and targeted e.g. intranuclear transport. The trafficking sequence may additionally comprise another component, which is capable of binding a cytoplasmic component or any other component or compartment of the cell (e.g. endoplasmic reticulum, mitochondria, gloom apparatus, lysosomal vesicles). Accordingly, e.g. the trafficking sequence of the first domain and the JNK inhibitor sequence of the second domain may be localized in the cytoplasm or any other compartment of the cell. This allows to determine localization of the chimeric peptide in the cell upon uptake.

Preferably, the trafficking sequence (being included in the first domain of the chimeric peptide as used herein) has a length of 5 to 150 amino acid sequences, more preferably a length of 5 to 100 and most preferably a length of from 5 to 50, 5 to 30 or even 5 to 15 amino acids.

More preferably, the trafficking sequence (contained in the first domain of the chimeric peptide as used herein) may occur as a continuous amino acid sequence stretch in the first domain. Alternatively, the trafficking sequence in the first domain may be splitted into two or more fragments, wherein all of these fragments resemble the entire trafficking sequence and may be separated from each other by 1 to 10, preferably 1 to 5 amino acids, provided that the trafficking sequence as such retains its carrier properties as disclosed above. These amino acids separating the fragments of the trafficking sequence may e.g. be selected from amino acid sequences differing from the trafficking sequence. Alternatively, the first domain may contain a trafficking sequence composed of more than one component, each component with its own function for the transport of the cargo JNK inhibitor sequence of the second domain to e.g. a specific cell compartment.

The trafficking sequence as defined above may be composed of L-amino acids, D-amino acids, or a combination of both. Preferably, the trafficking sequences (being included in the first domain of the chimeric peptide as used herein) may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK trafficking sequences in a blockwise, a non-blockwise or in an alternate manner.

According to one alternative embodiment, the trafficking sequence of the chimeric peptide as used herein may be exclusively composed of L-amino acids. More preferably, the trafficking sequence of the chimeric peptide as used herein comprises or consists of at least one "native" trafficking sequence as defined above. In this context, the term "native" is referred to non-altered trafficking sequences, entirely composed of L-amino acids.

According to another alternative embodiment the trafficking sequence of the chimeric peptide as used herein may be exclusively composed of D-amino acids. More preferably, the trafficking sequence of the chimeric peptide as used herein may comprise a D retro-inverso peptide of the sequences as presented above.

The trafficking sequence of the first domain of the chimeric peptide as used herein may be obtained from naturally occurring sources or can be produced by using genetic engineering techniques or chemical synthesis (see e.g. Sambrook, J., Fritsch, E. F., Maniatis, T. (1989) Molecular cloning: A laboratory manual. 2nd edition. Cold Spring Harbor Laboratory Press, Cold Spring Harbor, N.Y.).

Sources for the trafficking sequence of the first domain may be employed including, e.g. native proteins such as e.g. the TAT protein (e.g. as described in U.S. Pat. Nos. 5,804,604 and 5,674,980, each of these references being incorporated herein by reference), VP22 (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), trafficking sequences derived from Antennapedia (e.g. the antennapedia carrier sequence) or from basic peptides, e.g. peptides having a length of 5 to 15 amino acids, preferably 10 to 12 amino acids and comprising at least 80%, more preferably 85% or even 90% basic amino acids, such as e.g. arginine, lysine and/or histidine. Furthermore, variants, fragments and derivatives of one of the native proteins used as trafficking sequences are disclosed herewith. With regard to variants, fragments and derivatives it is referred to the definition given above for JNK inhibitor sequences as used herein. Variants, fragments as well as derivatives are correspondingly defined as set forth above for JNK inhibitor sequences as used herein. Particularly, in the context of the trafficking sequence, a variant or fragment or derivative may be defined as a sequence sharing a sequence identity with one of the native proteins used as trafficking sequences as defined above of at least about 30%, 50%, 70%, 80%, 90%, 95%, 98%, or even 99%.

In a preferred embodiment of the chimeric peptide as used herein, the trafficking sequence of the first domain comprises or consists of a sequence derived from the human immunodeficiency virus (HIV)1 TAT protein, particularly some or all of the 86 amino acids that make up the TAT protein.

For a trafficking sequence (being included in the first domain of the chimeric peptide as used herein), partial sequences of the full-length TAT protein may be used forming a functionally effective fragment of a TAT protein, i.e. a TAT peptide that includes the region that mediates entry and uptake into cells. As to whether such a sequence is a functionally effective fragment of the TAT protein can be determined using known techniques (see e.g. Franked et al, Proc. Natl. Acad. Sci, USA 86: 7397-7401 (1989)). Thus, the trafficking sequence in the first domain of the chimeric peptide as used herein may be derived from a functionally effective fragment or portion of a TAT protein sequence that comprises less than 86 amino acids, and which exhibits uptake into cells, and optionally the uptake into the cell nucleus. More preferably, partial sequences (fragments) of TAT to be used as carrier to mediate permeation of the chimeric peptide across the cell membrane, are intended to comprise the basic region (amino acids 48 to 57 or 49 to 57) of full-length TAT.

According to a more preferred embodiment, the trafficking sequence (being included in the first domain of the chimeric peptide as used herein) may comprise or consist of an amino acid sequence containing TAT residues 48-57 or 49 to 57, most preferably a generic TAT sequence $NH_2$—$X_n^b$-RKKRRQRRR-$X_n^b$—COOH (L-generic-TAT (s)) [SEQ ID NO: 7] and/or XXXXRKKRRQ RRRXXXX (L-generic-TAT) [SEQ ID NO: 21], wherein X or $X_n^b$ is as defined above. Furthermore, the number of "$X_n^b$" residues in SEQ ID NOs:8 is not limited to the one depicted, and may vary as described above. Alternatively, the trafficking sequence being included in the first domain of the chimeric peptide as used herein may comprise or consist of a peptide containing e.g. the amino acid sequence $NH_2$-GRKKRRQRRR-COOH (L-TAT) [SEQ ID NO: 5].

According to another more preferred embodiment the trafficking sequence (being included in the first domain of the chimeric peptide as used herein) may comprise a D retro-inverso peptide of the sequences as presented above, i.e. the D retro-inverso sequence of the generic TAT sequence having the sequence $NH_2$—$X_n^b$-RRRQRRKKR-$X_n^b$—COOH (D-generic-TAT (s)) [SEQ ID NO: 8] and/or XXXXRRRQR-RKKRXXXX (D-generic-TAT) [SEQ ID NO: 22]. Also here, $X_n^b$ is as defined above (preferably representing D amino acids). Furthermore, the number of "$X_n^b$" residues in SEQ ID NOs:8 is not limited to the one depicted, and may vary as described above. Most preferably, the trafficking sequence as used herein may comprise the D retro-inverso sequence $NH_2$-RRRQRRKKRG-COOH (D-TAT) [SEQ ID NO: 6].

According to another embodiment the trafficking sequence being included in the first domain of the chimeric peptide as used herein may comprise or consist of variants of the trafficking sequences as defined above. A "variant of a trafficking sequence" is preferably a sequence derived from a trafficking sequence as defined above, wherein the variant comprises a modification, for example, addition, (internal) deletion (leading to fragments) and/or substitution of at least one amino acid present in the trafficking sequence as defined above. Such (a) modification(s) typically comprise(s) 1 to 20, preferably 1 to 10 and more preferably 1 to 5 substitutions, additions and/or deletions of amino acids. Furthermore, the variant preferably exhibits a sequence identity with the trafficking sequence as defined above, more preferably with any of SEQ ID NOs: 5 to 8 or 21-22, of at least about 30%, 50%, 70%, 80%, 90%, 95%, 98% or even 99%.

Preferably, such a modification of the trafficking sequence being included in the first domain of the chimeric peptide as used herein leads to a trafficking sequence with increased or decreased stability. Alternatively, variants of the trafficking sequence can be designed to modulate intracellular localization of the chimeric peptide as used herein. When added exogenously, such variants as defined above are typically designed such that the ability of the trafficking sequence to enter cells is retained (i.e. the uptake of the variant of the trafficking sequence into the cell is substantially similar to that of the native protein used a trafficking sequence). For example, alteration of the basic region thought to be important for nuclear localization (see e.g. Dang and Lee, J. Biol. Chem. 264: 18019-18023 (1989); Hauber et al, J. Virol. 63: 1181-1187 (1989); et al., J. Virol. 63: 1-8 (1989)) can result in a cytoplasmic location or partially cytoplasmic location of the trafficking sequence, and therefore, of the JNK inhibitor sequence as component of the chimeric peptide as used herein. Additional to the above, further modifications may be introduced into the variant, e.g. by linking e.g. cholesterol or other lipid moieties to the trafficking sequence to produce a trafficking sequence having increased membrane solubility. Any of the above disclosed variants of the trafficking sequences being included in the first domain of the chimeric peptide as used herein can be produced using techniques typically known to a skilled person (see e.g. Sambrook, J., Fritsch, E. F., Maniatis, T. (1989) Molecular cloning: A laboratory manual. 2nd edition. Cold Spring Harbor Laboratory, Cold Spring Harbor, N.Y.)

As a second domain the chimeric peptide as used herein typically comprises an JNK inhibitor sequence, selected from any of the JNK inhibitor sequences as defined above, including variants, fragments and/or derivatives of these JNK inhibitor sequences.

Both domains, i.e. the first and the second domain(s), of the chimeric peptide as used herein, may be linked such as to form a functional unit. Any method for linking the first and second domain(s) as generally known in the art may be applied.

According to one embodiment, the first and the second domain(s) of the chimeric peptide as used herein are preferably linked by a covalent bond. A covalent bond, as defined herein, may be e.g. a peptide bond, which may be obtained by expressing the chimeric peptide as defined above as a fusion protein. Fusion proteins, as described herein, can be formed and used in ways analogous to or readily adaptable from standard recombinant DNA techniques, as described below. However, both domains may also be linked via side chains or may be linked by a chemical linker moiety.

The first and/or second domains of the chimeric peptide as used herein may occur in one or more copies in said chimeric peptide. If both domains are present in a single copy, the first domain may be linked either to the N-terminal or the C-terminal end of the second domain. If present in multiple copies, the first and second domain(s) may be arranged in any possible order. E.g. the first domain can be present in the chimeric peptide as used herein in a multiple copy number, e.g. in two, three or more copies, which are preferably arranged in consecutive order. Then, the second domain may be present in a single copy occurring at the N- or C-terminus of the sequence comprising the first domain. Alternatively, the second domain may be present in a multiple copy number, e.g. in two, three or more copies, and the first domain may be present in a single copy. According to both alternatives, first and second domain(s) can take any place in a consecutive arrangement. Exemplary arrangements are shown in the following: e.g. first domain-first domain-first domain-second domain; first domain-first domain-second domain-first domain; first domain-second domain-first domain-first domain; or e.g. second domain-first domain-first domain-first domain. It is well understood for a skilled person that these examples are for illustration purposes only and shall not limit the scope of the invention thereto. Thus, the number of copies and the arrangement may be varied as defined initially.

Preferably, the first and second domain(s) may be directly linked with each other without any linker. Alternatively, they may be linked with each other via a linker sequence comprising 1 to 10, preferably 1 to 5 amino acids. Amino acids forming the linker sequence are preferably selected from glycine or proline as amino acid residues. More preferably, the first and second domain(s) may be separated by each other by a hinge of two, three or more proline residues between the first and second domain(s).

The chimeric peptide as defined above and as used herein, comprising at least one first and at least one second domain, may be composed of L-amino acids, D-amino acids, or a combination of both. Therein, each domain (as well as the linkers used) may be composed of L-amino acids, D-amino acids, or a combination of both (e.g. D-TAT and L-IB1(s) or L-TAT and D-IB1(s), etc.). Preferably, the chimeric peptide as used herein may comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the chimeric peptide as used herein in a blockwise, a non-blockwise or in an alternate manner.

According to a specific embodiment the chimeric peptide as used herein comprises or consists of the L-amino acid chimeric peptides according to the generic L-TAT-IB peptide $NH_2$—$X_n^b$-RKKRRQRRR-$X_n^b$—$X_n^a$-RPTTLX-LXXXXXXXQD-$X_n^b$—COOH (L-TAT-IB (generic) (s)) [SEQ ID NO: 10], wherein X, $X_n^a$ and $X_n^b$ are preferably as defined above. More preferably, the chimeric peptide as used herein comprises or consists of the L-amino acid chimeric peptide $NH_2$-GRKKRRQRRRPPPRPKRPTTLNLFPQVPR-SQD-COOH (L-TAT-IB1 (s)) [SEQ ID NO: 9]. Alternatively or additionally, the chimeric peptide as used herein comprises or consists of the L-amino acid chimeric peptide sequence GRKKRRQRRR PPDTYRPKRP TTLNLFPQVP RSQDT (L-TAT-IB1) [SEQ ID NO: 23], or XXXXXXXXRKK RRQR-RRXXXX XXXXRPTTLX LXXXXXXXQD STTX (L-TAT-IB generic) [SEQ ID NO: 24], wherein X is preferably also as defined above, or the chimeric peptide as used herein comprises or consists of the L-amino acid chimeric peptide sequence RKKRRQRRRPPPRPKRPTTLNLF-PQVPRSQD (L-TAT-IB1(s1)) [SEQ ID NO: 27], GRKKRRQRRR$X_n^a$RPKRPTTLNLFPQVPRSQD (L-TAT-IB1(s2)) [SEQ ID NO: 28], or RKKRRQRRR$X_n^a$RPKRPT-TLNLFPQVPRSQD (L-TAT-IB1(s3)) [SEQ ID NO: 29]. In this context, each X typically represents an amino acid residue as defined above, more preferably $X_n^c$ represents a contiguous stretch of peptide residues, each X independently selected from each other from glycine or proline, e.g. a monotonic glycine stretch or a monotonic proline stretch, wherein n (the number of repetitions of $X_n^c$) is typically 0-5, 5-10, 10-15, 15-20, 20-30 or even more, preferably 0-5 or 5-10. X may represent either D or L amino acids.

According to an alternative specific embodiment the chimeric peptide as used herein comprises or consists of D-amino acid chimeric peptides of the above disclosed L-amino acid chimeric peptides. Exemplary D retro-inverso chimeric peptides according to the present invention are e.g. the generic D-TAT-IB peptide $NH_2$—$X_n^b$-DQXXXXXXXX-LXLTTPR-$X_n^a$—$X_n^b$-RRRQRRKKR-$X_n^b$—COOH (D-TAT-IB (generic) (s)) [SEQ ID NO: 12]. Herein, X, $X_n^a$ and $X_n^b$ are preferably as defined above (preferably representing D amino acids). More preferably, the chimeric peptide as used herein comprises or consists of D-amino acid chimeric peptides according to the TAT-IB1 peptide NH$_2$-DQSRPVQPFLNLTTPRKPRPPRRRQRRKKRG-COOH (D-TAT-IB1(s)) [SEQ ID NO: 11]. Alternatively or additionally, the chimeric peptide as used herein comprises or consists of the D-amino acid chimeric peptide sequence TDQSR-PVQPFLNLTTPRKPRYTDPPRRRQRRKKRG (D-TAT-IB1) [SEQ ID NO: 25], or XT/SDQXXXXXXXLXLT-TPRXXXXXXXXXRRRQRRKKRXXXXXXX (D-TAT-IB generic) [SEQ ID NO: 26], wherein X is preferably also as defined above, or the chimeric peptide as used herein comprises or consists of the D-amino acid chimeric peptide sequence DQSRPVQPFLNLTTPRKPRPPRRRQRRKKR (D-TAT-IB1(s1)) [SEQ ID NO: 30], DQSRPVQPFLNLT-TPRKPRX$_n^c$RRRQRRKKRG (D-TAT-IB1(s2)) [SEQ ID NO: 31], or DQSRPVQPFLNLTTPRKPRX$_n^c$RRRQR-RKKR (D-TAT-IB1(s3)) [SEQ ID NO: 32]. X$_n^c$ may be as defined above.

The first and second domain(s) of the chimeric peptide as defined above may be linked to each other by chemical or biochemical coupling carried out in any suitable manner known in the art, e.g. by establishing a peptide bond between the first and the second domain(s) e.g. by expressing the first and second domain(s) as a fusion protein, or e.g. by crosslinking the first and second domain(s) of the chimeric peptide as defined above.

Many known methods suitable for chemical crosslinking of the first and second domain(s) of the chimeric peptide as defined above are non-specific, i.e. they do not direct the point of coupling to any particular site on the transport polypeptide or cargo macromolecule. As a result, use of non-specific crosslinking agents may attack functional sites or sterically block active sites, rendering the conjugated proteins biologically inactive. Thus, preferably such crosslinking methods are used, which allow a more specific coupling of the first and second domain(s).

In this context, one way to increasing coupling specificity is a direct chemical coupling to a functional group present only once or a few times in one or both of the first and second domain(s) to be crosslinked. For example, cysteine, which is the only protein amino acid containing a thiol group, occurs in many proteins only a few times. Also, for example, if a polypeptide contains no lysine residues, a crosslinking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity. Cysteine residues may be replaced when they occur in parts of a polypeptide sequence where their participation in a crosslinking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for crosslinking purposes. When a cysteine residue is introduced, introduction at or near the amino or carboxy terminus is preferred. Conventional methods are available for such amino acid sequence modifications, wherein the polypeptide of interest is produced by chemical synthesis or via expression of recombinant DNA.

Coupling of the first and second domain(s) of the chimeric peptide as defined above and used herein can also be accomplished via a coupling or conjugating agent. There are several intermolecular crosslinking reagents which can be utilized (see for example, Means and Feeney, CHEMICAL MODIFICATION OF PROTEINS, Holden-Day, 1974, pp. 39-43). Among these reagents are, for example, N-succinimidyl 3-(2-pyridyldithio)propionate (SPDP) or N,N'-(1,3-phenylene) bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other crosslinking reagents useful for this purpose include: p,p'-difluoro-m, m'-dinitrodiphenylsulfone which forms irreversible crosslinkages with amino and phenolic groups); dimethyl adipimidate (which is specific for amino groups); phenol-1,4 disulfonylchloride (which reacts principally with amino groups); hexamethylenediisocyanate or di isothiocyanate, or azophenyl-p-diisocyanate (which reacts principally with amino groups); glutaraldehyde (which reacts with several different side chains) and disdiazobenzidine (which reacts primarily with tyrosine and histidine).

Crosslinking reagents used for crosslinking the first and second domain(s) of the chimeric peptide as defined above may be homobifunctional, i.e. having two functional groups that undergo the same reaction. A preferred homobifunctional crosslinking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible crosslinking of polypeptides that contain cysteine residues.

Crosslinking reagents used for crosslinking the first and second domain(s) of the chimeric peptide as defined above may also be heterobifunctional. Heterobifunctional crosslinking agents have two different functional groups, for example an amine-reactive group and a thiol-reactive group, that will crosslink two proteins having free amines and thiols, respectively. Examples of heterobifunctional crosslinking agents are succinimidyl 4-(N-maleimidomethyl)cyclohexane-1-carboxylate ("SMCC"), m-maleimidobenzoyl-N-hydroxysuccin imide ester ("MBS"), and succinimide 4-(p-maleimidophenyl)butyrate ("SMPB"), an extended chain analog of MBS. The succinimidyl group of these crosslinkers reacts with a primary amine, and the thiol-reactive maleimide forms a covalent bond with the thiol of a cysteine residue.

Crosslinking reagents suitable for crosslinking the first and second domain(s) of the chimeric peptide as defined above often have low solubility in water. A hydrophilic moiety, such as a sulfonate group, may thus be added to the crosslinking reagent to improve its water solubility. In this respect, Sulfo-MBS and Sulfo-SMCC are examples of crosslinking reagents modified for water solubility, which may be used according to the present invention.

Likewise, many crosslinking reagents yield a conjugate that is essentially non-cleavable under cellular conditions. However, some crosslinking reagents particularly suitable for crosslinking the first and second domain(s) of the chimeric peptide as defined above contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable crosslinkers. The use of a cleavable crosslinking reagent permits the cargo moiety to separate from the transport polypeptide after delivery into the target cell. Direct disulfide linkage may also be useful.

Numerous crosslinking reagents, including the ones discussed above, are commercially available. Detailed instructions for their use are readily available from the commercial suppliers. A general reference on protein crosslinking and conjugate preparation is: Wong, CHEMISTRY OF PROTEIN CONJUGATION AND CROSSLINKING, CRC Press (1991).

Chemical crosslinking of the first and second domain(s) of the chimeric peptide as defined above may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the crosslinking reagent, such as in "long-chain SPDP" (Pierce Chem. Co., Rockford, Ill., cat. No. 21651 H).

Furthermore, variants, fragments or derivatives of one of the above disclosed chimeric peptides may be used herein. With regard to fragments and variants it is generally referred to the definition given above for JNK inhibitor sequences.

Particularly, in the context of the present invention, a "variant of a chimeric peptide" is preferably a sequence derived from any of the sequences according to SEQ ID NOs: 9 to 12 and 23 to 32, wherein the chimeric variant comprises amino acid alterations of the chimeric peptides according to SEQ ID NOs: 9 to 12 and 23 to 32 as used herein. Such alterations typically comprise 1 to 20, preferably 1 to 10 and more preferably 1 to 5 substitutions, additions and/or deletions (leading to fragments) of amino acids according to SEQ ID NOs: 9 to 12 and 23 to 32, wherein the altered chimeric peptide as used herein exhibits a sequence identity with any of the sequences according to SEQ ID NOs: 9-12 and 23 to 32 of at least about 30%, 50%, 70%, 80%, or 95%, 98%, or even 99%. Preferably, these variants retain the biological activity of the first and the second domain as contained in the chimeric peptide as used herein, i.e. the trafficking activity of the first domain as disclosed above and the activity of the second domain for binding JNK and/or inhibiting the activation of at least one JNK activated transcription factor.

Accordingly, the chimeric peptide as used herein also comprises fragments of the afore disclosed chimeric peptides, particularly of the chimeric peptide sequences according to any of SEQ ID NOs: 9 to 12 and 23 to 32. Thus, in the context of the present invention, a "fragment of the chimeric peptide" is preferably a sequence derived any of the sequences according to SEQ ID NOs: 9 to 12 and 23 to 32, wherein the fragment comprises at least 4 contiguous amino acids of any of SEQ ID NOs: 9 to 12 and 23 to 32. This fragment preferably comprises a length which is sufficient to allow specific recognition of an epitope from any of these sequences and to transport the sequence into the cells, the nucleus or a further preferred location. Even more preferably, the fragment comprises 4 to 18, 4 to 15, or most preferably 4 to 10 contiguous amino acids of any of SEQ ID NOs: 9 to 12 and 23 to 32. Fragments of the chimeric peptide as used herein further may be defined as a sequence sharing a sequence identity with any of the sequences according to any of SEQ ID NOs: 99 to 12 and 23 to 32 of at least about 30%, 50%, 70%, 80%, or 95%, 98%, or even 99%.

Finally, the chimeric peptide as used herein also comprises derivatives of the afore disclosed chimeric peptides, particularly of the chimeric peptide sequences according to any of SEQ ID NOs: 9 to 12 and 23 to 32.

The present invention additionally refers to the use of nucleic acid sequences encoding JNK inhibitor sequences as defined above, chimeric peptides or their fragments, variants or derivatives, all as defined above, for the preparation of a pharmaceutical composition for treating non-chronic or chronic inflammatory digestive diseases in a subject as defined herein. A preferable suitable nucleic acid encoding an JNK inhibitor sequence as used herein is typically chosen from human IB1 nucleic acid (GenBank Accession No. (AF074091), rat IB1 nucleic acid (GenBank Accession No. AF 108959), or human IB2 (GenBank Accession No AF218778) or from any nucleic acid sequence encoding any of the sequences as defined above, i.e. any sequence according to SEQ ID NO: 1-26.

Nucleic acids encoding the JNK inhibitor sequences as used herein or chimeric peptides as used herein may be obtained by any method known in the art (e.g. by PCR amplification using synthetic primers hybridizable to the 3'- and 5'-termini of the sequence and/or by cloning from a cDNA or genomic library using an oligonucleotide sequence specific for the given gene sequence).

Additionally, nucleic acid sequences are disclosed herein as well, which hybridize under stringent conditions with the appropriate strand coding for a (native) JNK inhibitor sequence or chimeric peptide as defined above. Preferably, such nucleic acid sequences comprise at least 6 (contiguous) nucleic acids, which have a length sufficient to allow for specific hybridization. More preferably, such nucleic acid sequences comprise 6 to 38, even more preferably 6 to 30, and most preferably 6 to 20 or 6 to 10 (contiguous) nucleic acids.

"Stringent conditions" are sequence dependent and will be different under different circumstances. Generally, stringent conditions can be selected to be about 5° C. lower than the thermal melting point (TM) for the specific sequence at a defined ionic strength and pH. The TM is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

"High stringency conditions" may comprise the following, e.g. Step 1: Filters containing DNA are pretreated for 8 hours to overnight at 65° C. in buffer composed of 6*SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5–20*10$^6$ cpm of $^{32}$P-labeled probe. Step 3: Filters are washed for 1 hour at 37° C. in a solution containing 2*SSC, 0.01% PVP, 0.01% Ficoll, and 0.01% BSA. This is followed by a wash in 0.1*SSC at 50° C. for 45 minutes. Step 4: Filters are autoradiographed. Other conditions of high stringency that may be used are well known in the art (see e.g. Ausubel et al, (eds.), 1993, Current Protocols in Molecular Biology, John Wiley and Sons, NY; and Kriegler, 1990, Gene Transfer and Expression, a Laboratory Manual, Stockton Press, NY).

"Moderate stringency conditions" can include the following: Step 1: Filters containing DNA are pretreated for 6 hours at 55° C. in a solution containing 6*SSC, 5*Denhardt's solution, 0.5% SDS and 100 mg/ml denatured salmon sperm DNA. Step 2: Filters are hybridized for 18-20 hours at 55° C. in the same solution with 5–20*10$^6$ cpm $^{32}$P-labeled probe added. Step 3: Filters are washed at 37° C. for 1 hour in a solution containing 2*SSC, 0.1% SDS, then washed twice for 30 minutes at 60° C. in a solution containing 1*SSC and 0.1% SDS. Step 4: Filters are blotted dry and exposed for autoradiography. Other conditions of moderate stringency that may be used are well-known in the art (see e.g. Ausubel et al., (eds.), 1993, Current Protocols in Molecular Biology, John Wiley and Sons, NY; and Kriegler, 1990, Gene Transfer and Expression, a Laboratory Manual, Stockton Press, NY).

Finally, "low stringency conditions" can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5–20×106 cpm $^{32}$P-labeled probe. Step 3: Filters are washed for 1.5 hours at 55 C in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g. as employed for cross-species hybridizations). See e.g. Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

The nucleic acid sequences as defined above according to the present invention can be used to express peptides, i.e. an JNK inhibitor sequence as used herein or an chimeric peptide as used herein for analysis, characterization or therapeutic use; as markers for tissues in which the corresponding peptides (as used herein) are preferentially expressed (either constitutively or at a particular stage of tissue differentiation or development or in disease states). Other uses for these nucleic acids include, e.g. molecular weight markers in gel electrophoresis-based analysis of nucleic acids.

According to a further embodiment of the present invention, expression vectors may be used for the above purposes for recombinant expression of one or more JNK inhibitor sequences and/or chimeric peptides as defined above. The term "expression vector" is used herein to designate either circular or linear DNA or RNA, which is either double-stranded or single-stranded. It further comprises at least one nucleic acid as defined above to be transferred into a host cell or into a unicellular or multicellular host organism. The expression vector as used herein preferably comprises a nucleic acid as defined above encoding the JNK inhibitor sequence as used herein or a fragment or a variant thereof, or the chimeric peptide as used herein, or a fragment or a variant thereof. Additionally, an expression vector according to the present invention preferably comprises appropriate elements for supporting expression including various regulatory elements, such as enhancers/promoters from viral, bacterial, plant, mammalian, and other eukaryotic sources that drive expression of the inserted polynucleotide in host cells, such as insulators, boundary elements, LCRs (e.g. described by Blackwood and Kadonaga (1998), Science 281, 61-63) or matrix/scaffold attachment regions (e.g. described by Li, Harju and Peterson, (1999), Trends Genet. 15, 403-408). In some embodiments, the regulatory elements are heterologous (i.e. not the native gene promoter). Alternately, the necessary transcriptional and translational signals may also be supplied by the native promoter for the genes and/or their flanking regions.

The term "promoter" as used herein refers to a region of DNA that functions to control the transcription of one or more nucleic acid sequences as defined above, and that is structurally identified by the presence of a binding site for DNA-dependent RNA-polymerase and of other DNA sequences, which interact to regulate promoter function. A functional expression promoting fragment of a promoter is a shortened or truncated promoter sequence retaining the activity as a promoter. Promoter activity may be measured by any assay known in the art (see e.g. Wood, de Wet, Dewji, and DeLuca, (1984), Biochem Biophys. Res. Commun. 124, 592-596; Seliger and McElroy, (1960), Arch. Biochem. Biophys. 88, 136-141) or commercially available from Promega®).

An "enhancer region" to be used in the expression vector as defined herein, typically refers to a region of DNA that functions to increase the transcription of one or more genes. More specifically, the term "enhancer", as used herein, is a DNA regulatory element that enhances, augments, improves, or ameliorates expression of a gene irrespective of its location and orientation vis-à-vis the gene to be expressed, and may be enhancing, augmenting, improving, or ameliorating expression of more than one promoter.

The promoter/enhancer sequences to be used in the expression vector as defined herein, may utilize plant, animal, insect, or fungus regulatory sequences. For example, promoter/enhancer elements can be used from yeast and other fungi (e.g. the GAL4 promoter, the alcohol dehydrogenase promoter, the phosphoglycerol kinase promoter, the alkaline phosphatase promoter). Alternatively, or in addition, they may include animal transcriptional control regions, e.g. (i) the insulin gene control region active within pancreatic beta-cells (see e.g. Hanahan, et al, 1985. Nature 315: 115-122); (ii) the immunoglobulin gene control region active within lymphoid cells (see e.g. Grosschedl, et al, 1984, Cell 38: 647-658); (iii) the albumin gene control region active within liver (see e.g. Pinckert, et al, 1987. Genes and Dev 1: 268-276; (iv) the myelin basic protein gene control region active within brain oligodendrocyte cells (see e.g. Readhead, et al, 1987, Cell 48: 703-712); and (v) the gonadotropin-releasing hormone gene control region active within the hypothalamus (see e.g. Mason, et al, 1986, Science 234: 1372-1378), and the like.

Additionally, the expression vector as defined herein may comprise an amplification marker. This amplification marker may be selected from the group consisting of, e.g. adenosine deaminase (ADA), dihydrofolate reductase (DHFR), multiple drug resistance gene (MDR), ornithine decarboxylase (ODC) and N-(phosphonacetyl)-L-aspartate resistance (CAD).

Exemplary expression vectors or their derivatives suitable for the present invention particularly include, e.g. human or animal viruses (e.g. vaccinia virus or adenovirus); insect viruses (e.g. baculovirus); yeast vectors; bacteriophage vectors (e.g. lambda phage); plasmid vectors and cosmid vectors.

The present invention additionally may utilize a variety of host-vector systems, which are capable of expressing the peptide coding sequence(s) of nucleic acids as defined above. These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Preferably, a host cell strain, suitable for such a host-vector system, may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptide. Moreover, different host cells possess characteristic and specific mechanisms for the translational and post-translational processing and modification (e.g. glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an non-glycosylated core peptide; whereas expression within mammalian cells ensures "native" glycosylation of a heterologous peptide.

The present invention further provides the use of antibodies directed against the JNK inhibitor sequences and/or chimeric peptides as described above, for preparing a pharmaceutical composition for the treatment of non-chronic or chronic inflammatory digestive diseases as defined herein. Furthermore, efficient means for production of antibodies specific for JNK inhibitor sequences according to the present invention, or for chimeric peptides containing such an inhibitor sequence, are described and may be utilized for this purpose.

According to the invention, JNK inhibitor sequences and/or chimeric peptides as defined herein, as well as, fragments, variants or derivatives thereof, may be utilized as immunogens to generate antibodies that immunospecifically bind these peptide components. Such antibodies include, e.g. polyclonal, monoclonal, chimeric, single chain, Fab fragments and a Fab expression library. In a specific embodiment the present invention provides antibodies to chimeric peptides or to JNK inhibitor sequences as defined above. Various procedures known within the art may be used for the production of these antibodies.

By way of example, various host animals may be immunized for production of polyclonal antibodies by injection with any chimeric peptide or JNK inhibitor sequence as defined above. Various adjuvants may be used thereby to increase the immunological response which include, but are not limited to, Freund's (complete and incomplete) adjuvant, mineral gels (e.g. aluminum hydroxide), surface active substances (e.g. lysolecithin, pluronic polyols, polyanions, peptides, oil emulsions, dinitrophenol, etc.), CpG, polymers, Pluronics, and human adjuvants such as Bacille Calmette-Guerin and *Corynebacterium parvum*.

For preparation of monoclonal antibodies directed towards a chimeric peptide or a JNK inhibitor sequence as defined above, any technique may be utilized that provides for the production of antibody molecules by continuous cell line culture. Such techniques include, but are not limited to, the hybridoma technique (see Kohler and Milstein, 1975. Nature 256: 495-497); the trioma technique; the human B-cell hybridoma technique (see Kozbor, et al, 1983, Immunol Today 4: 72) and the EBV hybridoma technique to produce human monoclonal antibodies (see Cole, et 1985. In: Monoclonal Antibodies and Cancer Therapy, Alan R. Liss, Inc., pp. 77-96). Human monoclonal antibodies may be utilized in the practice of the present invention and may be produced by the use of human hybridomas (see Cote, et al., 1983. Proc Natl Acad Sci USA 80: 2026-2030) or by transforming human B-cells with Epstein Barr Virus in vitro (see Cole, et a/., 1985. In: Monoclonal Antibodies and Cancer Therapy (Alan R. Liss, Inc., pp. 77-96).

According to the invention, techniques can be adapted for the production of single-chain antibodies specific to the INK inhibitor sequences and/or chimeric peptides (see e.g. U.S. Pat. No. 4,946,778) as defined herein. In addition, methods can be adapted for the construction of Fab expression libraries (see e.g. Huse et al., 1989. Science 246: 1275-1281) to allow rapid and effective identification of monoclonal Fab fragments with the desired specificity for these JNK inhibitor sequences and/or chimeric peptides. Non-human antibodies can be "humanized" by techniques well known in the art (see e.g. U.S. Pat. No. 5,225,539). Antibody fragments that contain the idiotypes to a JNK inhibitor sequences and/or chimeric peptide as defined herein may be produced by techniques known in the art including, e.g. (i) a $F(ab')_2$ fragment produced by pepsin digestion of an antibody molecule; (ii) a Fab fragment generated by reducing the disulfide bridges of an $F(ab')_2$ fragment; (iii) a Fab fragment generated by the treatment of the antibody molecule with papain and a reducing agent and (iv) Fv fragments.

In one embodiment of this invention, methods, that may be utilized for the screening of antibodies and which possess the desired specificity include, but are not limited to, enzyme-linked immunosorbent assay (ELISA) and other immunologically-mediated techniques known within the art. In a specific embodiment, selection of antibodies that are specific to a particular epitope of an JNK inhibitor sequence and/or an chimeric peptide as defined herein (e.g. a fragment thereof typically comprising a length of from 5 to 20, preferably 8 to 18 and most preferably 8 to 11 amino acids) is facilitated by generation of hybridomas that bind to the fragment of an JNK inhibitor sequence and/or an chimeric peptide, as defined herein, possessing such an epitope. These antibodies that are specific for an epitope as defined above are also provided herein.

The antibodies as defined herein may be used in methods known within the art referring to the localization and/or quantification of an JNK inhibitor sequence (and/or correspondingly to a chimeric peptide as defined above), e.g. for use in measuring levels of the peptide within appropriate physiological samples, for use in diagnostic methods, or for use in imaging the peptide, and the like.

The JNK inhibitor sequences, chimeric peptides, nucleic acids, vectors, host cells and/or antibodies as defined according to the invention can be formulated in a pharmaceutical composition, which may be applied in the prevention or treatment of any of the diseases as defined herein, particularly in the prevention or treatment of non-chronic or chronic inflammatory digestive diseases as defined herein. Typically, such a pharmaceutical composition used according to the present invention includes as an active component, e.g.: (i) any one or more of the JNK inhibitor sequences and/or chimeric peptides as defined above, and/or variants, fragments or derivatives thereof, particularly JNK inhibitor sequences according to any of sequences of SEQ ID NOs: 1 to 4 and 13 to 20 and 33-100 and/or chimeric peptides according to any of sequences of SEQ ID NOs: 9 to 12 and 23 to 32, and/or JNK inhibitor sequences according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions; and/or (ii) nucleic acids encoding an JNK inhibitor sequence and/or an chimeric peptide as defined above and/or variants or fragments thereof, and/or (iii) cells comprising any one or more of the JNK inhibitor sequences and/or chimeric peptides, and/or variants, fragments or derivatives thereof, as defined above and/or (iv) cells transfected with a vector and/or nucleic acids encoding an JNK inhibitor sequence and/or an chimeric peptide as defined above and/or variants or fragments thereof.

According to a preferred embodiment, such a pharmaceutical composition as used according to the present invention typically comprises a safe and effective amount of a component as defined above, preferably of at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5-8 and 21 to 22, or variants or fragments thereof within the above definitions, or at least one nucleic acids encoding same, or at least one vector, host cell or antibody as defined above.

The inventors of the present invention additionally found, that the JNK-inhibitor sequence and the chimeric peptide, respectively, as defined herein, exhibit a particular well uptake rate into cells involved in the diseases of the present invention. Therefore, the amount of a JNK-inhibitor sequence and chimeric peptide, respectively, in the pharmaceutical composition to be administered to a subject, may—without being limited thereto—have a very low dose. Thus, the dose may be much lower than for peptide drugs known in the art, such as DTS-108 (Florence Meyer-Losic et al., Clin Cancer Res., 2008, 2145-53). This has several positive aspects, for example a reduction of potential side reactions and a reduction in costs.

Preferably, the dose (per kg bodyweight) is in the range of up to 10 mmol/kg, preferably up to 1 mmol/kg, more preferably up to 100 µmol/kg, even more preferably up to 10 µmol/kg, even more preferably up to 1 µmol/kg, even more preferably up to 100 nmol/kg, most preferably up to 50 nmol/kg.

Thus, the dose range may preferably be from about 1 pmol/kg to about 1 mmol/kg, from about 10 pmol/kg to about 0.1 mmol/kg, from about 10 pmol/kg to about 0.01 mmol/kg, from about 50 pmol/kg to about 1 pmol/kg, from about 100 pmol/kg to about 500 nmol/kg, from about 200 pmol/kg to about 300 nmol/kg, from about 300 pmol/kg to about 100 nmol/kg, from about 500 pmol/kg to about 50 nmol/kg, from about 750 pmol/kg to about 30 nmol/kg, from about 250 pmol/kg to about 5 nmol/kg, from about 1 nmol/kg to about 10 nmol/kg, or a combination of any two of said values.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, a "safe and effective amount" as defined above for components of the pharmaceutical compositions as used according to the present invention means an amount of each or all of these components, that is sufficient to significantly induce a positive modification of a non-chronic or chronic inflammatory digestive diseases as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of such a component will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

The pharmaceutical composition as used according to the present invention may furthermore comprise, in addition to one of these substances, a (compatible) pharmaceutically acceptable carrier, excipient, buffer, stabilizer or other materials well known to those skilled in the art.

In this context, the expression "(compatible) pharmaceutically acceptable carrier" preferably includes the liquid or non-liquid basis of the composition. The term "compatible" means that the constituents of the pharmaceutical composition as used herein are capable of being mixed with the pharmaceutically active component as defined above and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the pharmaceutical composition as used herein is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline or buffered (aqueous) solutions, e.g. phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection of the pharmaceutical composition as used herein, a buffer, preferably an aqueous buffer, may be used.

If the pharmaceutical composition as used herein is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The precise nature of the (compatible) pharmaceutically acceptable carrier or other material may depend on the route of administration. The choice of a (compatible) pharmaceutically acceptable carrier may thus be determined in principle by the manner in which the pharmaceutical composition as used according to the invention is administered. The pharmaceutical composition as used according to the invention can be administered, for example, systemically. Routes for administration include, for example, parenteral routes (e.g. via injection), such as intravenous, intramuscular, subcutaneous, intradermal, or transdermal routes, etc., enteral routes, such as oral, or rectal routes, etc., topical routes, such as nasal, or intranasal routes, etc., or other routes, such as epidermal routes or patch delivery.

The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the compound is to be administered perorally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

Pharmaceutical compositions for oral administration may be in tablet, capsule, powder or liquid form. A tablet may include a solid carrier as defined above, such as gelatin, and optionally an adjuvant. Liquid pharmaceutical compositions for oral administration generally may include a liquid carrier as defined above, such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated.

Prevention and/or treatment of a disease as defined herein typically includes administration of a pharmaceutical composition as defined above. The term "modulate" includes the suppression of expression of JNK when it is over-expressed in any of the above diseases. It also includes, without being limited thereto, suppression of phosphorylation of c-jun, ATF2 or NFAT4 in any of the above diseases, for example, by using at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, as a competitive inhibitor of the natural c-jun, ATF2 and NFAT4 binding site in a cell. The term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos. When a non-chronic or chronic inflammatory digestive disease is associated with JNK overexpression, such suppressive JNK inhibitor sequences can be introduced to a cell. In some instances, "modulate" may then include the increase of JNK expression, for example by use of an IB peptide-specific antibody that blocks the binding of an IB-peptide to JNK, thus preventing JNK inhibition by the IB-related peptide.

Prevention and/or treatment of a subject with the pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the non-chronic or chronic inflammatory digestive disease.

Accordingly, peptides as defined above, e.g. at least one JNK inhibitor sequence according to any of sequences of SEQ ID NOs: 1 to 4 and 13 to 20 and 33-100 and/or at least one chimeric peptide according to any of sequences of SEQ ID NOs: 9 to 12 and 23 to 32, and/or at least one JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in a specific embodiment of the present invention to treat non-chronic or chronic inflammatory digestive diseases as defined above by modulating activated JNK signaling pathways.

Peptides as defined above and as contained in the inventive pharmaceutical composition may be also encoded by nucleic acids. This is particularly advantageous, if the above peptides are administered for the purpose of gene therapy. In this context, gene therapy refers to therapy that is performed by administration of a specific nucleic acid as defined above to a subject, e.g. by way of a pharmaceutical composition as defined above, wherein the nucleic acid(s) exclusively comprise(s) L-amino acids. In this embodiment of the present invention, the nucleic acid produces its encoded peptide(s), which then serve(s) to exert a therapeutic effect by modulating function of the disease or disorder. Any of the methods relating to gene therapy available within the art may be used in the practice of the present invention (see e.g. Goldspiel, et al, 1993. Clin Pharm 12: 488-505).

In a preferred embodiment, the nucleic acid as defined above and as used for gene therapy is part of an expression vector encoding and expressing any one or more of the 1B-related peptides as defined above within a suitable host, i.e. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions. In a specific embodiment, such an expression vector possesses a promoter that is operably-linked to coding region(s) of a JNK inhibitor sequence. The promoter may be defined as above, e.g. inducible or constitutive, and, optionally, tissue-specific.

In another specific embodiment, a nucleic acid molecule as defined above is used for gene therapy, in which the coding sequences of the nucleic acid molecule (and any other desired sequences thereof) as defined above are flanked by regions that promote homologous recombination at a desired site within the genome, thus providing for intra-chromosomal expression of these nucleic acids (see e.g. Koller and Smithies, 1989. Proc Natl Acad Sci USA 86: 8932-8935).

Delivery of the nucleic acid as defined above according to the invention into a patient for the purpose of gene therapy, particular in the context of the above mentioned non-chronic or chronic inflammatory digestive diseases as defined above may be either direct (i.e. the patient is directly exposed to the nucleic acid or nucleic acid-containing vector) or indirect (i.e. cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g. constructing the nucleic acid as part of an appropriate nucleic acid expression vector and administering the same in a manner such that it becomes intracellular (e.g. by infection using a defective or attenuated retroviral or other viral vector; see U.S. Pat. No. 4,980,286); directly injecting naked DNA; using microparticle bombardment (e.g. a "GeneGun"; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see e.g. Wu and Wu, 1987.) Biol Chem 262: 4429-4432), which can be used to "target" cell types that specifically express the receptors of interest, etc.

An additional approach to gene therapy in the practice of the present invention involves transferring a nucleic acid as defined above into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g. antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including e.g. transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods that ensure that the necessary developmental and physiological functions of the recipient cells are not disrupted by the transfer. See e.g. Loeffler and Behr, 1993. Meth Enzymol 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g. injection of epithelial cells (e.g. subcutaneously), application of recombinant skin cells as a skin graft onto the patient, and intravenous injection of recombinant blood cells (e.g. hematopoietic stem or progenitor cells). The total amount of cells that are envisioned for use depend upon the desired effect, patient state, and the like, and may be determined by one skilled within the art. Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, Cell 71: 973-985), hematopoietic stem or progenitor cells, e.g. as obtained from bone marrow, umbilical cord blood, peripheral blood, fetal liver, and the like. In a preferred embodiment, the cells utilized for gene therapy are autologous to the patient.

Alternatively and/or additionally, for treating diseases as mentioned herein targeting therapies may be used to deliver the JNK inhibitor sequences, chimeric peptides, and/or nucleic acids as defined above more specifically to certain types of cell, by the use of targeting systems such as (a targeting) antibody or cell specific ligands. Antibodies used for targeting are typically specific for cell surface proteins of cells associated with any of the diseases as defined below. By way of example, these antibodies may be directed to cell surface antibodies such as e.g. B cell-associated surface proteins such as MHC class II DR protein, CD18 (LFA-1 beta chain), CD45RO, CD40 or Bgp95, or cell surface proteins selected from e.g. CD2, CD2, CD4, CD5, CD7, CD8, CD9, CD10, CD13, CD16, CD19, CD20, CD21, CD22, CD23, CD24, CD25, CD30, CD33, CD34, CD38, CD39, CD4, CD43, CD45, CD52, CD56, CD68, CD71, CD138, etc. Targeting constructs may be typically prepared by covalently binding the JNK inhibitor sequences, chimeric peptides, and nucleic acids as defined herein according to the invention to an antibody specific for a cell surface protein or by binding to a cell specific ligand. Proteins may e.g. be bound to such an antibody or may be attached thereto by a peptide bond or by chemical coupling, crosslinking, etc. The targeting therapy may then be carried out by administering the targeting construct in a pharmaceutically efficient amount to a patient by any of the administration routes as defined below, e.g. intra-peritoneal, nasal, intravenous, oral and patch delivery routes. Preferably, the JNK inhibitor sequences, chimeric peptides, or nucleic acids as defined herein according to the invention, being attached to the targeting antibodies or cell specific ligands as defined above, may be released in vitro or in vivo, e.g. by hydrolysis of the covalent bond, by peptidases or by any other suitable method. Alternatively, if the JNK inhibitor sequences, chimeric peptides, or nucleic acids as defined herein according to the invention are attached to a small cell specific ligand, release of the ligand may not be carried out. If present at the cell surface, the chimeric peptides may enter the cell upon the activity of its trafficking sequence. Targeting may be desirable for a variety of reasons; for example if the JNK inhibitor sequences, chimeric peptides, and nucleic acids as defined herein according to the invention are unacceptably toxic or if it would otherwise require a too high dosage.

Instead of administering the JNK inhibitor sequences and/or chimeric peptides as defined herein according to the invention directly, they could be produced in the target cells by expression from an encoding gene introduced into the cells, e.g. from a viral vector to be administered. The viral vector typically encodes the JNK inhibitor sequences and/or chimeric peptides as defined herein according to the invention. The vector could be targeted to the specific cells to be treated. Moreover, the vector could contain regulatory elements, which are switched on more or less selectively by the target cells upon defined regulation. This technique represents a variant of the VDEPT technique (virus-directed enzyme prodrug therapy), which utilizes mature proteins instead of their precursor forms.

Alternatively, the JNK inhibitor sequences and/or chimeric peptides as defined herein could be administered in a precursor form by use of an antibody or a virus. These JNK inhibitor sequences and/or chimeric peptides may then be converted into the active form by an activating agent produced in, or targeted to, the cells to be treated. This type of approach is sometimes known as ADEPT (antibody-directed enzyme prodrug therapy) or VDEPT (virus-directed enzyme prodrug therapy); the former involving targeting the activating agent to the cells by conjugation to a cell-specific antibody, while the latter involves producing the activating agent, e.g. a JNK inhibitor sequence or the chimeric peptide, in a vector by expression from encoding DNA in a viral vector (see for example, EP-A-415731 and WO 90/07936).

According to a further embodiment, the JNK inhibitor sequences, chimeric peptides, nucleic acid sequences or antibodies to JNK inhibitor sequences or to chimeric peptides as defined herein, e.g. an JNK inhibitor sequence according to any of sequences of SEQ ID NOs: 1 to 4 and 13 to 20 and 33-100 and/or a chimeric peptide according to any of sequences of SEQ ID NOs: 9 to 12 and 23 to 32, and/or an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or variants or fragments thereof within the above definitions, may be utilized in (in vitro) assays (e.g. immunoassays) to detect, prognose, diagnose, or monitor various conditions and disease states selected from non-chronic or chronic inflammatory digestive diseases as defined above, or monitor the treatment thereof. The immunoassay may be performed by a method comprising contacting a sample derived from a patient with an antibody to an JNK inhibitor sequence, a chimeric peptide, or a nucleic acid sequence, as defined above, under conditions such that immunospecific-binding may occur, and subsequently detecting or measuring the amount of any immunospecific-binding by the antibody. In a specific embodiment, an antibody specific for an JNK inhibitor sequence, a chimeric peptide or a nucleic acid sequence may be used to analyze a tissue or serum sample from a patient for the presence of JNK or a JNK inhibitor sequence; wherein an aberrant level of JNK is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc. Alternatively, (in vitro) assays may be performed by delivering the JNK inhibitor sequences, chimeric peptides, nucleic acid sequences or antibodies to JNK inhibitor sequences or to chimeric peptides, as defined above, to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans.

The present invention additionally provides the use of kits for diagnostic or therapeutic purposes, particular for the treatment, prevention or monitoring of non-chronic or chronic inflammatory digestive diseases as defined above, wherein the kit includes one or more containers containing JNK inhibitor sequences, chimeric peptides, nucleic acid sequences and/or antibodies to these JNK inhibitor sequences or to chimeric peptides as defined above, e.g. an anti-JNK inhibitor sequence antibody to an JNK inhibitor sequence according to any of sequences of SEQ ID NOs: 1 to 4 and 13 to 20 and 33-100, to a chimeric peptide according to any of sequences of SEQ ID NOs: 9 to 12 and 23 to 32, to an JNK inhibitor sequence according to any of sequences of SEQ ID NOs: 1 to 4 and 13 to 20 and 33-100 comprising a trafficking sequence according to any of SEQ ID NOs: 5 to 8 and 21 to 22, or to or variants or fragments thereof within the above definitions, or such an anti-JNK inhibitor sequence antibody and, optionally, a labeled binding partner to the antibody. The label incorporated thereby into the antibody may include, but is not limited to, a chemiluminescent, enzymatic, fluorescent, colorimetric or radioactive moiety. In another specific embodiment, kits for diagnostic use in the treatment, prevention or monitoring of non-chronic or chronic inflammatory digestive diseases as defined above are provided which comprise one or more containers containing nucleic acids that encode, or alternatively, that are the complement to, an JNK inhibitor sequence and/or a chimeric peptide as defined above, optionally, a labeled binding partner to these nucleic acids, are also provided. In an alternative specific embodiment, the kit may be used for the above purposes as a kit, comprising one or more containers, a pair of oligonucleotide primers (e.g. each 6-30 nucleotides in length) that are capable of acting as amplification primers for polymerase chain reaction (PCR; see e.g. Innis, et al, 1990. PCR PROTOCOLS, Academic Press, Inc., San Diego, Calif.), ligase chain reaction, cyclic probe reaction, and the like, or other methods known within the art used in context with the nucleic acids as defined above. The kit may, optionally, further comprise a predetermined amount of a purified JNK inhibitor sequence as defined above, a chimeric peptide as defined above, or nucleic acids encoding these, for use as a diagnostic, standard, or control in the assays for the above purposes.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

DESCRIPTION OF FIGURES

FIGS. 1A-C are diagrams showing alignments of conserved JBD domain regions in the indicated transcription factors. JNK inhibitor sequences used herein were identified by carrying out sequence alignments. The results of this alignment are exemplarily shown in FIGS. 1A-1C. FIG. 1A depicts the region of highest homology between the JBDs of IB1, IB2, c-Jun and ATF2. Panel B depicts the amino acid sequence of the JBDs of L-IB1(s) and L-IB1 for comparative reasons. Fully conserved residues are indicated by asterisks, while residues changed to Ala in the GFP-JBD$_{23Mut}$ vector are indicated by open circles. FIG. 1C shows the amino acid sequences of chimeric proteins that include a JNK inhibitor sequence and a trafficking sequence. In the example shown, the trafficking sequence is derived from the human immunodeficiency virus (HIV) TAT polypeptide, and the JNK inhibitor sequence is derived from an IB1(s) polypeptide. Human, mouse, and rat sequences are identical in Panels B and C.

FIG. 2 is a diagram showing sequences of generic TAT-IB fusion peptides from human, mouse and rat.

FIG. 8 Primary cultured macrophages were incubated with XG-102 (SEQ ID NO: 11) and extensively washed. Presence of XG-102 (SEQ ID NO: 11) was revealed using a specific antibody against XG-102. XG-102 is strongly incorporated into primary macrophages.

FIG. 14 shows the IB1 cDNA sequence from rat and its predicted amino acid sequence (SEQ ID NO:102)

FIG. 15 shows the IB1 protein sequence from rat encoded by the exon-intron boundary of the rIB1 gene-splice donor (SEQ ID NO:103)

FIG. 16 shows the IB1 protein sequence from Homo sapiens (SEQ ID NO:104)

FIG. 17 shows the IB1 cDNA sequence from Homo sapiens (SEQ ID NO:105)

EXAMPLES

Example 1

Identification of JNK Inhibitor Sequences

Figure 3:
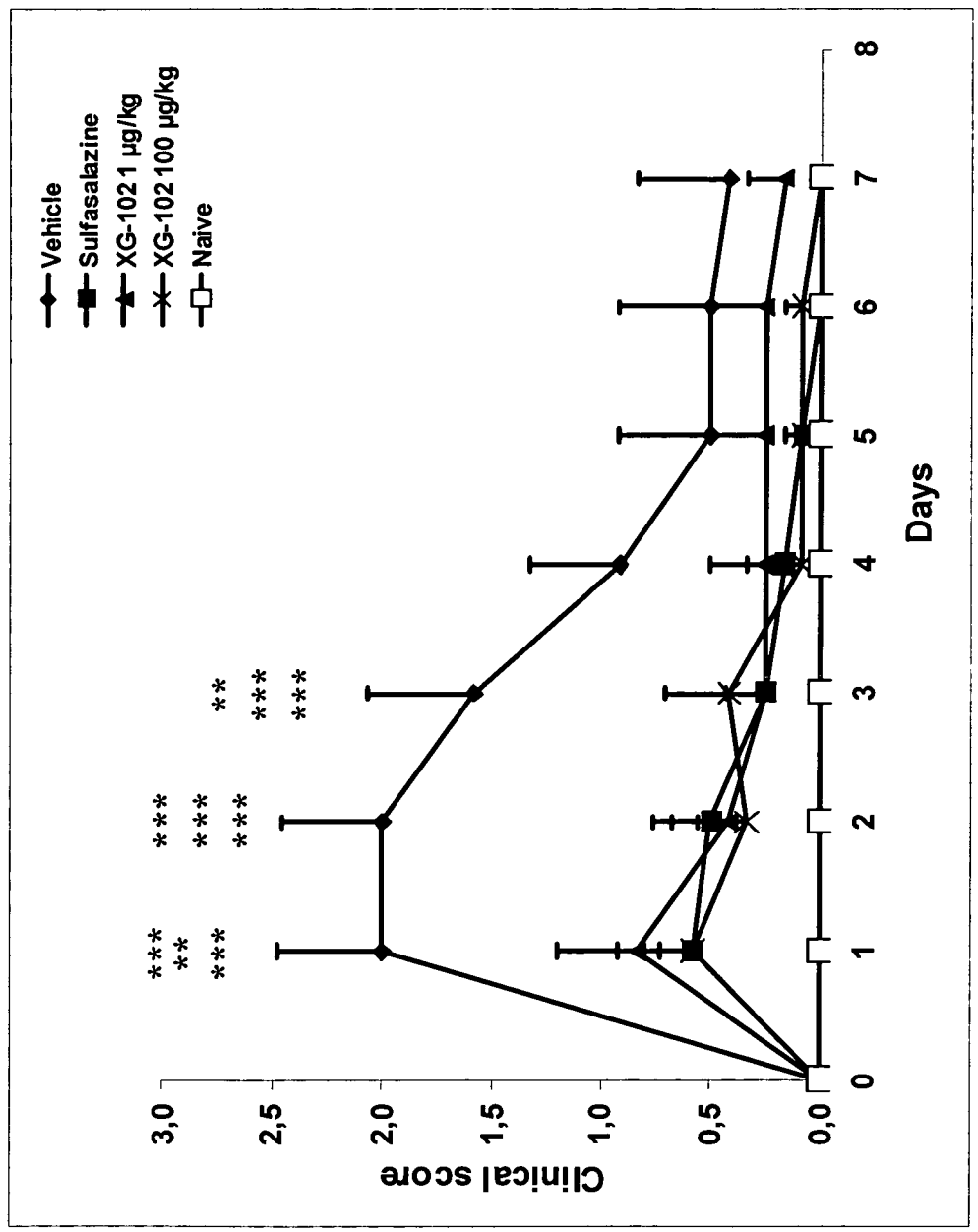
FIG. 3 shows the clinical scores upon treatment with XG-102 (SEQ ID NO: 11) in an IBD study with a treatment using XG-102 in a concentration of 1 and 100 μg/kg SC daily.
Figure 4:
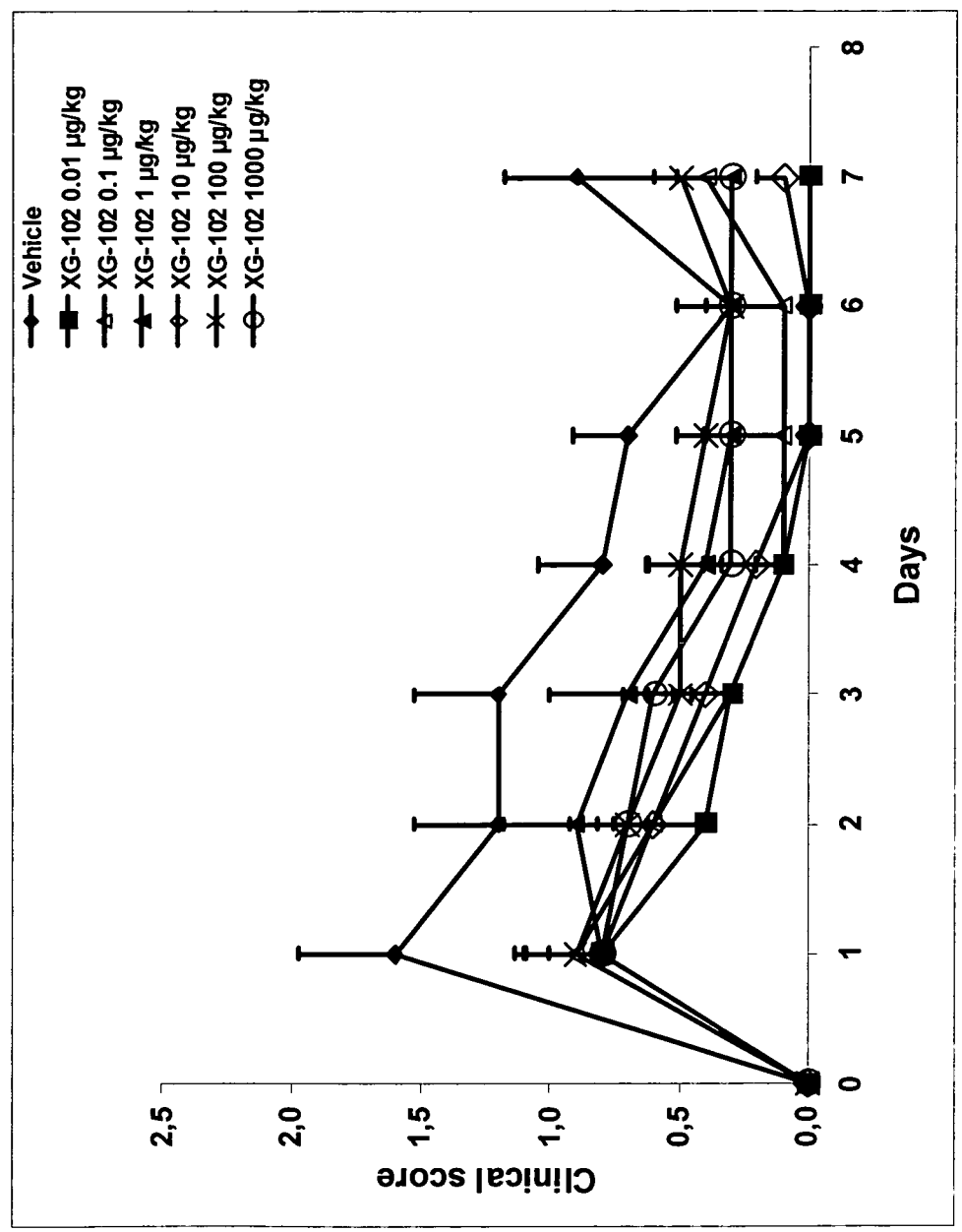
FIG. 4 shows a dose response curve upon treatment with XG-102 (SEQ ID NO: 11) in an IBD study with a treatment using XG-102, in a concentration of 0.01, 0.1, 1, 10, 100 and 1000 μg/kg SC daily.
Figure 5:
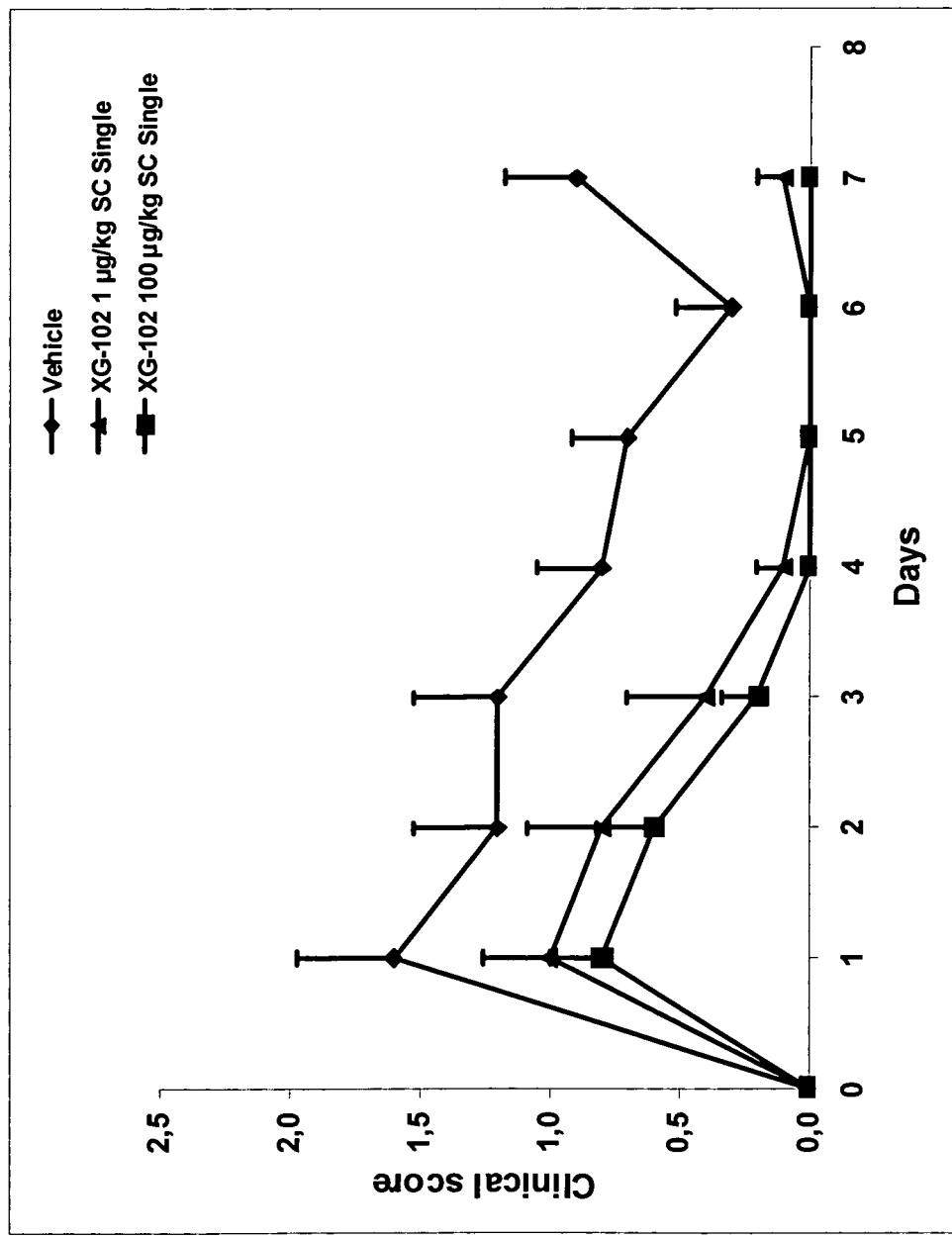
FIG. 5 shows the clinical scores upon treatment with XG-102 (SEQ ID NO: 11) in an IBD study with a treatment using XG-102 (single dose SC) in a concentration of 1 and 100 μg/kg SC as a single dose on day 0.
Figure 6:
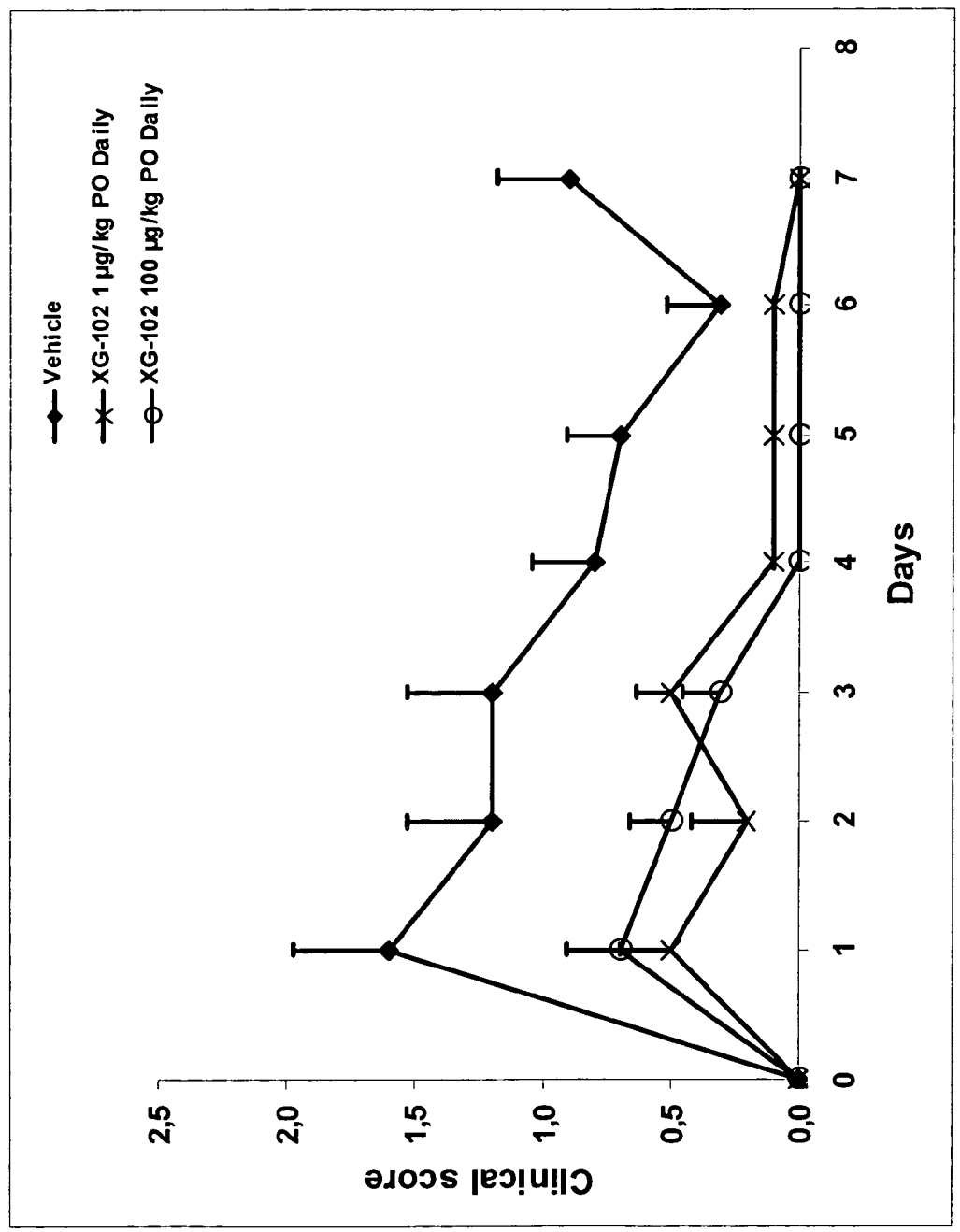
FIG. 6 shows the clinical scores upon treatment with XG-102 (SEQ ID NO: 11) in an IBD study with a treatment using XG-102 (daily, PO) in a concentration of 1 and 100 μg/kg PO as a repeated dose.
Figure 7:
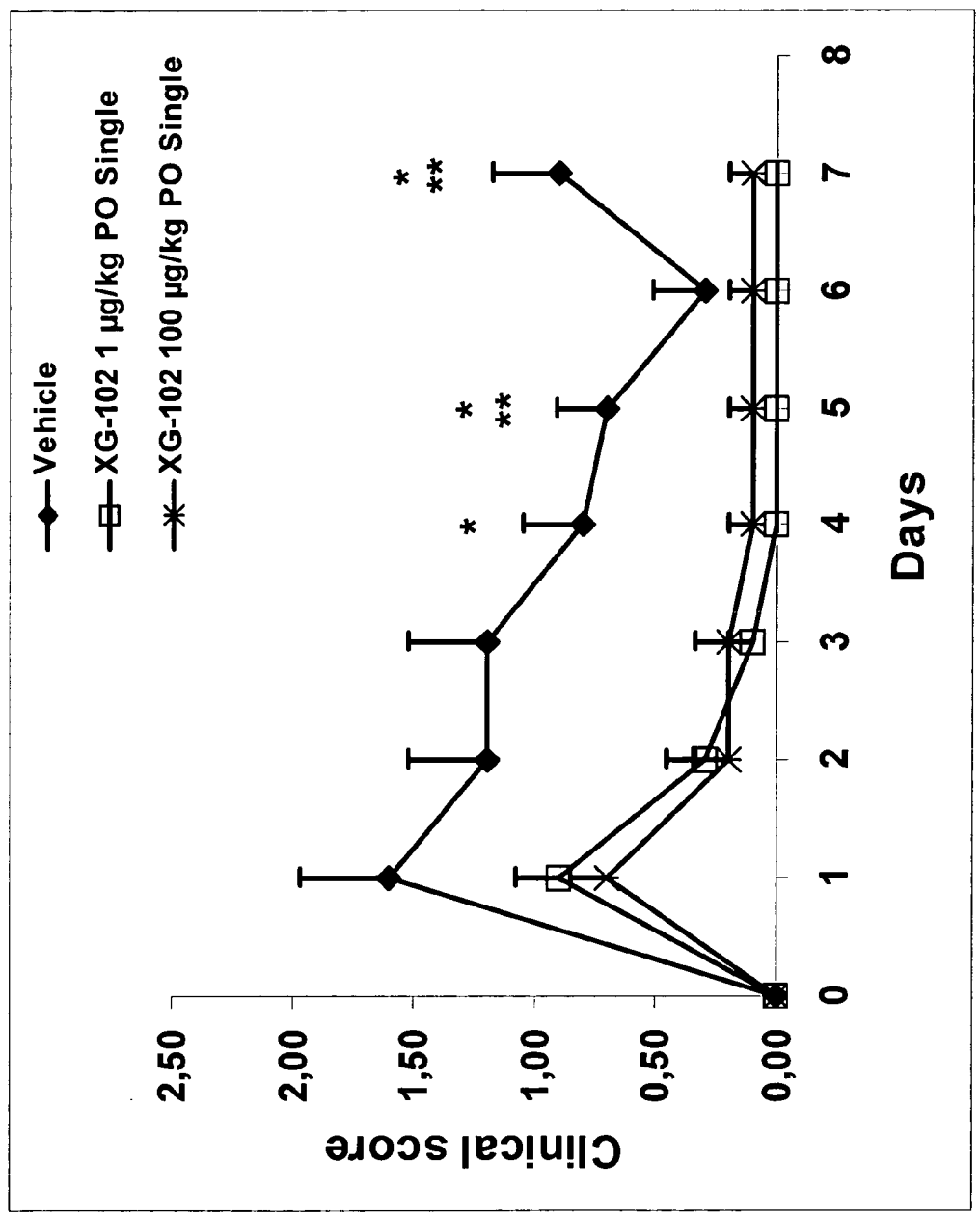
FIG. 7 shows the clinical scores upon treatment with XG-102 (SEQ ID NO: 11) in an IBD study with a treatment using XG-102 (single dose PO) in a concentration of 1 and 100 μg/kg PO as a single dose on day 0.
Figure 9:
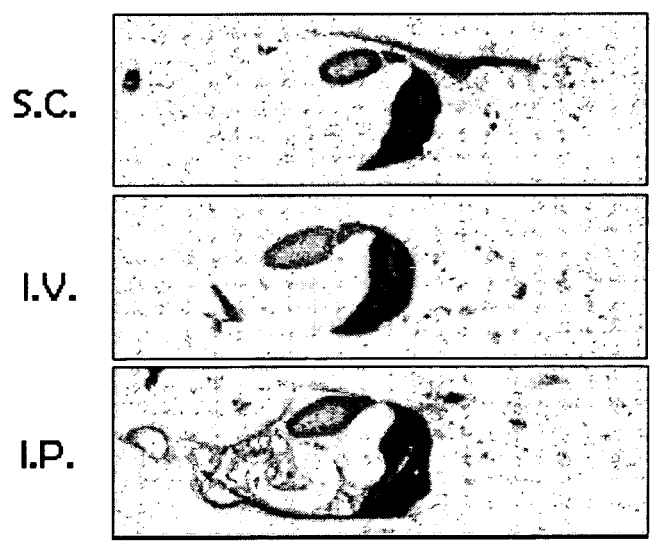
FIG. 9 Mice were treated via three different routes of administration (s.c., i.v., i.p.) with radiolabeled peptides with $C^{14}$ (1 mg/kg). Animals were sacrificed 72 hours after injection and processed for immunoradiography. Sagital sections were exposed and revealed the accumulation XG-102 peptides in the liver, spleen, and bone marrow predominantly (XG-102: SEQ ID NO: 11).
Figure 10:
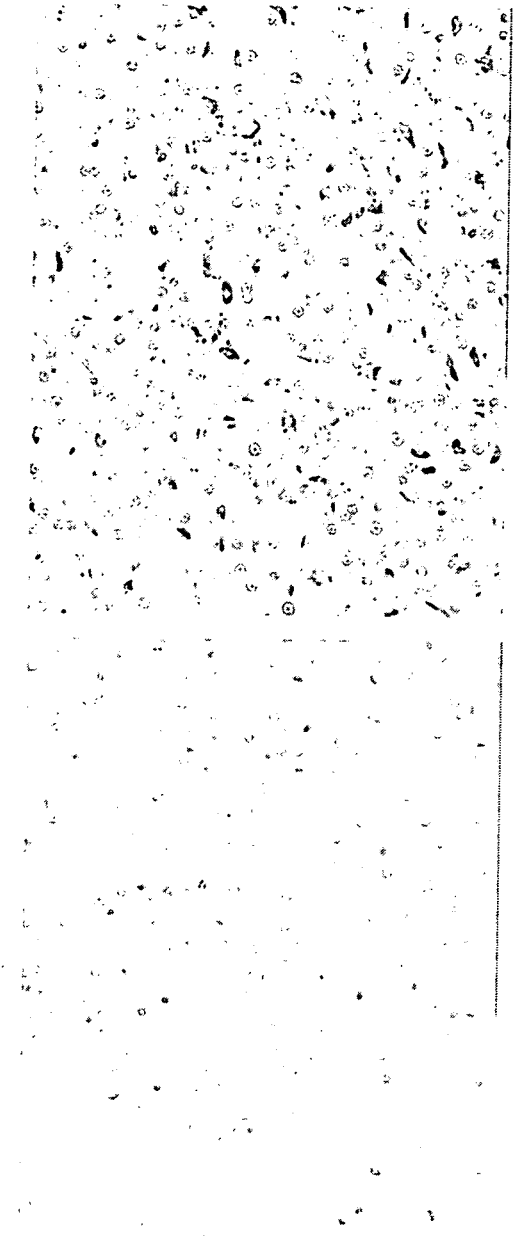
FIG. 10 shows an immunostaining against XG-102 (SEQ ID NO: 11) in the liver of rats injected with 1 mg/kg of XG-102 i.v. Animals were sacrificed 24 hours after injection. Revelation was done using DAB substrate. This figure shows again the pronounced accumulation of XG-102 in the liver, and especially, in the Kupffer cells (macrophages).
Figure 11:
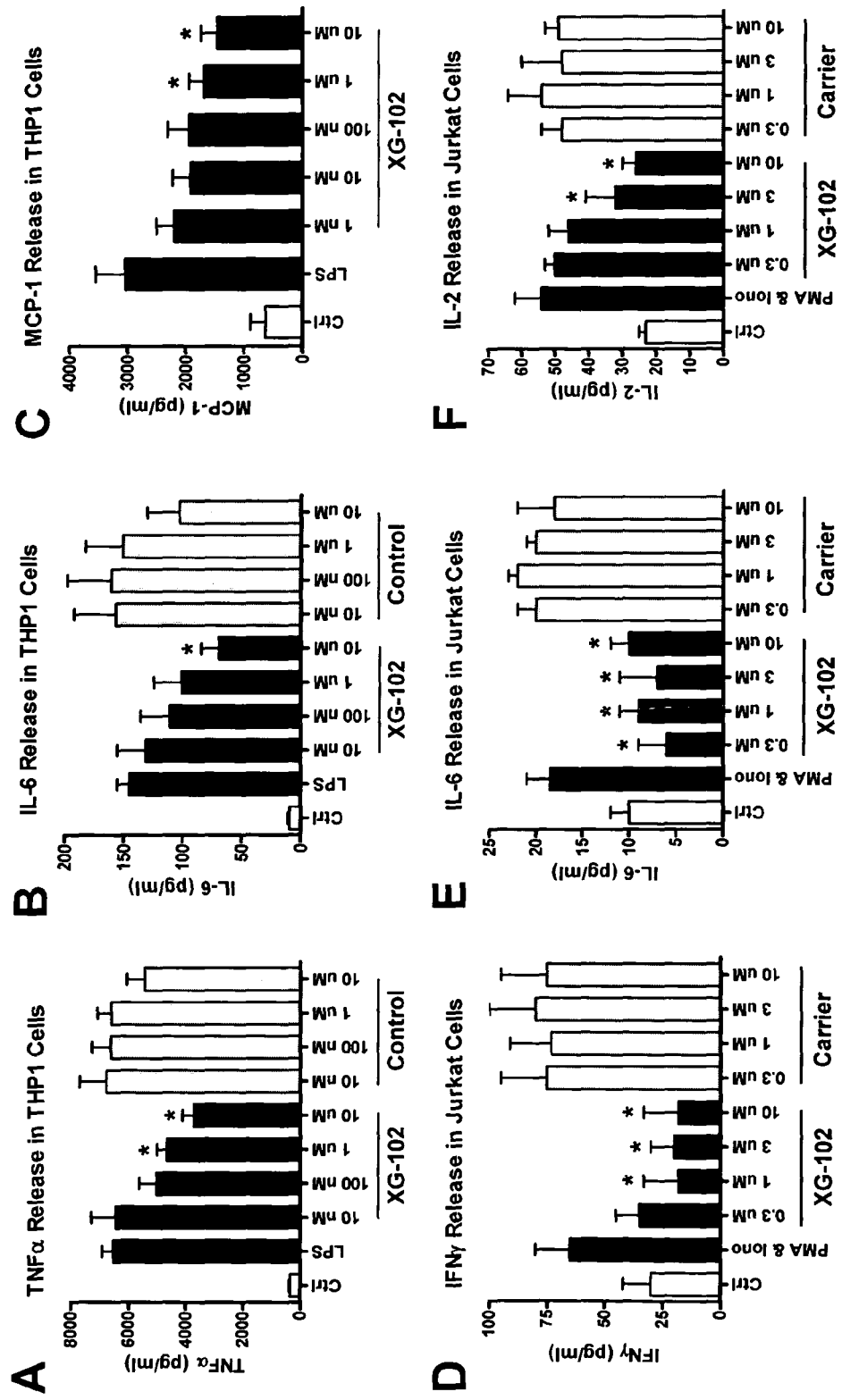
FIG. 11 shows the inhibition of Cytokine & Chemokine Release in two cell lines. XG-102 (SEQ ID NO:11) inhibits cytokine release in both myeloid and lymphoid cell lines, reducing LPS-induced TNFa, IL-6 and MCP-1 release in THP-1 cells (Panels A-C) and PMA & ionomycin-induced IFNg, IL-6 and IL-2 production in Jurkat cells (Panels D-F). The control (XG-101) is less effective due to its lesser stability.
Figure 12:
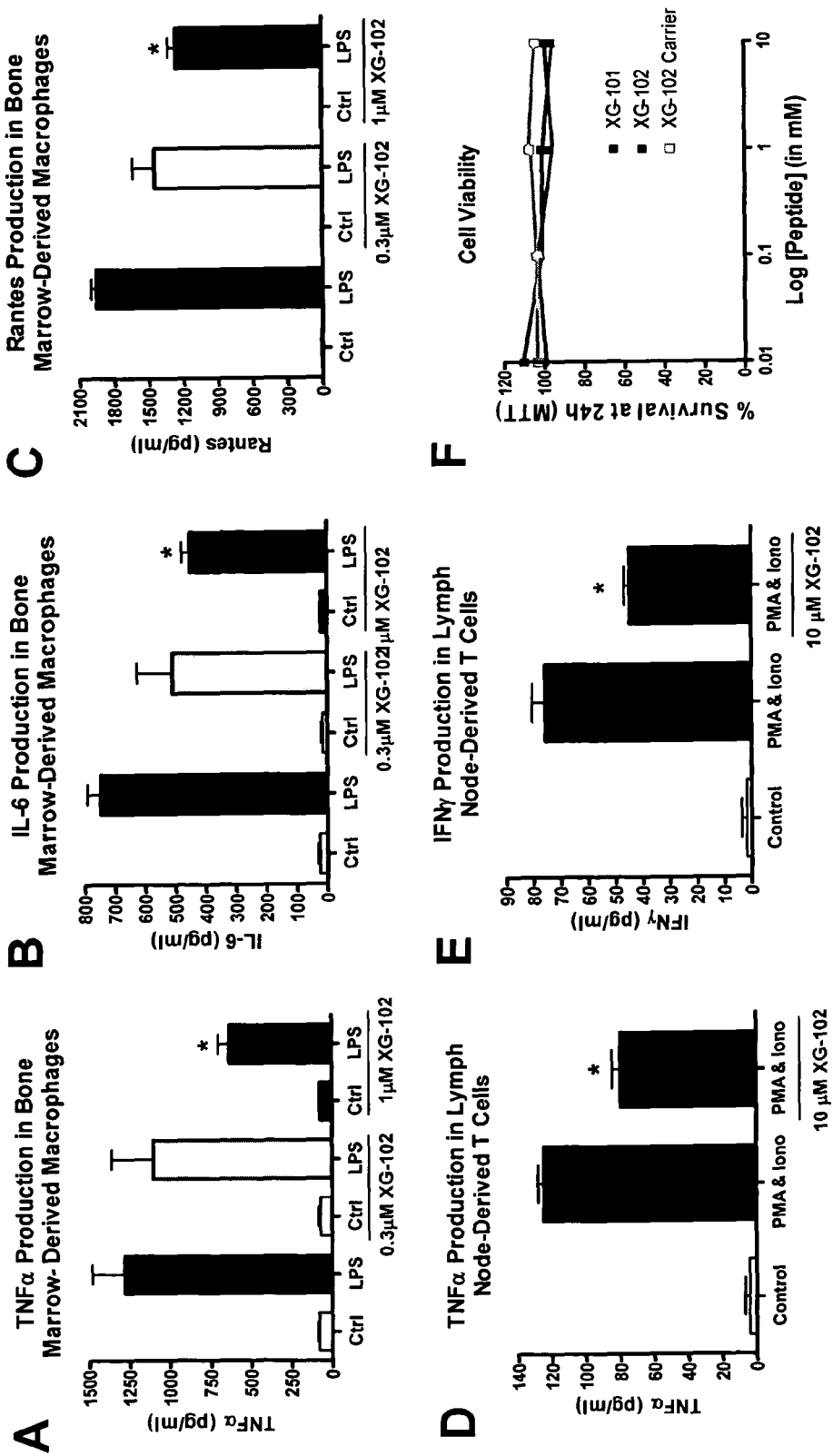
FIG. 12 shows the inhibition of cytokine release in primary cells. XG-102 (SEQ ID NO:11) also inhibits cytokine release in primary lymphoid and myeloid cells, reducing LPS-induced TNFa, IL-6 and Rantes release in murine macrophages (Panels A-C) and PMA & ionomycin-induced TNFa and IFNg production in murine T cells (Panels D-E). Effects occur at non-cytotoxic concentrations of XG-102 (Panel F)
Figure 13:
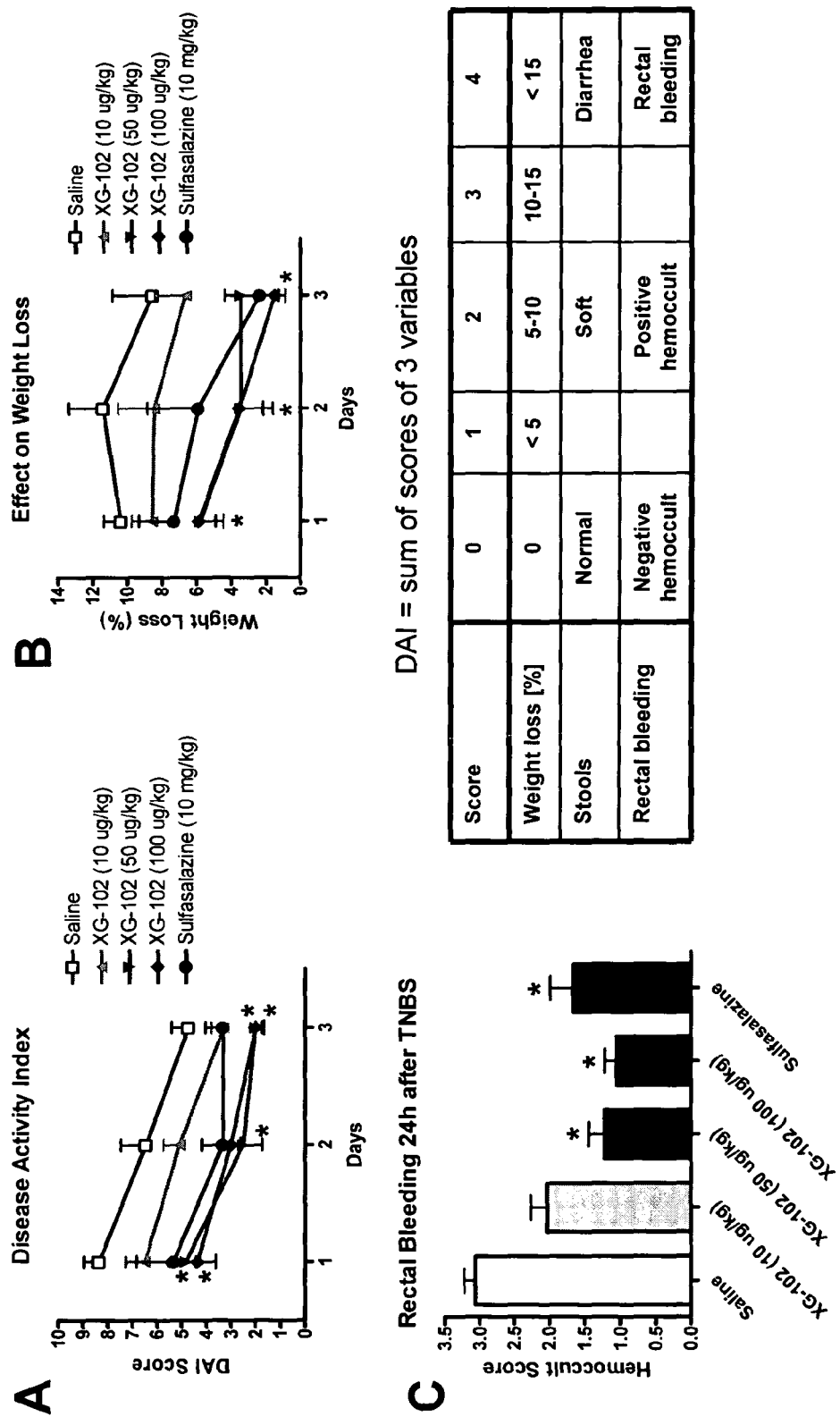
FIG. 13 shows the effect in TNBS-induced Colitis. JNK is activated in macrophages and lymphocytes of patients with inflammatory bowel disease, a response correlated with increased TNFa, IL-6 and IFNg production in lesions. Subcutaneous administration of 50 and 100 mg/kg XG-102 protects mice from TNBS-induced colitis (Panels A-C), diminishing DAI, weight loss and rectal bleeding.

Amino acid sequences important for efficient interaction with JNK were identified by sequence alignments between known JNK binding domain JBDs. A sequence comparison between the JBDs of IB1 [SEQ ID NO: 13], IB2 [SEQ ID NO: 14], c-Jun [SEQ ID NO: 15] and ATF2 [SEQ ID NO: 16] defined a weakly conserved 8 amino acid sequence (FIG. 1A). Since the JBDs of IB1 and IB2 are approximately 100 fold as efficient as c-Jun or ATF2 in binding JNK (Dickens et al. Science 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences.

These two blocks are contained within a peptide sequence of 19 amino acids in L-IB1(s) [SEQ ID NO: 1] and are also shown for comparative reasons in a 23 aa peptide sequence derived from IB1 [SEQ ID NO: 17]. These sequences are shown in FIG. 1B, dashes in the L-IB1 sequence indicate a gap in the sequence in order to align the conserved residues with L-IB1(s).

Example 2

Preparation of JNK Inhibitor Fusion Proteins

JNK inhibitor fusion proteins according to SEQ ID NO: 9 were synthesized by covalently linking the C-terminal end of SEQ ID NO: 1 to a N-terminal 10 amino acid long carrier peptide derived from the HIV-TAT4g 57 (Vives et al., J. Biol. Chem. 272: 16010 (1997)) according to SEQ ID NO: 5 via a linker consisting of two proline residues. This linker was used to allow for maximal flexibility and prevent unwanted secondary structural changes. The basic constructs were also prepared and designated L-IB1(s) (SEQ ID NO: 1) and L-TAT [SEQ ID NO: 5], respectively.

All-D retro-inverso peptides according to SEQ ID NO: 11 were synthesized accordingly. The basic constructs were also prepared and designated D-IB1(s) [SEQ ID NO: 2] and D-TAT [SEQ ID NO: 6], respectively.

All D and L fusion peptides according to SEQ ID NOs: 9, 10, 11 and 12 were produced by classical Fmock synthesis and further analysed by Mass Spectrometry. They were finally purified by HPLC. To determine the effects of the proline linker, two types of TAT peptide were produced one with and one without two prolines. The addition of the two prolines did not appear to modify the entry or the localization of the TAT peptide inside cells. Generic peptides showing the conserved amino acid residues are given in FIG. 2.

Example 3

Inhibition of Cell Death by JBD19

Effects of the 19 aa long JBD sequence of IB1(s) on JNK biological activities were studied. The 19 aa sequence was linked N-terminal to the Green Fluorescent Protein (GFP JBD19 construct), and the effect of this construct on pancreatic beta-cell apoptosis induced by IL1 was evaluated. This mode of apoptosis was previously shown to be blocked by transfection with $JBD_{1-280}$ whereas specific inhibitors of ERK½ or p38 did not protect (see Ammendrup et al., supra).

Oligonucleotides corresponding to JBD19 and comprising a conserved sequence of 19 amino acids as well as a sequence mutated at the fully conserved regions were synthesized and directionally inserted into the EcoRI and SalI sites of the pEGFP-N1 vector encoding the Green Fluorescent Protein (GFP) (from Clontech). Insulin producing TC-3 cells were cultured in RPMI 1640 medium supplemented with 10% Fetal Calf Serum, 100 µg/mL Streptomycin, 100 units/mL Penicillin and 2 mM Glutamine. Insulin producing TC-3 cells were transfected with the indicated vectors and IL-1 (10 ng/mL) was added to the cell culture medium. The number of apoptotic cells was counted at 48 hours after the addition of IL-1 using an inverted fluorescence microscope. Apoptotic cells were discriminated from normal cells by the characteristic "blebbing out" of the cytoplasm and were counted after two days.

GFP is Green Fluorescent protein expression vector used as a control; JBD19 is the vector expressing a chimeric GFP linked to the 19 aa sequence derived from the JBD of IB1; JBD19Mut is the same vector as GFP-JBD19, but with a JBD mutated at four conserved residues shown as FIG. 1B; and $JBD_{1-280}$ is the GFP vector linked to the entire JBD (aa 1-280). The GFP-JBD19 expressing construct prevented IL-1 induced pancreatic-cell apoptosis as efficiently as the entire $JBD_{1-280}$.

As additional controls, sequences mutated at fully conserved IB1(s) residues had greatly decreased ability to prevent apoptosis.

Example 4

Cellular Import of TAT-IB1(s) Peptides

The ability of the L- and D-enantiomeric forms of TAT and TAT-IB1(s) peptides ("TAT-IB peptides") to enter cells was evaluated. L-TAT, D-TAT, L-TAT-IB1(s), and D-TAT-IB1(s) peptides [SEQ ID NOS: 5, 6, 9 and 12, respectively] were labeled by N-terminal addition of a glycine residue conjugated to fluorescein. Labeled peptides (1 µM) were added to TC-3 cell cultures, which were maintained as described in Example 3. At predetermined times cells were washed with PBS and fixed for five minutes in ice-cold methanol-acetone (1:1) before being examined under a fluorescence microscope. Fluorescein-labeled BSA (1 µM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 µM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and D-TAT-IB1(s) were extremely stable inside the cells.

Fluorescent signals from these all-D retro-inverso peptides were still very strong 1 week later, and the signal was only slightly diminished at 2 weeks post treatment.

Example 5

In Vitro Inhibition of c-JUN, ATF2 and Elk1 Phosphorylation

The effects of the peptides on JNKs-mediated phosphorylation of their target transcription factors were investigated in vitro. Recombinant and non activated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein L-TAT or L-TAT-IB1(s) peptides (0-25 µM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM $MgCl_2$ and 5 pCi $^{33}$P-dATP and 1 µg of either GST-Jun (aa 1-89), GST-AFT2 (aa 1-96) or GST-ELK1 (aa 307-428). GST-fusion proteins were purchased from Stratagene (La Jolla, Calif.).

Ten µL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at TAT-IB(s) peptide doses as low as 2.5 µM. However, a marked exception was the absence of TAT-IB(s) inhibition of JNK3 phosphorylation of Elk1. Overall, the TAT-IB1(s) peptide showed superior effects in inhibiting JNK family phosphorylation of their target transcription factors. The ability of D-TAT, D-TAT-IB1(s) and L-TAT-IB1(s) peptides (0-250 µM dosage study) to inhibit GST-Jun (aa 1-73) phosphorylation by recombinant JNK1, JNK2, and JNK3 by were analyzed as described above. Overall, D-TAT-IB1(s) peptide decreased JNK-mediated phosphorylation of c-Jun, but at levels approximately 10-20 fold less efficiently than L-TAT-IB1(s).

Example 6

Inhibition of c-JUN Phosphorylation by Activated JNKs

The effects of the L-TAT or L-TAT-IB1(s) peptides as defined herein on JNKs activated by stressful stimuli were evaluated using GST-Jun to pull down JNKs from UV-light irradiated HeLa cells or IL-1 treated PTC cells. PTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, PTC cells were activated with IL-1 as described above, whereas HeLa cells were activated by UV-light (20 J/m$^2$). Cell extracts were prepared from control, UV-light irradiated HeLa cells and IL-1 treated TC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mMP-glycerophosphate, 1 mM dithiothreitol). Debris were removed by centrifugation for five minutes at 15,000 rpm in an SS-34 Beckman rotor. One-hundred μg extracts were incubated for one hour at room temperature with one μg GST-jun (amino acids 1-89) and 10 μL of glutathione-agarose beads (Sigma). Following four washes with the scraping buffer, the beads were resuspended in the same buffer supplemented with L-TAT or L-TAT-IB1(s) peptides (25 μM) for 20 minutes. Kinase reactions were then initiated by addition of 10 mM MgCl$_2$ and 5 pCi $^{33}$P-gamma-dATP and incubated for 30 minutes at 30° C.

Reaction products were then separated by SDS-PAGE on a denaturing 10% polyacrylamide gel. Gels were dried and subsequently exposed to X-ray films (Kodak). The TAT-IB(s) peptides efficiently prevented phosphorylation of c-Jun by activated JNKs in these experiments.

Example 7

In Vivo Inhibition of c-JUN Phosphorylation by TAT-Ib(s) Peptides as Defined Herein To determine whether the cell-permeable peptides as defined herein could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (see Whitmarsh et al, Science 285: 1573 (1999)). Briefly, 3×10$^5$ cells were transfected with the plasmids in 3.5-cm dishes using DOTAP (Boehringer Mannheim) following instructions from the manufacturer. For experiments involving GAL-Jun, 20 ng of the plasmid was transfected with 1 μg of the reporter plasmid pFR-Luc (Stratagene) and 0.5 μg of either MKK4 or MKK7 expressing plasmids. Three hours following transfection, cell media were changed and TAT and TAT-IB1(s) peptides (1 μM) were added. The luciferase activities were measured 16 hours later using the "Dual Reporter System" from Promega after normalization to protein content. Addition of TAT-IB1(s) peptide blocked activation of c-Jun following MKK4 and MKK7 mediated activation of JNK. Because HeLa cells express JNK1 and JNK2 isoforms but not JNK3, we transfected cells with JNK3. Again, the TAT-IB(s) peptide inhibited JNK2 mediated activation of c-Jun.

Example 8

Synthesis of all-D Retro-Inverso IB(s) Peptides and Variants Thereof

Peptides of the invention may be all-D amino acid peptides synthesized in reverse to prevent natural proteolysis (i.e. all-D retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO: 5], the retro-inverso peptide analog of this peptide (formed of D-amino acids) would have the sequence RRRQRRKKRG [SEQ ID NO: 6]. The procedures for synthesizing a chain of D-amino acids to form the retro-inverso peptides are known in the art (see e.g. Jameson et al, Nature, 368, 744-746 (1994); Brady et al., Nature, 368, 692-693 (1994); Guichard et al., J. Med. Chem. 39, 2030-2039 (1996)). Specifically, the retro-peptides according to SEQ ID NOs 2, 4, 6, 8, 11-12, 18, 20, 22 and 25-26, were produced by classical F-mock synthesis and further analyzed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 9

Long Term Biological Activity of all-D Retro-Inverso IB(s) Peptides and Variants Thereof Long term biological activity is predicted for the D-TAT-IB(s) retro-inverso containing peptide heteroconjugate (see chimeric sequences above) when compared to the native L-amino acid analog owing to protection of the D-TAT-IB(s) peptide from degradation by native proteases, as shown in Example 5.

Inhibition of IL-1 induced pancreatic beta-cell death by the D-TAT-IB1(s) peptide was analyzed. TC-3 cells were incubated as described above for 30 minutes with one single addition of the indicated peptides (1, μM), then IL-1 (10 ng/ml) was added.

Apoptotic cells were then counted after two days of incubation with IL-1 by use of Propidium Iodide and Hoechst 33342 nuclear staining. A minimum of 1,000 cells were counted for each experiment. The D-TAT-IB1 peptide decreased IL-1 induced apoptosis to a similar extent as L-TAT-IB peptides.

Long term inhibition of IL-1P induced cell-death by the D-TAT-IB1 peptide was also analyzed. TC-3 cells were incubated as above for 30 minutes with one single addition of the indicated peptides (1 μM), then IL-1 (10 ng/ml) was added, followed by addition of the cytokine every two days. Apoptotic cells were then counted after 15 days of incubation with IL-1 by use of propidium iodide and Hoechst 33342 nuclear staining. Note that one single addition of the TAT-IB1 peptide does not confer long-term protection. A minimum of 1.000 cells were counted for each experiment. As a result, D-TAT-IB1(s), but not L-TAT-IB1(s), was able to confer long term (15 day) protection.

Example 10

Suppression of JNK Transcription Factors by L-TAT-IB1(s) Peptides as Used According to the Present Invention Gel retardation assays were carried out with an AP-1 doubled labeled probe (5'-CGC TTG ATG AGT CAG CCG GAA-3' (SEQ ID NO: 101). HeLa cell nuclear extracts that were treated or not for one hour with 5 ng/mlTNF-, as indicated. TAT and L-TAT-IB1(s) peptides as used according to the present invention were added 30 minutes before TNF-alpha. Only the part of the gel with the specific AP-1 DNA complex (as demonstrated by competition experiments with non-labeled specific and non-specific competitors) is shown.

L-TAT-IB1(s) peptides as used according to the present invention decrease the formation of the AP-1 DNA binding complex in the presence of TNF-alpha.

Example 11

Inhibition of Endogenous JNK Activity in HepG2 Cells Using an all-in One Well Approach HepG2 cells were seeded at 3'000 cells/well the day prior the experiment. Then, increasing concentrations of either interleukin-1 [IL-1beta)] or tumor necrosis factor [TNFalpha)] (a) were added to activate JNK for 30 minutes. Cells were lysed in 20 mM Hepes, 0.5% Tween pH 7.4 and processed for AlphaScreen JNK. (b) Z' for the JNK activity induced by 10 ng/ml IL-1 and measured in 384 wells/plate (n=96). (c) Inhibition of endogenous IL-1 beta-induced JNK activity with chemical JNK inhibitors [staurosporin and SP600125]. (d) Effect of peptidic inhibitors L-TAT-IB1(s) according to SEQ ID NO: 9 [here abbreviated as L-JNKi] and D-TAT-IB1(s) according to SEQ ID NO: 11 (here abbreviated as D-JNKi) and JBDs) (corresponds to L-JNKI without the TAT sequence)] on IL-1 dependent JNK activity. All panels are representative of three independent experiments (n=3).

Methods: Alphascreen Kinase Assay

Principle: AlphaScreen is a non-radioactive bead-based technology used to study biomolecular interactions in a microplate format. The acronym ALPHA stands for Amplified Luminescence Proximity Homogenous Assay. It involves a biological interaction that brings a "donor" and an "acceptor" beads in close proximity, then a cascade of chemical reactions acts to produce an amplified signal. Upon laser excitation at 680 nm, a photosensitizer (phthalocyanine) in the "donor" bead converts ambient oxygen to an excited singlet state. Within its 4 μsec half-life, the singlet oxygen molecule can diffuse up to approximately 200 nm in solution and if an acceptor bead is within that proximity, the singlet oxygen reacts with a thioxene derivative in the "acceptor" bead, generating chemiluminescence at 370 nm that further activates fluorophores contained in the same "acceptor" bead. The excited fluorophores subsequently emit light at 520-620 nm. In the absence of an acceptor bead, singlet oxygen falls to ground state and no signal is produced.

Kinase reagents (B-GST-cJun, anti P-cJun antibody and active JNK3) were first diluted in kinase buffer (20 mM Tris-HCl pH 7.6, 10 mM $MgCl_2$, 1 mM DTT, 100 μM $Na_3VO_4$, 0.01% Tween-20) and added to wells (15 μl). Reactions were then incubated in presence of 10 μM of ATP for 1 h at 23° C. Detection was performed by an addition of 10 μl of beads mix (Protein A acceptor 20 μg/ml and Streptavidin donor 20 μg/ml), diluted in detection buffer (20 mM Tris-HCl pH 7.4, 20 mM NaCl, 80 mM EDTA, 0.3% BSA), followed by an another one-hour incubation at 23° C. in the dark. For measurement of JNK endogenous activity, kinase assays were performed as described above except active JNK3 was replaced by cells lysates and reaction kinase components were added after the cells lysis. B-GST-cjun and P-cJun antibody were used at the same concentrations whereas ATP was used at 50 μM instead of 10 μM. AlphaScreen signal was analyzed directly on the Fusion or En Vision apparatus.

Example 12

Evaluation of the Therapeutical Activity of D- and L-TAT-IB1(s) Peptides as Used According to the Present Invention a) Test system:
i) Species/Strain: Mouse/BALB/c
ii) Source: Harlan Israel, Ltd.
iii) Gender: Female
iv) Total No. of Animals: n=150
v) Age: Young adults, 7 weeks of age at study initiation
vi) Body Weight: Weight variation of animals at the time of treatment initiation does not exceed ±20% of the mean weight.
vii) Animals Health: The health status of the animals used in this study is examined on arrival, only animals in good health are acclimatized to laboratory conditions (at least seven days) and are used in the study.
viii) Randomization: Animals are randomly assigned to experimental groups according to a Table of Random Numbers.
ix) Termination: At the end of the study surviving animals are euthanized by cercical dislocation.

b) Constitution of test groups and dose levels

The table below lists the experimental groups comprising the study.

| Group # | Group size | Test Item | Route | Dose | Volume (ml/kg) | Regime |
|---|---|---|---|---|---|---|
| 1F | N = 10 | Vehicle | PO | 0 | 5 | Once daily for 7 days |
| 2F | N = 10 | Sulfasalazine | PO | 10 mg/kg | 5 | Once daily for 7 days |
| 3F | N = 10 | Remicade | IP | 5 mg/kg | 5 | Once daily for 7 days |
| 4F | N = 10 | XG-102 | SC | 0.01 μg/kg | 5 | Once daily for 7 days |
| 5F | N = 10 | XG-102 | SC | 0.1 μg/kg | 5 | Once daily for 7 days |
| 6F | N = 10 | XG-102 | SC | 1 μg/kg | 5 | Once daily for 7 days |
| 7F | N = 10 | XG-102 | SC | 10 μg/kg | 5 | Once daily for 7 days |

-continued

| Group # | Group size | Test Item | Route | Dose | Volume (ml/kg) | Regime |
|---|---|---|---|---|---|---|
| 8F | N = 10 | XG-102 | SC | 100 μg/kg | 5 | Once daily for 7 days |
| 9F | N = 10 | XG-102 | SC | 1000 μg/kg | 5 | Once daily for 7 days |
| 10F | N = 10 | XG-102 | SC | 1 μg/kg | 5 | Single dose |
| 11F | N = 10 | XG-102 | SC | 100 μg/kg | 5 | Single dose |
| 12F | N = 10 | XG-102 | PO | 1 μg/kg | 5 | Once daily for 7 days |
| 13F | N = 10 | XG-102 | PO | 100 μg/kg | 5 | Once daily for 7 days |
| 14F | N = 10 | XG-102 | PO | 1 μg/kg | 5 | Single dose |
| 15F | N = 10 | XG-102 | PO | 100 μg/kg | 5 | Single dose |

XG-102 = SEQ ID NO: 11
IP = intraperitoneal administration
PO = peroral administration
SC = subcutaneous administration c) Test Procedures Colitis was induced by administration of TNBS dissolved in 50% Ethanol All animals were then treated with doses of XG-102 in the range of 0.1 to 1000 μg/kg, either intraperitoneally or subcutaneously, as a single or repeated daily doses (see above).

d) Observations and Examinations i) Clinical signs

Throughout the duration of the above experiment, careful clinical examinations were carried out and recorded. Observations included changes external appearance, e.g. of the skin, fur, eyes, mucous membranes, occurrence of secretions and excretions (e.g. diarrhea), and autonomic activity. Changes in gait, posture and response to handling, as well as the presence of bizarre behavior, tremors, convulsions, sleep and coma were also noted.

ii) Body weights

Determination of individual body weight of animals was made on a daily basis.

iii) Clinical assessment of colitis

Body weight, stool consistency and bleeding per rectum were all recorded daily and served as the parameters of disease severity score:

| Score | Weight loss (%) | Stool consistency | Presence of blood per rectum |
|---|---|---|---|
| 0 | None | Normal | Negative |
| 1 | 1-5 | Redness, swelling of the anus | Negative |
| 2 | 5-10 | Loose stool | Negative |
| 3 | 10-15 | Diarrhea | Negative |
| 4 | >15 | Diarrhea | Bleeding |
| 5 | | Death | | iv) Gross pathology of the colon

On the last day of the experiment, animals were euthanized and the colon was removed for gross pathology evaluation according to the following score:

| Grade | Signs |
|---|---|
| 0 | No abnormalities detected |
| 1 | Edema and redness on one location |

-continued

| Grade | Signs |
|---|---|
| 2 | Edema and redness on more than one location, or a very massive endema and redness capture more than 50% of the colon |
| 3 | One ulcer |
| 4 | More than one ulcer or a very long severe ulcer | e) Results i) Clinical signs

No abnormalities were observed during clinical examinations following the treatment with XG-102 (SEQ ID NO: 11).

ii) Mortality rate

No mortality was recorded.

iii) Body weights

TNBS induced a significant weight loss on day 1. XG-102 (SEQ ID NO: 11) administration either prevented the weight loss or ameliorated the symptoms and supported recovery.

iv) Clinical score

TNBS injected vehicle treated animals reached a maximum score on study day 1 and recovered fully only on or after study day 5. FIG. 3 shows that Sulfasalazine treatment resulted in reduction in the clinical score. FIGS. 3-7 demonstrate that XG-102 (SEQ ID NO: 11), administered using any dose, route or time schedule as defined above (single dose or daily dose) resulted in an effect equivalent to or better than the one observed with the commonly used reference drug sulfasalazine.

v) Cross pathology score

Gross analysis at the end of the study revealed that the TNBS injected vehicle treated animals were injured with edema and ulcers along the colon. Sulfasalazine was effective in reducing the gross pathology completely.

vi) Colon length

No effect of disease induction or treatment was observed on colon length.

vii) Colon weight

No effect of disease induction or treatment was observed on colon weight.

f) Conclusions

In view of the above findings obtained under the conditions of the above experiment and confined to the in-life data, the exemplary sequence XG-102 according to SEQ ID NO: 11 administered either SC or PO was active in enhancing diseases recovery.

Example 13

Preferred Embodiments

In the following, some preferred embodiments according to the present invention are listed:
1. Use of a JNK inhibitor sequence comprising less than 150 amino acids in length for the preparation of a pharmaceutical composition for treating chronic or non-chronic inflammatory digestive diseases in a subject.
2. The use of a JNK inhibitor sequence according to embodiment 1, wherein the JNK inhibitor sequence is derived from a human or rat IB1 sequence as defined or encoded by any of sequences according to SEQ ID NO: 102, SEQ ID NO: 103, SEQ ID NO: 104 or SEQ ID NO: 105 or from a fragment or variant thereof.
3. The use of a JNK inhibitor sequence according to embodiment 1 or 2, wherein the JNK inhibitor sequence comprises a range of 5 to 150 amino acid residues, more preferably 10 to 100 amino acid residues, even more preferably 10 to 75 amino acid residues and most preferably a range of 10 to 50 amino acid residues.
4. The use of a JNK inhibitor sequence of any of embodiments 1 to 3, wherein the JNK inhibitor sequence binds c-jun amino terminal kinase (JNK).
5. The use of a JNK inhibitor sequence of any of embodiments 1 to 4, wherein the JNK inhibitor sequence inhibits the activation of at least one JNK targeted transcription factor when the JNK inhibitor sequence is present in a JNK expressing cell.
6. The use of a JNK inhibitor sequence of any of embodiments 1 to 5, wherein the JNK targeted transcription factor is selected from the group consisting of c-Jun, ATF2, and Elk1.
7. The use of a JNK inhibitor sequence of any of embodiments 1 to 6, wherein the JNK inhibitor sequence alters a JNK effect when the peptide is present in a JNK expressing cell.
8. The use of a JNK inhibitor sequence of any of embodiments 1 to 7, wherein the JNK inhibitor sequence is composed of L-amino acids, D-amino acids, or a combination of both, preferably comprises at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK inhibitor sequences in a blockwise, a non-blockwise or in an alternate manner.
9. The use of a JNK inhibitor sequence of any of embodiments 1 to 8, wherein the inhibitor sequence comprises or consists of at least one amino acid sequence according to SEQ ID NOs: 1 to 4, 13 to 20 and 33 to 100, or a fragment, derivative or variant thereof.
10. Use of a chimeric peptide comprising at least one first domain and at least one second domain linked by a covalent bond, the first domain comprising a trafficking sequence, and the second domain comprising a JNK inhibitor sequence as defined in any of embodiments 1 to 9 for the preparation of a pharmaceutical composition for treating chronic or non-chronic inflammatory digestive diseases in a subject.
11. The use of the chimeric peptide of embodiment 10, wherein the chimeric peptide is composed of L-amino acids, D-amino acids, or a combination of both, preferably comprises at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the chimeric peptide in a blockwise, a non-blockwise or in an alternate manner.
12. The use of the chimeric peptide of embodiment 10 or 11, wherein the trafficking sequence comprises the amino acid sequence of a human immunodeficiency virus TAT polypeptide.
13. The use of the chimeric peptide of any of embodiments 10 to 12, wherein the trafficking sequence consists of or comprises the amino acid sequence of SEQ ID NO: 5, 6, 7, 8, 21 or 22.
14. The use of the chimeric peptide of any of embodiments 10 to 13, wherein the trafficking sequences augments cellular uptake of the peptide.
15. The use of the chimeric peptide of any of embodiments 10 to 14, wherein the trafficking sequence directs nuclear localization of the peptide.
16. The use of the chimeric peptide of any of embodiments 10 to 15, wherein the chimeric peptide consists of or comprises the amino acid sequence of any of SEQ ID NOs: 9 to 12 and 23 to 32, or a fragment, or variant thereof.
17. Use of an isolated nucleic acid encoding a JNK inhibitor sequence as defined in any of embodiments 1 to 9 or a chimeric peptide as defined in any of embodiments 10 to 16 for the preparation of a pharmaceutical composition for treating chronic or non-chronic inflammatory digestive diseases in a subject.
18. Use of a vector comprising the nucleic acid as defined in embodiment 17 for the preparation of a pharmaceutical composition for treating chronic or non-chronic inflammatory digestive diseases in a subject.
19. Use of a cell comprising the vector as defined in embodiment 18 for the preparation of a pharmaceutical composition for treating chronic or non-chronic inflammatory digestive diseases in a subject.
20. Use of an antibody which binds immunospecifically to a JNK inhibitor sequence according to any of embodiments 1 to 9 or to a chimeric peptide according to any of embodiments 10 to 16 for the preparation of a pharmaceutical composition for treating chronic or non-chronic inflammatory digestive diseases in a subject.
21. Use according to any of the preceding embodiments, wherein the pharmaceutical composition is to be administered by an administration route selected from the group consisting of parenteral routes, including intravenous, intramuscular, subcutaneous, intradermal, transdermal, enteral routes, including orally, rectally, topical routes, including nasal, intranasal, and other routes, including epidermal or patch delivery.
22. Use according to any of the preceding embodiments, wherein the non-chronic or chronic inflammatory diseases are selected from diseases of the gastrointestinal tract including diseases of the esophagus, stomach, first, second and third part of the duodenum, jejunum, ileum, the ileocecal complex, large intestine, of the ascending, transverse and descending colon sigmoid colon and rectum, chronic inflammatory digestive diseases, characterized by an inflammation of the colon, including colitis, selected from Colitis ulcerosa (ulcerative colitis), Morbus Crohn (Crohn's disease), diversion colitis, ischemic colitis, infectious colitis, fulminant colitis, chemical colitis, microscopic colitis, lymphocytic colitis, collageneous colitis, indeterminate colitis and atypical colitis.

The invention claimed is:

1. A method of treating Crohn's disease in a mammalian subject, the method comprising administering a pharmaceutical composition to the subject in need of treatment thereof, the composition comprising a c-Jun N-terminal kinase (JNK) specific inhibitor consisting of having an amino acid sequence with at least 95% sequence identity to SEQ ID NO: 11.

2. The method of claim 1, wherein the JNK inhibitor binds JNK.

3. The method of claim 1, wherein the JNK inhibitor inhibits the activation of at least one JNK targeted transcription factor when the JNK inhibitor is present in a JNK expressing cell.

4. The method of claim 3, wherein the JNK targeted transcription factor is selected from the group consisting of c-Jun, ATF2, and Elk1.

5. The method of claim 1, wherein the JNK inhibitor alters a JNK effect when the peptide is present in a JNK expressing cell.

6. The method of claim 1, wherein the JNK inhibitor is composed of D-amino acids.

7. The method of claim 1, wherein the pharmaceutical composition is to be administered by intravenous administration.

8. The method of claim 1, wherein the JNK inhibitor comprises a JNK binding domain that binds JNK.

9. The method of claim 1, wherein the JNK inhibitor comprises a JNK binding domain that inhibits the activation of at least one JNK targeted transcription factor when the JNK inhibitor is present in a JNK expressing cell.

10. The method of claim 9, wherein the JNK targeted transcription factor is selected from the group consisting of c-Jun, ATF2, and Elk1.

11. The method of claim 1, wherein the JNK inhibitor alters a JNK effect when the amino acid sequence is present in a JNK expressing cell.

* * * * *

SEQUENCE LISTING

<160> NUMBER OF SEQ ID NOS: 105

<210> SEQ ID NO 1
<211> LENGTH: 19
<212> TYPE: PRT
<213> ORGANISM: Artificial
<220> FEATURE:
<223> OTHER INFORMATION: Description of sequence: Peptide L-IB1(s) (see Table 1)

<400> SEQUENCE: 1

Arg Pro Lys Arg Pro Thr Thr Leu Asn Leu Phe Pro Gln Val Pro Arg
1               5                   10                  15

Ser Gln Asp

<210> SEQ ID NO 2
<211> LENGTH: 19
<212> TYPE: PRT
<213> ORGANISM: Artificial
<220> FEATURE:
<223> OTHER INFORMATION: Description of sequence: Peptide D-IB1(s) (see Table 1)
<220> FEATURE:
<221> NAME/KEY: MUTAGEN
<222> LOCATION: (1)..(19)
<223> OTHER INFORMATION: all amino acids are D-amino acids

<400> SEQUENCE: 2

Asp Gln Ser Arg Pro Val Gln Pro Phe Leu Asn Leu Thr Thr Pro Arg
1               5                   10                  15

Lys Pro Arg

<210> SEQ ID NO 3
<211> LENGTH: 19
<212> TYPE: PRT
<213> ORGANISM: Artificial
<220> FEATURE:
<223> OTHER INFORMATION: Description of sequence: Peptide L-IB (generic) (s) (see Table 1)
<220> FEATURE:
<221> NAME/KEY: misc_feature
<223> OTHER INFORMATION: Description of sequence: Description of sequence: general formula: NH2-Xnb-Xna-RPTTLXLXXXXXXXQD-Xnb-COOH (see Table 1)
<220> FEATURE:
<221> NAME/KEY: VARIANT
<222> LOCATION: (1)..(1)
<223> OTHER INFORMATION: Xaa is Xnb as defined in the general formula, wherein Xaa represents an amino acid residue, preferably selected from any (native) amino acid residue;
<220> FEATURE:
<221> NAME/KEY: REPEAT
<222> LOCATION: (1)..(1)
<223> OTHER INFORMATION: Xaa is Xnb as defined in the general formula, wherein n is 0-5, 5-10, 10-15, 15-20, 20-30 or more for Xnb
<220> FEATURE:
<221> NAME/KEY: VARIANT
<222> LOCATION: (2)..(2)
<223> OTHER INFORMATION: Xaa is Xna as defined in the general formula, wherein Xaa represents an amino acid residue, preferably selected from any (native) amino acid residue residue except serine and threonine
<220> FEATURE:
<221> NAME/KEY: REPEAT
<222> LOCATION: (2)..(2)
<223> OTHER INFORMATION: Xaa is Xna as defined in the general formula, wherein n is 0 or 1
<220> FEATURE:
<221> NAME/KEY: VARIANT
<222> LOCATION: (8)..(8)
<223> OTHER INFORMATION: Xaa represents an amino acid residue, preferably selected from any (native) amino acid residue;

```
<220> FEATURE:
<221> NAME/KEY: VARIANT
<222> LOCATION: (10)..(16)
<223> OTHER INFORMATION: Xaa represents an amino acid residue,
      preferably selected from any (native) amino acid residue;
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;

<400> SEQUENCE: 3

Xaa Xaa Arg Pro Thr Thr Leu Xaa Leu Xaa Xaa Xaa Xaa Xaa Xaa Xaa
1               5                   10                  15

Gln Asp Xaa

<210> SEQ ID NO 4
<211> LENGTH: 19
<212> TYPE: PRT
<213> ORGANISM: Artificial
<220> FEATURE:
<223> OTHER INFORMATION: Description of sequence: Peptide D-IB (generic)
      (s) (see Table 1)
<220> FEATURE:
<221> NAME/KEY: misc_feature
<223> OTHER INFORMATION: Description of sequence: general formula:
      NH2-Xnb-DQXXXXXXXLXLTTPR-Xna-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (4)..(10)
<223> OTHER INFORMATION: Xaa represents an amino acid residue,
      preferably selected from any (native) amino acid residue;
<220> FEATURE:
<221> NAME/KEY: VARIANT
<222> LOCATION: (12)..(12)
<223> OTHER INFORMATION: Xaa represents an amino acid residue,
      preferably selected from any (native) amino acid residue;
<220> FEATURE:
<221> NAME/KEY: REPEAT
<222> LOCATION: (18)..(18)
<223> OTHER INFORMATION: Xaa is Xna as defined in the general formula,
      wherein n is 0 or 1
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
      Threonine
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
```

```
            threonine
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;

<400> SEQUENCE: 4

Xaa Asp Gln Xaa Xaa Xaa Xaa Xaa Xaa Xaa Leu Xaa Leu Thr Thr Pro
1               5                   10                  15

Arg Xaa Xaa

<210> SEQ ID NO 5
<211> LENGTH: 10
<212> TYPE: PRT
<213> ORGANISM: Artificial
<220> FEATURE:
<223> OTHER INFORMATION: Description of sequence: Peptide L-TAT (see
      Table 1)

<400> SEQUENCE: 5

Gly Arg Lys Lys Arg Arg Gln Arg Arg Arg
1               5                   10

<210> SEQ ID NO 6
<211> LENGTH: 10
<212> TYPE: PRT
<213> ORGANISM: Artificial
<220> FEATURE:
<223> OTHER INFORMATION: Description of sequence: Peptide D-TAT (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 6

Arg Arg Arg Gln Arg Arg Lys Lys Arg Gly
1               5                   10

<210> SEQ ID NO 7
<211> LENGTH: 11
<212> TYPE: PRT
<213> ORGANISM: Artificial
<220> FEATURE:
<223> OTHER INFORMATION: Description of sequence: Peptide L-generic-TAT
      (s) (see Table 1)
<220> FEATURE:
<221> NAME/KEY: misc_feature
<223> OTHER INFORMATION: General formula: NH2-Xnb-RKKRRQRRR-Xnb-COOH
      (see Table 1)
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
```

```
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb

<400> SEQUENCE: 7

Xaa Arg Lys Lys Arg Arg Gln Arg Arg Arg Xaa
1               5                   10

<210> SEQ ID NO 8
<211> LENGTH: 11
<212> TYPE: PRT
<213> ORGANISM: Artificial
<220> FEATURE:
<223> OTHER INFORMATION: Description of sequence: Peptide D-generic-TAT
      (s) (see Table 1)
<220> FEATURE:
<221> NAME/KEY: misc_feature
<223> OTHER INFORMATION: General formula: NH2-Xnb-RRRQRRKKR-Xnb-COOH
<220> FEATURE:
<221> NAME/KEY: MUTAGEN
<222> LOCATION: (1)..(10)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb

<400> SEQUENCE: 8

Xaa Arg Arg Arg Gln Arg Arg Lys Lys Arg Xaa
1               5                   10

<210> SEQ ID NO 9
<211> LENGTH: 31
<212> TYPE: PRT
<213> ORGANISM: Artificial
<220> FEATURE:
<223> OTHER INFORMATION: Description of sequence: L-TAT-IB1 (s) (see
      Table 1)

<400> SEQUENCE: 9

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 10
<211> LENGTH: 29
<212> TYPE: PRT
<213> ORGANISM: Artificial
<220> FEATURE:
```

-continued

```
<223> OTHER INFORMATION: Description of sequence: Peptide L-TAT
      (generic) (s) (see Table 1)
<220> FEATURE:
<221> NAME/KEY: misc_feature
<223> OTHER INFORMATION: Description of sequence: General formula:
      NH2-Xnb-RKKRRQRRR-Xnb-Xna-RPTTLXLXXXXXXXQD-Xnb-COOH
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (12)..(12)
<223> OTHER INFORMATION: Xaa is Xna as defined in the general formula,
      wherein Xaa represents an amino acid residue, preferably selected
      from any (native) amino acid residue residue except serine and
      Threonine
<220> FEATURE:
<221> NAME/KEY: REPEAT
<222> LOCATION: (12)..(12)
<223> OTHER INFORMATION: Xaa is Xna as defined in the general formula,
      wherein n is 0 or 1
<220> FEATURE:
<221> NAME/KEY: VARIANT
<222> LOCATION: (18)..(18)
<223> OTHER INFORMATION: Xaa represents an amino acid residue,
      preferably selected from any (native) amino acid residue;
<220> FEATURE:
<221> NAME/KEY: VARIANT
<222> LOCATION: (20)..(26)
<223> OTHER INFORMATION: Xaa represents an amino acid residue,
      preferably selected from any (native) amino acid residue;
<220> FEATURE:
<221> NAME/KEY: VARIANT
<222> LOCATION: (29)..(29)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (29)..(29)
<223> OTHER INFORMATION: Xaa is Xnb as defined in the general formula,
      wherein n is 0-5, 5-10, 10-15, 15-20, 20-30 or more for Xnb

<400> SEQUENCE: 10

Xaa Arg Lys Lys Arg Arg Gln Arg Arg Xaa Xaa Arg Pro Thr Thr
1               5                   10                  15

Leu Xaa Leu Xaa Xaa Xaa Xaa Xaa Xaa Gln Asp Xaa
            20                  25

<210> SEQ ID NO 11
<211> LENGTH: 31
<212> TYPE: PRT
<213> ORGANISM: Artificial
<220> FEATURE:
<223> OTHER INFORMATION: Description of sequence: Peptid D-TAT-IB1 (s)
      (see Table 1)
<220> FEATURE:
```

```
<221> NAME/KEY: MUTAGEN
<222> LOCATION: (1)..(31)
<223> OTHER INFORMATION: all amino acids are D-amino acids

<400> SEQUENCE: 11

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30

<210> SEQ ID NO 12
<211> LENGTH: 29
<212> TYPE: PRT
<213> ORGANISM: Artificial
<220> FEATURE:
<223> OTHER INFORMATION: Description of sequence: Peptid: D-TAT
      (generic) (s) (see Table 1)
<220> FEATURE:
<221> NAME/KEY: misc_feature
<223> OTHER INFORMATION: General formula:
      NH2-Xnb-DQXXXXXXXLXLTTPR-Xna-Xnb-RRRQRRKKR-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (4)..(10)
<223> OTHER INFORMATION: Xaa represents an amino acid residue,
      preferably selected from any (native) amino acid residue;
<220> FEATURE:
<221> NAME/KEY: VARIANT
<222> LOCATION: (12)..(12)
<223> OTHER INFORMATION: Xaa represents an amino acid residue,
      preferably selected from any (native) amino acid residue;
<220> FEATURE:
<221> NAME/KEY: VARIANT
<222> LOCATION: (18)..(18)
<223> OTHER INFORMATION: Xaa is Xna as defined in the general formula,
      wherein Xaa represents an amino acid residue, preferably selected
      from any (native) amino acid residue residue except serine and
      threonine
<220> FEATURE:
<221> NAME/KEY: REPEAT
<222> LOCATION: (18)..(18)
<223> OTHER INFORMATION: Xaa is Xna as defined in the general formula,
      wherein n is 0 or 1
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (29)..(29)
<223> OTHER INFORMATION: Xaa is Xnb as defined in the general formula,
      wherein Xaa represents an amino acid residue, preferably selected
      from any (native) amino acid residue;
<220> FEATURE:
```

```
<221> NAME/KEY: REPEAT
<222> LOCATION: (29)..(29)
<223> OTHER INFORMATION: Xaa is Xnb as defined in the general formula,
      wherein n is 0-5, 5-10, 10-15, 15-20, 20-30 or more for Xnb

<400> SEQUENCE: 12

Xaa Asp Gln Xaa Xaa Xaa Xaa Xaa Xaa Leu Xaa Leu Thr Thr Pro
1               5                   10                  15

Arg Xaa Xaa Arg Arg Arg Gln Arg Arg Lys Lys Arg Xaa
            20                  25

<210> SEQ ID NO 13
<211> LENGTH: 29
<212> TYPE: PRT
<213> ORGANISM: Artificial
<220> FEATURE:
<223> OTHER INFORMATION: Description of sequence: peptide IB1-long (see
      Table 1)

<400> SEQUENCE: 13

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 14
<211> LENGTH: 27
<212> TYPE: PRT
<213> ORGANISM: Artificial
<220> FEATURE:
<223> OTHER INFORMATION: Description of sequence: Peptide IB2-long (see
      Table 1)

<400> SEQUENCE: 14

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 15
<211> LENGTH: 29
<212> TYPE: PRT
<213> ORGANISM: Artificial
<220> FEATURE:
<223> OTHER INFORMATION: Description of sequence: Peptide derived from
      c-Jun (see Table 1)

<400> SEQUENCE: 15

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 16
<211> LENGTH: 29
<212> TYPE: PRT
<213> ORGANISM: Artificial
<220> FEATURE:
<223> OTHER INFORMATION: Description of sequence: Peptide derived from
      ATF2 (see Table 1)

<400> SEQUENCE: 16

Thr Asn Glu Asp His Leu Ala Val His Lys His Lys His Glu Met Thr
1               5                   10                  15

Leu Lys Phe Gly Pro Ala Arg Asn Asp Ser Val Ile Val
```

-continued

```
                    20                  25

<210> SEQ ID NO 17
<211> LENGTH: 23
<212> TYPE: PRT
<213> ORGANISM: Artificial
<220> FEATURE:
<223> OTHER INFORMATION: Description of sequence: Peptide L-IB1 (see
      Table 1)

<400> SEQUENCE: 17

Asp Thr Tyr Arg Pro Lys Arg Pro Thr Thr Leu Asn Leu Phe Pro Gln
1               5                   10                  15

Val Pro Arg Ser Gln Asp Thr
            20

<210> SEQ ID NO 18
<211> LENGTH: 23
<212> TYPE: PRT
<213> ORGANISM: Artificial
<220> FEATURE:
<223> OTHER INFORMATION: Description of sequence: Peptide D-IB1 (see
      Table 1)
<220> FEATURE:
<221> NAME/KEY: MUTAGEN
<222> LOCATION: (1)..(23)
<223> OTHER INFORMATION: all amino acids are D-amino acids

<400> SEQUENCE: 18

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 19
<211> LENGTH: 19
<212> TYPE: PRT
<213> ORGANISM: Artificial
<220> FEATURE:
<223> OTHER INFORMATION: Description of sequence: Peptide L-IB (generic)
      (see Table 1)
<220> FEATURE:
<221> NAME/KEY: VARIANT
<222> LOCATION: (1)..(1)
<223> OTHER INFORMATION: Xaa is selected from any amino acid residue,
<220> FEATURE:
<221> NAME/KEY: VARIANT
<222> LOCATION: (7)..(7)
<223> OTHER INFORMATION: Xaa is selected from any amino acid residue,
<220> FEATURE:
<221> NAME/KEY: VARIANT
<222> LOCATION: (9)..(15)
<223> OTHER INFORMATION: Xaa is selected from any amino acid residue,
<220> FEATURE:
<221> NAME/KEY: VARIANT
<222> LOCATION: (18)..(18)
<223> OTHER INFORMATION: Xaa is selected from serine or threonine,
<220> FEATURE:
<221> NAME/KEY: VARIANT
<222> LOCATION: (19)..(19)
<223> OTHER INFORMATION: Xaa is selected from any amino acid residue,

<400> SEQUENCE: 19

Xaa Arg Pro Thr Thr Leu Xaa Leu Xaa Xaa Xaa Xaa Xaa Xaa Xaa Gln
1               5                   10                  15

Asp Xaa Xaa

<210> SEQ ID NO 20
<211> LENGTH: 19
```

```
<212> TYPE: PRT
<213> ORGANISM: Artificial
<220> FEATURE:
<223> OTHER INFORMATION: Description of sequence: Peptide D-IB (generic)
      (see Table 1)
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (5)..(11)
<223> OTHER INFORMATION: Xaa is selected from any amino acid residue
<220> FEATURE:
<221> NAME/KEY: VARIANT
<222> LOCATION: (13)..(13)
<223> OTHER INFORMATION: Xaa is selected from any amino acid residue
<220> FEATURE:
<221> NAME/KEY: VARIANT
<222> LOCATION: (19)..(19)
<223> OTHER INFORMATION: Xaa is selected from any amino acid residue

<400> SEQUENCE: 20

Xaa Xaa Asp Gln Xaa Xaa Xaa Xaa Xaa Xaa Xaa Leu Xaa Leu Thr Thr
1               5                   10                  15

Pro Arg Xaa

<210> SEQ ID NO 21
<211> LENGTH: 17
<212> TYPE: PRT
<213> ORGANISM: Artificial
<220> FEATURE:
<223> OTHER INFORMATION: Description of sequence: Peptide L-generic-TAT
      (see Table 1)
<220> FEATURE:
<221> NAME/KEY: VARIANT
<222> LOCATION: (1)..(17)
<223> OTHER INFORMATION: Xaa is selected from any amino acid residue

<400> SEQUENCE: 21

Xaa Xaa Xaa Xaa Arg Lys Lys Arg Arg Gln Arg Arg Arg Xaa Xaa Xaa
1               5                   10                  15

Xaa

<210> SEQ ID NO 22
<211> LENGTH: 17
<212> TYPE: PRT
<213> ORGANISM: Artificial
<220> FEATURE:
<223> OTHER INFORMATION: Description of sequence: Peptide D-generic-TAT
      (see Table 1)
<220> FEATURE:
<221> NAME/KEY: MUTAGEN
<222> LOCATION: (1)..(17)
<223> OTHER INFORMATION: all amino acids are D-amino acids
<220> FEATURE:
<221> NAME/KEY: VARIANT
<222> LOCATION: (1)..(17)
<223> OTHER INFORMATION: Xaa is selected from any amino acid residue

<400> SEQUENCE: 22

Xaa Xaa Xaa Xaa Arg Arg Arg Gln Arg Arg Lys Lys Arg Xaa Xaa Xaa
1               5                   10                  15
```

Xaa

<210> SEQ ID NO 23
<211> LENGTH: 35
<212> TYPE: PRT
<213> ORGANISM: Artificial
<220> FEATURE:
<223> OTHER INFORMATION: Description of sequence: Peptide L-TAT-IB1 (see
      Table 1)

<400> SEQUENCE: 23

Gly Arg Lys Lys Arg Arg Gln Arg Arg Pro Pro Asp Thr Tyr Arg
1               5                   10                  15

Pro Lys Arg Pro Thr Thr Leu Asn Leu Phe Pro Gln Val Pro Arg Ser
            20                  25                  30

Gln Asp Thr
        35

<210> SEQ ID NO 24
<211> LENGTH: 42
<212> TYPE: PRT
<213> ORGANISM: Artificial
<220> FEATURE:
<223> OTHER INFORMATION: Description of sequence: Peptide L-TAT IB
      (generic) (see Table 1)
<220> FEATURE:
<221> NAME/KEY: VARIANT
<222> LOCATION: (1)..(40)
<223> OTHER INFORMATION: Xaa is selected from any amino acid residue
<220> FEATURE:
<221> NAME/KEY: VARIANT
<222> LOCATION: (41)..(41)
<223> OTHER INFORMATION: Xaa is selected from serine or threonine
<220> FEATURE:
<221> NAME/KEY: VARIANT
<222> LOCATION: (42)..(42)
<223> OTHER INFORMATION: Xaa is selected from any amino acid residue

<400> SEQUENCE: 24

Xaa Xaa Xaa Xaa Xaa Xaa Xaa Arg Lys Lys Arg Gln Arg Arg
1               5                   10                  15

Xaa Xaa Xaa Xaa Xaa Xaa Xaa Xaa Arg Pro Thr Thr Leu Xaa Leu Xaa
            20                  25                  30

Xaa Xaa Xaa Xaa Xaa Xaa Gln Asp Xaa Xaa
        35                  40

<210> SEQ ID NO 25
<211> LENGTH: 35
<212> TYPE: PRT
<213> ORGANISM: Artificial
<220> FEATURE:
<223> OTHER INFORMATION: Description of sequence: Peptide D-TAT-IB1 (see
      Table 1)
<220> FEATURE:
<221> NAME/KEY: MUTAGEN
<222> LOCATION: (1)..(35)
<223> OTHER INFORMATION: all amino acids are D-amino acids

<400> SEQUENCE: 25

Thr Asp Gln Ser Arg Pro Val Gln Pro Phe Leu Asn Leu Thr Thr Pro
1               5                   10                  15

Arg Lys Pro Arg Tyr Thr Asp Pro Pro Arg Arg Gln Arg Arg Lys
            20                  25                  30

Lys Arg Gly
        35

```
<210> SEQ ID NO 26
<211> LENGTH: 42
<212> TYPE: PRT
<213> ORGANISM: Artificial
<220> FEATURE:
<223> OTHER INFORMATION: Description of sequence: Peptide D-TAT IB
      (generic) (see Table 1)
<220> FEATURE:
<221> NAME/KEY: MUTAGEN
<222> LOCATION: (1)..(42)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (3)..(42)
<223> OTHER INFORMATION: Xaa is selected from any amino acid residue

<400> SEQUENCE: 26

Xaa Xaa Asp Gln Xaa Xaa Xaa Xaa Xaa Xaa Xaa Leu Xaa Leu Thr Thr
1               5                   10                  15

Pro Arg Xaa Xaa Xaa Xaa Xaa Xaa Xaa Arg Arg Arg Gln Arg Arg
            20                  25                  30

Lys Lys Arg Xaa Xaa Xaa Xaa Xaa Xaa Xaa
        35                  40

<210> SEQ ID NO 27
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s1) (see Table 1)

<400> SEQUENCE: 27

Arg Lys Lys Arg Arg Gln Arg Arg Arg Pro Pro Arg Pro Lys Arg Pro
1               5                   10                  15

Thr Thr Leu Asn Leu Phe Pro Gln Val Pro Arg Ser Gln Asp
            20                  25                  30

<210> SEQ ID NO 28
<211> LENGTH: 30
<212> TYPE: PRT
<213> ORGANISM: Artificial
<220> FEATURE:
<223> OTHER INFORMATION: Description of sequence: chimeric peptide
      sequence L-TAT-IB1(s2) (see Table 1)
<220> FEATURE:
<221> NAME/KEY: VARIANT
<222> LOCATION: (11)..(11)
<223> OTHER INFORMATION: Xaa is selected from glycine or proline
<220> FEATURE:
<221> NAME/KEY: REPEAT
<222> LOCATION: (11)..(11)
<223> OTHER INFORMATION: Xaa is Xnc as defined in the general formula,
      wherein n is 0-5, 5-10, 10-15, 15-20, 20-30 or more for Xnc

<400> SEQUENCE: 28

Gly Arg Lys Lys Arg Arg Gln Arg Arg Arg Xaa Arg Pro Lys Arg Pro
1               5                   10                  15

Thr Thr Leu Asn Leu Phe Pro Gln Val Pro Arg Ser Gln Asp
            20                  25                  30
```

-continued

```
<210> SEQ ID NO 29
<211> LENGTH: 29
<212> TYPE: PRT
<213> ORGANISM: Artificial
<220> FEATURE:
<223> OTHER INFORMATION: Description of sequence: chimeric peptide
      sequence L-TAT-IB1(s3) (see Table 1)
<220> FEATURE:
<221> NAME/KEY: VARIANT
<222> LOCATION: (10)..(10)
<223> OTHER INFORMATION: Xaa is selected from glycine or proline
<220> FEATURE:
<221> NAME/KEY: REPEAT
<222> LOCATION: (10)..(10)
<223> OTHER INFORMATION: Xaa is Xnc as defined in the general formula,
      wherein n is 0-5, 5-10, 10-15, 15-20, 20-30 or more for Xnc

<400> SEQUENCE: 29

Arg Lys Lys Arg Arg Gln Arg Arg Xaa Arg Pro Lys Arg Pro Thr
1               5                   10                  15

Thr Leu Asn Leu Phe Pro Gln Val Pro Arg Ser Gln Asp
            20                  25

<210> SEQ ID NO 30
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s1) (see Table 1)
<220> FEATURE:
<221> NAME/KEY: MUTAGEN
<222> LOCATION: (1)..(30)
<223> OTHER INFORMATION: all amino acids are D-amino acids

<400> SEQUENCE: 30

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg
            20                  25                  30

<210> SEQ ID NO 31
<211> LENGTH: 30
<212> TYPE: PRT
<213> ORGANISM: Artificial
<220> FEATURE:
<223> OTHER INFORMATION: Description of sequence: chimeric peptide
      sequence D-TAT-IB1(s2) (see Table 1)
<220> FEATURE:
<221> NAME/KEY: MUTAGEN
<222> LOCATION: (1)..(30)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
<223> OTHER INFORMATION: Xaa is Xnc as defined in the general formula,
      wherein n is 0-5, 5-10, 10-15, 15-20, 20-30 or more for Xnc

<400> SEQUENCE: 31

Asp Gln Ser Arg Pro Val Gln Pro Phe Leu Asn Leu Thr Thr Pro Arg
1               5                   10                  15

Lys Pro Arg Xaa Arg Arg Arg Gln Arg Arg Lys Lys Arg Gly
            20                  25                  30

<210> SEQ ID NO 32
<211> LENGTH: 29
```

```
<212> TYPE: PRT
<213> ORGANISM: Artificial
<220> FEATURE:
<223> OTHER INFORMATION: Description of sequence: chimeric peptide
      sequence D-TAT-IB1(s3) (see Table 1)
<220> FEATURE:
<221> NAME/KEY: MUTAGEN
<222> LOCATION: (1)..(29)
<223> OTHER INFORMATION: all amino acids are D-amino acids
<220> FEATURE:
<221> NAME/KEY: VARIANT
<222> LOCATION: (20)..(20)
<223> OTHER INFORMATION: Xaa is selected from glycine or proline
<220> FEATURE:
<221> NAME/KEY: REPEAT
<222> LOCATION: (20)..(20)
<223> OTHER INFORMATION: Xaa is Xnc as defined in the general formula,
      wherein n is 0-5, 5-10, 10-15, 15-20, 20-30 or more for Xnc

<400> SEQUENCE: 32

Asp Gln Ser Arg Pro Val Gln Pro Phe Leu Asn Leu Thr Thr Pro Arg
1               5                   10                  15

Lys Pro Arg Xaa Arg Arg Gln Arg Arg Lys Lys Arg
            20                  25

<210> SEQ ID NO 33
<211> LENGTH: 13
<212> TYPE: PRT
<213> ORGANISM: Artificial
<220> FEATURE:
<223> OTHER INFORMATION: Description of sequence: L-IB1(s1) (see
      Table 1)

<400> SEQUENCE: 33

Thr Leu Asn Leu Phe Pro Gln Val Pro Arg Ser Gln Asp
1               5                   10

<210> SEQ ID NO 34
<211> LENGTH: 13
<212> TYPE: PRT
<213> ORGANISM: Artificial
<220> FEATURE:
<223> OTHER INFORMATION: Description of sequence: L-IB1(s2) (see
      Table 1)

<400> SEQUENCE: 34

Thr Thr Leu Asn Leu Phe Pro Gln Val Pro Arg Ser Gln
1               5                   10

<210> SEQ ID NO 35
<211> LENGTH: 13
<212> TYPE: PRT
<213> ORGANISM: Artificial
<220> FEATURE:
<223> OTHER INFORMATION: Description of sequence: L-IB1(s3) (see
      Table 1)

<400> SEQUENCE: 35

Pro Thr Thr Leu Asn Leu Phe Pro Gln Val Pro Arg Ser
1               5                   10

<210> SEQ ID NO 36
<211> LENGTH: 13
<212> TYPE: PRT
<213> ORGANISM: Artificial
<220> FEATURE:
<223> OTHER INFORMATION: Description of sequence: L-IB1(s4) (see
      Table 1)

<400> SEQUENCE: 36
```

```
Arg Pro Thr Thr Leu Asn Leu Phe Pro Gln Val Pro Arg
1               5                   10

<210> SEQ ID NO 37
<211> LENGTH: 13
<212> TYPE: PRT
<213> ORGANISM: Artificial
<220> FEATURE:
<223> OTHER INFORMATION: Description of sequence: L-IB1(s5) (see
      Table 1)

<400> SEQUENCE: 37

Lys Arg Pro Thr Thr Leu Asn Leu Phe Pro Gln Val Pro
1               5                   10

<210> SEQ ID NO 38
<211> LENGTH: 13
<212> TYPE: PRT
<213> ORGANISM: Artificial
<220> FEATURE:
<223> OTHER INFORMATION: Description of sequence: L-IB1(s6) (see
      Table 1)

<400> SEQUENCE: 38

Pro Lys Arg Pro Thr Thr Leu Asn Leu Phe Pro Gln Val
1               5                   10

<210> SEQ ID NO 39
<211> LENGTH: 13
<212> TYPE: PRT
<213> ORGANISM: Artificial
<220> FEATURE:
<223> OTHER INFORMATION: Description of sequence: L-IB1(s7) (see
      Table 1)

<400> SEQUENCE: 39

Arg Pro Lys Arg Pro Thr Thr Leu Asn Leu Phe Pro Gln
1               5                   10

<210> SEQ ID NO 40
<211> LENGTH: 12
<212> TYPE: PRT
<213> ORGANISM: Artificial
<220> FEATURE:
<223> OTHER INFORMATION: Description of sequence: L-IB1(s8) (see
      Table 1)

<400> SEQUENCE: 40

Leu Asn Leu Phe Pro Gln Val Pro Arg Ser Gln Asp
1               5                   10

<210> SEQ ID NO 41
<211> LENGTH: 12
<212> TYPE: PRT
<213> ORGANISM: Artificial
<220> FEATURE:
<223> OTHER INFORMATION: Description of sequence: L-IB1(s9) (see
      Table 1)

<400> SEQUENCE: 41

Thr Leu Asn Leu Phe Pro Gln Val Pro Arg Ser Gln
1               5                   10

<210> SEQ ID NO 42
<211> LENGTH: 12
<212> TYPE: PRT
<213> ORGANISM: Artificial
```

```
<220> FEATURE:
<223> OTHER INFORMATION: Description of sequence: L-IB1(s10) (see
      Table 1)

<400> SEQUENCE: 42

Thr Thr Leu Asn Leu Phe Pro Gln Val Pro Arg Ser
1               5                   10

<210> SEQ ID NO 43
<211> LENGTH: 12
<212> TYPE: PRT
<213> ORGANISM: Artificial
<220> FEATURE:
<223> OTHER INFORMATION: Description of sequence: L-IB1(s11) (see
      Table 1)

<400> SEQUENCE: 43

Pro Thr Thr Leu Asn Leu Phe Pro Gln Val Pro Arg
1               5                   10

<210> SEQ ID NO 44
<211> LENGTH: 12
<212> TYPE: PRT
<213> ORGANISM: Artificial
<220> FEATURE:
<223> OTHER INFORMATION: Description of sequence: L-IB1(s12) (see
      Table 1)

<400> SEQUENCE: 44

Arg Pro Thr Thr Leu Asn Leu Phe Pro Gln Val Pro
1               5                   10

<210> SEQ ID NO 45
<211> LENGTH: 12
<212> TYPE: PRT
<213> ORGANISM: Artificial
<220> FEATURE:
<223> OTHER INFORMATION: Description of sequence: L-IB1(s13) (see
      Table 1)

<400> SEQUENCE: 45

Lys Arg Pro Thr Thr Leu Asn Leu Phe Pro Gln Val
1               5                   10

<210> SEQ ID NO 46
<211> LENGTH: 12
<212> TYPE: PRT
<213> ORGANISM: Artificial
<220> FEATURE:
<223> OTHER INFORMATION: Description of sequence: L-IB1(s14) (see
      Table 1)

<400> SEQUENCE: 46

Pro Lys Arg Pro Thr Thr Leu Asn Leu Phe Pro Gln
1               5                   10

<210> SEQ ID NO 47
<211> LENGTH: 12
<212> TYPE: PRT
<213> ORGANISM: Artificial
<220> FEATURE:
<223> OTHER INFORMATION: Description of sequence: L-IB1(s15) (see
      Table 1)

<400> SEQUENCE: 47

Arg Pro Lys Arg Pro Thr Thr Leu Asn Leu Phe Pro
1               5                   10
```

<210> SEQ ID NO 48
<211> LENGTH: 11
<212> TYPE: PRT
<213> ORGANISM: Artificial
<220> FEATURE:
<223> OTHER INFORMATION: Description of sequence: L-IB1(s16) (see
      Table 1)

<400> SEQUENCE: 48

Asn Leu Phe Pro Gln Val Pro Arg Ser Gln Asp
1               5                   10

<210> SEQ ID NO 49
<211> LENGTH: 11
<212> TYPE: PRT
<213> ORGANISM: Artificial
<220> FEATURE:
<223> OTHER INFORMATION: Description of sequence: L-IB1(s17) (see
      Table 1)

<400> SEQUENCE: 49

Leu Asn Leu Phe Pro Gln Val Pro Arg Ser Gln
1               5                   10

<210> SEQ ID NO 50
<211> LENGTH: 11
<212> TYPE: PRT
<213> ORGANISM: Artificial
<220> FEATURE:
<223> OTHER INFORMATION: Description of sequence: L-IB1(s18) (see
      Table 1)

<400> SEQUENCE: 50

Thr Leu Asn Leu Phe Pro Gln Val Pro Arg Ser
1               5                   10

<210> SEQ ID NO 51
<211> LENGTH: 11
<212> TYPE: PRT
<213> ORGANISM: Artificial
<220> FEATURE:
<223> OTHER INFORMATION: Description of sequence: L-IB1(s19) (see
      Table 1)

<400> SEQUENCE: 51

Thr Thr Leu Asn Leu Phe Pro Gln Val Pro Arg
1               5                   10

<210> SEQ ID NO 52
<211> LENGTH: 11
<212> TYPE: PRT
<213> ORGANISM: Artificial
<220> FEATURE:
<223> OTHER INFORMATION: Description of sequence: L-IB1(s20) (see
      Table 1)

<400> SEQUENCE: 52

Pro Thr Thr Leu Asn Leu Phe Pro Gln Val Pro
1               5                   10

<210> SEQ ID NO 53
<211> LENGTH: 11
<212> TYPE: PRT
<213> ORGANISM: Artificial
<220> FEATURE:
<223> OTHER INFORMATION: Description of sequence: L-IB1(s21) (see
      Table 1)

```
<400> SEQUENCE: 53

Arg Pro Thr Thr Leu Asn Leu Phe Pro Gln Val
1               5                   10

<210> SEQ ID NO 54
<211> LENGTH: 11
<212> TYPE: PRT
<213> ORGANISM: Artificial
<220> FEATURE:
<223> OTHER INFORMATION: Description of sequence: L-IB1(s22) (see
      Table 1)

<400> SEQUENCE: 54

Lys Arg Pro Thr Thr Leu Asn Leu Phe Pro Gln
1               5                   10

<210> SEQ ID NO 55
<211> LENGTH: 11
<212> TYPE: PRT
<213> ORGANISM: Artificial
<220> FEATURE:
<223> OTHER INFORMATION: Description of sequence: L-IB1(s23) (see
      Table 1)

<400> SEQUENCE: 55

Pro Lys Arg Pro Thr Thr Leu Asn Leu Phe Pro
1               5                   10

<210> SEQ ID NO 56
<211> LENGTH: 11
<212> TYPE: PRT
<213> ORGANISM: Artificial
<220> FEATURE:
<223> OTHER INFORMATION: Description of sequence: L-IB1(s24) (see
      Table 1)

<400> SEQUENCE: 56

Arg Pro Lys Arg Pro Thr Thr Leu Asn Leu Phe
1               5                   10

<210> SEQ ID NO 57
<211> LENGTH: 10
<212> TYPE: PRT
<213> ORGANISM: Artificial
<220> FEATURE:
<223> OTHER INFORMATION: Description of sequence: L-IB1(s25) (see
      Table 1)

<400> SEQUENCE: 57

Leu Phe Pro Gln Val Pro Arg Ser Gln Asp
1               5                   10

<210> SEQ ID NO 58
<211> LENGTH: 10
<212> TYPE: PRT
<213> ORGANISM: Artificial
<220> FEATURE:
<223> OTHER INFORMATION: Description of sequence: L-IB1(s26) (see
      Table 1)

<400> SEQUENCE: 58

Asn Leu Phe Pro Gln Val Pro Arg Ser Gln
1               5                   10

<210> SEQ ID NO 59
<211> LENGTH: 10
<212> TYPE: PRT
```

```
<213> ORGANISM: Artificial
<220> FEATURE:
<223> OTHER INFORMATION: Description of sequence: L-IB1(s27) (see
      Table 1)

<400> SEQUENCE: 59

Leu Asn Leu Phe Pro Gln Val Pro Arg Ser
1               5                   10

<210> SEQ ID NO 60
<211> LENGTH: 10
<212> TYPE: PRT
<213> ORGANISM: Artificial
<220> FEATURE:
<223> OTHER INFORMATION: Description of sequence: L-IB1(s28) (see
      Table 1)

<400> SEQUENCE: 60

Thr Leu Asn Leu Phe Pro Gln Val Pro Arg
1               5                   10

<210> SEQ ID NO 61
<211> LENGTH: 10
<212> TYPE: PRT
<213> ORGANISM: Artificial
<220> FEATURE:
<223> OTHER INFORMATION: Description of sequence: L-IB1(s29) (see
      Table 1)

<400> SEQUENCE: 61

Thr Thr Leu Asn Leu Phe Pro Gln Val Pro
1               5                   10

<210> SEQ ID NO 62
<211> LENGTH: 10
<212> TYPE: PRT
<213> ORGANISM: Artificial
<220> FEATURE:
<223> OTHER INFORMATION: Description of sequence: L-IB1(s30) (see
      Table 1)

<400> SEQUENCE: 62

Pro Thr Thr Leu Asn Leu Phe Pro Gln Val
1               5                   10

<210> SEQ ID NO 63
<211> LENGTH: 10
<212> TYPE: PRT
<213> ORGANISM: Artificial
<220> FEATURE:
<223> OTHER INFORMATION: Description of sequence: L-IB1(s31) (see
      Table 1)

<400> SEQUENCE: 63

Arg Pro Thr Thr Leu Asn Leu Phe Pro Gln
1               5                   10

<210> SEQ ID NO 64
<211> LENGTH: 10
<212> TYPE: PRT
<213> ORGANISM: Artificial
<220> FEATURE:
<223> OTHER INFORMATION: Description of sequence: L-IB1(s32) (see
      Table 1)

<400> SEQUENCE: 64

Lys Arg Pro Thr Thr Leu Asn Leu Phe Pro
1               5                   10
```

```
<210> SEQ ID NO 65
<211> LENGTH: 10
<212> TYPE: PRT
<213> ORGANISM: Artificial
<220> FEATURE:
<223> OTHER INFORMATION: Description of sequence: L-IB1(s33) (see
      Table 1)

<400> SEQUENCE: 65

Pro Lys Arg Pro Thr Thr Leu Asn Leu Phe
1               5                   10

<210> SEQ ID NO 66
<211> LENGTH: 10
<212> TYPE: PRT
<213> ORGANISM: Artificial
<220> FEATURE:
<223> OTHER INFORMATION: Description of sequence: L-IB1(s34) (see
      Table 1)

<400> SEQUENCE: 66

Arg Pro Lys Arg Pro Thr Thr Leu Asn Leu
1               5                   10

<210> SEQ ID NO 67
<211> LENGTH: 13
<212> TYPE: PRT
<213> ORGANISM: Artificial
<220> FEATURE:
<223> OTHER INFORMATION: Description of sequence: D-IB1(s1) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 67

Gln Pro Phe Leu Asn Leu Thr Thr Pro Arg Lys Pro Arg
1               5                   10

<210> SEQ ID NO 68
<211> LENGTH: 13
<212> TYPE: PRT
<213> ORGANISM: Artificial
<220> FEATURE:
<223> OTHER INFORMATION: Description of sequence: D-IB1(s2) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 68

Val Gln Pro Phe Leu Asn Leu Thr Thr Pro Arg Lys Pro
1               5                   10

<210> SEQ ID NO 69
<211> LENGTH: 13
<212> TYPE: PRT
<213> ORGANISM: Artificial
<220> FEATURE:
<223> OTHER INFORMATION: Description of sequence: D-IB1(s3) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 69
```

Pro Val Gln Pro Phe Leu Asn Leu Thr Thr Pro Arg Lys
1               5                   10

<210> SEQ ID NO 70
<211> LENGTH: 13
<212> TYPE: PRT
<213> ORGANISM: Artificial
<220> FEATURE:
<223> OTHER INFORMATION: Description of sequence: D-IB1(s4) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 70

Arg Pro Val Gln Pro Phe Leu Asn Leu Thr Thr Pro Arg
1               5                   10

<210> SEQ ID NO 71
<211> LENGTH: 13
<212> TYPE: PRT
<213> ORGANISM: Artificial
<220> FEATURE:
<223> OTHER INFORMATION: Description of sequence: D-IB1(s5) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 71

Ser Arg Pro Val Gln Pro Phe Leu Asn Leu Thr Thr Pro
1               5                   10

<210> SEQ ID NO 72
<211> LENGTH: 13
<212> TYPE: PRT
<213> ORGANISM: Artificial
<220> FEATURE:
<223> OTHER INFORMATION: Description of sequence: D-IB1(s6) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 72

Gln Ser Arg Pro Val Gln Pro Phe Leu Asn Leu Thr Thr
1               5                   10

<210> SEQ ID NO 73
<211> LENGTH: 13
<212> TYPE: PRT
<213> ORGANISM: Artificial
<220> FEATURE:
<223> OTHER INFORMATION: Description of sequence: D-IB1(s7) (see
      Table 1)
<220> FEATURE:
<221> NAME/KEY: MUTAGEN
<222> LOCATION: (1)..(13)
<223> OTHER INFORMATION: all amino acids are D-amino acids

<400> SEQUENCE: 73

Asp Gln Ser Arg Pro Val Gln Pro Phe Leu Asn Leu Thr
1               5                   10

<210> SEQ ID NO 74
<211> LENGTH: 12

```
<212> TYPE: PRT
<213> ORGANISM: Artificial
<220> FEATURE:
<223> OTHER INFORMATION: Description of sequence: D-IB1(s8) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 74

Pro Phe Leu Asn Leu Thr Thr Pro Arg Lys Pro Arg
1               5                   10

<210> SEQ ID NO 75
<211> LENGTH: 12
<212> TYPE: PRT
<213> ORGANISM: Artificial
<220> FEATURE:
<223> OTHER INFORMATION: Description of sequence: D-IB1(s9) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 75

Gln Pro Phe Leu Asn Leu Thr Thr Pro Arg Lys Pro
1               5                   10

<210> SEQ ID NO 76
<211> LENGTH: 12
<212> TYPE: PRT
<213> ORGANISM: Artificial
<220> FEATURE:
<223> OTHER INFORMATION: Description of sequence: D-IB1(s10) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 76

Val Gln Pro Phe Leu Asn Leu Thr Thr Pro Arg Lys
1               5                   10

<210> SEQ ID NO 77
<211> LENGTH: 12
<212> TYPE: PRT
<213> ORGANISM: Artificial
<220> FEATURE:
<223> OTHER INFORMATION: Description of sequence: D-IB1(s11) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 77

Pro Val Gln Pro Phe Leu Asn Leu Thr Thr Pro Arg
1               5                   10

<210> SEQ ID NO 78
<211> LENGTH: 12
<212> TYPE: PRT
<213> ORGANISM: Artificial
<220> FEATURE:
<223> OTHER INFORMATION: Description of sequence: D-IB1(s12) (see
      Table 1)
<220> FEATURE:
<221> NAME/KEY: MUTAGEN
```

```
<222> LOCATION: (1)..(12)
<223> OTHER INFORMATION: all amino acids are D-amino acids

<400> SEQUENCE: 78

Arg Pro Val Gln Pro Phe Leu Asn Leu Thr Thr Pro
1               5                   10

<210> SEQ ID NO 79
<211> LENGTH: 12
<212> TYPE: PRT
<213> ORGANISM: Artificial
<220> FEATURE:
<223> OTHER INFORMATION: Description of sequence: D-IB1(s13) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 79

Ser Arg Pro Val Gln Pro Phe Leu Asn Leu Thr Thr
1               5                   10

<210> SEQ ID NO 80
<211> LENGTH: 12
<212> TYPE: PRT
<213> ORGANISM: Artificial
<220> FEATURE:
<223> OTHER INFORMATION: Description of sequence: D-IB1(s14) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 80

Gln Ser Arg Pro Val Gln Pro Phe Leu Asn Leu Thr
1               5                   10

<210> SEQ ID NO 81
<211> LENGTH: 12
<212> TYPE: PRT
<213> ORGANISM: Artificial
<220> FEATURE:
<223> OTHER INFORMATION: Description of sequence: D-IB1(s15) (see
      Table 1)
<220> FEATURE:
<221> NAME/KEY: MUTAGEN
<222> LOCATION: (1)..(12)
<223> OTHER INFORMATION: all amino acids are D-amino acids

<400> SEQUENCE: 81

Asp Gln Ser Arg Pro Val Gln Pro Phe Leu Asn Leu
1               5                   10

<210> SEQ ID NO 82
<211> LENGTH: 11
<212> TYPE: PRT
<213> ORGANISM: Artificial
<220> FEATURE:
<223> OTHER INFORMATION: Description of sequence: D-IB1(s16) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 82

Phe Leu Asn Leu Thr Thr Pro Arg Lys Pro Arg
1               5                   10
```

```
<210> SEQ ID NO 83
<211> LENGTH: 11
<212> TYPE: PRT
<213> ORGANISM: Artificial
<220> FEATURE:
<223> OTHER INFORMATION: Description of sequence: D-IB1(s17) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 83

Pro Phe Leu Asn Leu Thr Thr Pro Arg Lys Pro
1               5                   10

<210> SEQ ID NO 84
<211> LENGTH: 11
<212> TYPE: PRT
<213> ORGANISM: Artificial
<220> FEATURE:
<223> OTHER INFORMATION: Description of sequence: D-IB1(s18) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 84

Gln Pro Phe Leu Asn Leu Thr Thr Pro Arg Lys
1               5                   10

<210> SEQ ID NO 85
<211> LENGTH: 11
<212> TYPE: PRT
<213> ORGANISM: Artificial
<220> FEATURE:
<223> OTHER INFORMATION: Description of sequence: D-IB1(s19) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 85

Val Gln Pro Phe Leu Asn Leu Thr Thr Pro Arg
1               5                   10

<210> SEQ ID NO 86
<211> LENGTH: 11
<212> TYPE: PRT
<213> ORGANISM: Artificial
<220> FEATURE:
<223> OTHER INFORMATION: Description of sequence: D-IB1(s20) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 86

Pro Val Gln Pro Phe Leu Asn Leu Thr Thr Pro
1               5                   10

<210> SEQ ID NO 87
<211> LENGTH: 11
<212> TYPE: PRT
<213> ORGANISM: Artificial
<220> FEATURE:
```

```
<223> OTHER INFORMATION: Description of sequence: D-IB1(s21) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 87

Arg Pro Val Gln Pro Phe Leu Asn Leu Thr Thr
1               5                   10

<210> SEQ ID NO 88
<211> LENGTH: 11
<212> TYPE: PRT
<213> ORGANISM: Artificial
<220> FEATURE:
<223> OTHER INFORMATION: Description of sequence: D-IB1(s22) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 88

Ser Arg Pro Val Gln Pro Phe Leu Asn Leu Thr
1               5                   10

<210> SEQ ID NO 89
<211> LENGTH: 11
<212> TYPE: PRT
<213> ORGANISM: Artificial
<220> FEATURE:
<223> OTHER INFORMATION: Description of sequence: D-IB1(s23) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 89

Gln Ser Arg Pro Val Gln Pro Phe Leu Asn Leu
1               5                   10

<210> SEQ ID NO 90
<211> LENGTH: 11
<212> TYPE: PRT
<213> ORGANISM: Artificial
<220> FEATURE:
<223> OTHER INFORMATION: Description of sequence: D-IB1(s24) (see
      Table 1)
<220> FEATURE:
<221> NAME/KEY: MUTAGEN
<222> LOCATION: (1)..(11)
<223> OTHER INFORMATION: all amino acids are D-amino acids

<400> SEQUENCE: 90

Asp Gln Ser Arg Pro Val Gln Pro Phe Leu Asn
1               5                   10

<210> SEQ ID NO 91
<211> LENGTH: 10
<212> TYPE: PRT
<213> ORGANISM: Artificial
<220> FEATURE:
<223> OTHER INFORMATION: Description of sequence: D-IB1(s25) (see
      Table 1)
<220> FEATURE:
<221> NAME/KEY: MUTAGEN
<222> LOCATION: (1)..(10)
<223> OTHER INFORMATION: all amino acids are D-amino acids
```

-continued

<400> SEQUENCE: 91

Asp Gln Ser Arg Pro Val Gln Pro Phe Leu
1               5                   10

<210> SEQ ID NO 92
<211> LENGTH: 10
<212> TYPE: PRT
<213> ORGANISM: Artificial
<220> FEATURE:
<223> OTHER INFORMATION: Description of sequence: D-IB1(s26) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 92

Gln Ser Arg Pro Val Gln Pro Phe Leu Asn
1               5                   10

<210> SEQ ID NO 93
<211> LENGTH: 10
<212> TYPE: PRT
<213> ORGANISM: Artificial
<220> FEATURE:
<223> OTHER INFORMATION: Description of sequence: D-IB1(s27) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 93

Ser Arg Pro Val Gln Pro Phe Leu Asn Leu
1               5                   10

<210> SEQ ID NO 94
<211> LENGTH: 10
<212> TYPE: PRT
<213> ORGANISM: Artificial
<220> FEATURE:
<223> OTHER INFORMATION: Description of sequence: D-IB1(s28) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 94

Arg Pro Val Gln Pro Phe Leu Asn Leu Thr
1               5                   10

<210> SEQ ID NO 95
<211> LENGTH: 10
<212> TYPE: PRT
<213> ORGANISM: Artificial
<220> FEATURE:
<223> OTHER INFORMATION: Description of sequence: D-IB1(s29) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 95

Pro Val Gln Pro Phe Leu Asn Leu Thr Thr
1               5                   10

<210> SEQ ID NO 96

```
<211> LENGTH: 10
<212> TYPE: PRT
<213> ORGANISM: Artificial
<220> FEATURE:
<223> OTHER INFORMATION: Description of sequence: D-IB1(s30) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 96

Val Gln Pro Phe Leu Asn Leu Thr Thr Pro
1               5                   10

<210> SEQ ID NO 97
<211> LENGTH: 10
<212> TYPE: PRT
<213> ORGANISM: Artificial
<220> FEATURE:
<223> OTHER INFORMATION: Description of sequence: D-IB1(s31) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 97

Gln Pro Phe Leu Asn Leu Thr Thr Pro Arg
1               5                   10

<210> SEQ ID NO 98
<211> LENGTH: 10
<212> TYPE: PRT
<213> ORGANISM: Artificial
<220> FEATURE:
<223> OTHER INFORMATION: Description of sequence: D-IB1(s32) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 98

Pro Phe Leu Asn Leu Thr Thr Pro Arg Lys
1               5                   10

<210> SEQ ID NO 99
<211> LENGTH: 10
<212> TYPE: PRT
<213> ORGANISM: Artificial
<220> FEATURE:
<223> OTHER INFORMATION: Description of sequence: D-IB1(s33) (see
      Table 1)
<220> FEATURE:
<221> NAME/KEY: MUTAGEN
<222> LOCATION: (1)..(10)
<223> OTHER INFORMATION: all amino acids are D-amino acids

<400> SEQUENCE: 99

Phe Leu Asn Leu Thr Thr Pro Arg Lys Pro
1               5                   10

<210> SEQ ID NO 100
<211> LENGTH: 10
<212> TYPE: PRT
<213> ORGANISM: Artificial
<220> FEATURE:
<223> OTHER INFORMATION: Description of sequence: D-IB1(s34) (see
      Table 1)
<220> FEATURE:
```

```
<221> NAME/KEY: MUTAGEN
<222> LOCATION: (1)..(10)
<223> OTHER INFORMATION: all amino acids are D-amino acids

<400> SEQUENCE: 100

Leu Asn Leu Thr Thr Pro Arg Lys Pro Arg
1               5                   10

<210> SEQ ID NO 101
<211> LENGTH: 21
<212> TYPE: DNA
<213> ORGANISM: Artificial
<220> FEATURE:
<223> OTHER INFORMATION: Description of sequence: ap-1 doubled labeled
      probe (see p. 60)

<400> SEQUENCE: 101
cgcttgatga gtcagccgga a                                            21

<210> SEQ ID NO 102
<211> LENGTH: 2953
<212> TYPE: DNA
<213> ORGANISM: Artificial
<220> FEATURE:
<223> OTHER INFORMATION: description of sequence: rat IB1 cDNA sequence
      and its predicted amino acid sequence (see Figure 1)
<220> FEATURE:
<221> NAME/KEY: CDS
<222> LOCATION: (108)..(2252)

<400> SEQUENCE: 102
ccgccccagc tcagtccgaa ccccgcggcg gcggcggcct cctccacacg cctccacctc    60
cgccgccgcc gccgccgccg ccgcctcccg cgccgctctc cgcccgg atg gcc agg     116
                                                    Met Ala Arg
                                                    1 ctg agc ccg gga atg gcg gag cga gag agc ggc ctg agc ggg ggt gcc    164
Leu Ser Pro Gly Met Ala Glu Arg Glu Ser Gly Leu Ser Gly Gly Ala
     5              10                  15 gcg tcc cca ccg gcc gct tcc cca ttc ctg gga ctg cac atc gcg tcg    212
Ala Ser Pro Pro Ala Ala Ser Pro Phe Leu Gly Leu His Ile Ala Ser
20                  25                  30                  35 cct ccc aat ttc agg ctc acc cat gat atc agc ctg gag gag ttt gag    260
Pro Pro Asn Phe Arg Leu Thr His Asp Ile Ser Leu Glu Glu Phe Glu
                40                  45                  50 gat gaa gac ctt tcg gag atc act gat gag tgt ggc atc agc ctg cag    308
Asp Glu Asp Leu Ser Glu Ile Thr Asp Glu Cys Gly Ile Ser Leu Gln
            55                  60                  65 tgc aaa gac acc ttg tct ctc cgg ccc cgc gcc ggg cta ctg tct        356
Cys Lys Asp Thr Leu Ser Leu Arg Pro Arg Ala Gly Leu Leu Ser
        70                  75                  80 gcg ggt agc agc ggt agc gcg ggg agc cgg ctg cag gcg gag atg ctg    404
Ala Gly Ser Ser Gly Ser Ala Gly Ser Arg Leu Gln Ala Glu Met Leu
    85                  90                  95 cag atg gac ctg atc gac gcg gca agt gac act ccg ggc gcc gag gac    452
Gln Met Asp Leu Ile Asp Ala Ala Ser Asp Thr Pro Gly Ala Glu Asp
100                 105                 110                 115 gac gaa gag gac gac gac gag ctc gct gcc caa cgg cca gga gtg ggg    500
Asp Glu Glu Asp Asp Asp Glu Leu Ala Ala Gln Arg Pro Gly Val Gly
                120                 125                 130 cct tcc aaa gcc gag tct ggc cag gag ccg gcg tct cgc agc cag ggt    548
Pro Ser Lys Ala Glu Ser Gly Gln Glu Pro Ala Ser Arg Ser Gln Gly
            135                 140                 145 cag ggc cag ggc ccc ggc aca ggc tgc gga gac acc tac cgg ccc aag    596
```

```
                Gln Gly Gln Gly Pro Gly Thr Gly Cys Gly Asp Thr Tyr Arg Pro Lys
                        150                 155                 160 agg cct acc acg ctc aac ctt ttc ccg cag gtg ccg cgg tct cag gac          644
Arg Pro Thr Thr Leu Asn Leu Phe Pro Gln Val Pro Arg Ser Gln Asp
165                 170                 175 acg ctg aat aat aac tct tta ggc aaa aag cac agt tgg cag gac cgt          692
Thr Leu Asn Asn Asn Ser Leu Gly Lys Lys His Ser Trp Gln Asp Arg
180                 185                 190                 195 gtg tct cga tca tcc tcc cct ctg aag aca ggg gag cag acg cct cca          740
Val Ser Arg Ser Ser Ser Pro Leu Lys Thr Gly Glu Gln Thr Pro Pro
            200                 205                 210 cat gaa cat atc tgc ctg agt gat gag ctg ccg ccc cag ggc agt cct          788
His Glu His Ile Cys Leu Ser Asp Glu Leu Pro Pro Gln Gly Ser Pro
            215                 220                 225 gtt ccc acc cag gat cgt ggc act tcc acc gac agc cct tgt cgc cgt          836
Val Pro Thr Gln Asp Arg Gly Thr Ser Thr Asp Ser Pro Cys Arg Arg
            230                 235                 240 act gca gcc acc cag atg gca cct cca agt ggt ccc cct gcc act gca          884
Thr Ala Ala Thr Gln Met Ala Pro Pro Ser Gly Pro Pro Ala Thr Ala
245                 250                 255 cct ggt ggc cgg ggc cac tcc cat cga gat cgg tcc ata tca gca gat          932
Pro Gly Gly Arg Gly His Ser His Arg Asp Arg Ser Ile Ser Ala Asp
260                 265                 270                 275 gtg cgg ctc gag gcg act gag gag atc tac ctg acc cca gtg cag agg          980
Val Arg Leu Glu Ala Thr Glu Glu Ile Tyr Leu Thr Pro Val Gln Arg
            280                 285                 290 ccc cca gac cct gca gaa ccc acc tcc acc ttc ttg cca ccc act gag         1028
Pro Pro Asp Pro Ala Glu Pro Thr Ser Thr Phe Leu Pro Pro Thr Glu
            295                 300                 305 agc cgg atg tct gtc agc tcg gat cct gac cct gcc gct tac tct gta         1076
Ser Arg Met Ser Val Ser Ser Asp Pro Asp Pro Ala Ala Tyr Ser Val
            310                 315                 320 act gca ggg cga ccg cac cct tcc atc agt gaa gag gat gag ggc ttc         1124
Thr Ala Gly Arg Pro His Pro Ser Ile Ser Glu Glu Asp Glu Gly Phe
325                 330                 335 gac tgt ctg tca tcc cca gag caa gct gag cca cca ggt gga ggg tgg         1172
Asp Cys Leu Ser Ser Pro Glu Gln Ala Glu Pro Pro Gly Gly Gly Trp
340                 345                 350                 355 cgg gga agc ctc ggg gag cca cca ccg cct cca cgg gcc tca ctg agc         1220
Arg Gly Ser Leu Gly Glu Pro Pro Pro Pro Pro Arg Ala Ser Leu Ser
            360                 365                 370 tcg gac acc agc gca ctg tcc tac gac tct gtc aag tac aca ctg gtg         1268
Ser Asp Thr Ser Ala Leu Ser Tyr Asp Ser Val Lys Tyr Thr Leu Val
            375                 380                 385 gtg gat gag cat gcc cag ctt gag ttg gtg agc ctg cgg cca tgt ttt         1316
Val Asp Glu His Ala Gln Leu Glu Leu Val Ser Leu Arg Pro Cys Phe
            390                 395                 400 gga gat tac agt gac gaa agc gac tct gcc act gtc tat gac aac tgt         1364
Gly Asp Tyr Ser Asp Glu Ser Asp Ser Ala Thr Val Tyr Asp Asn Cys
405                 410                 415 gcc tct gcc tcc tcg ccc tac gag tca gcc att ggt gag gaa tat gag         1412
Ala Ser Ala Ser Ser Pro Tyr Glu Ser Ala Ile Gly Glu Glu Tyr Glu
420                 425                 430                 435 gag gcc cct caa ccc cgg cct ccc acc tgc ctg tca gag gac tcc aca         1460
Glu Ala Pro Gln Pro Arg Pro Pro Thr Cys Leu Ser Glu Asp Ser Thr
            440                 445                 450 ccg gat gag cct gac gtc cac ttc tct aag aag ttt ctg aat gtc ttc         1508
Pro Asp Glu Pro Asp Val His Phe Ser Lys Lys Phe Leu Asn Val Phe
            455                 460                 465
```

-continued

| | | |
|---|---|---|
| atg agt ggc cgc tct cgt tcc tcc agt gcc gag tcc ttt ggg ctg ttc<br>Met Ser Gly Arg Ser Arg Ser Ser Ser Ala Glu Ser Phe Gly Leu Phe<br>                  470                            475                            480 | 1556 | |
| tcc tgt gtc atc aat ggg gag gag cat gag caa acc cat cgg gct ata<br>Ser Cys Val Ile Asn Gly Glu Glu His Glu Gln Thr His Arg Ala Ile<br>485                               490                                495 | 1604 | |
| ttc agg ttt gtg cct cgg cat gaa gat gaa ctt gag ctg gaa gtg gac<br>Phe Arg Phe Val Pro Arg His Glu Asp Glu Leu Glu Leu Glu Val Asp<br>500                             505                           510                   515 | 1652 | |
| gac cct ctg ctg gtg gag ctg cag gca gaa gac tat tgg tat gag gcc<br>Asp Pro Leu Leu Val Glu Leu Gln Ala Glu Asp Tyr Trp Tyr Glu Ala<br>                  520                            525                            530 | 1700 | |
| tat aac atg cgc act gga gcc cgt ggt gtc ttt cct gcc tac tat gcc<br>Tyr Asn Met Arg Thr Gly Ala Arg Gly Val Phe Pro Ala Tyr Tyr Ala<br>                         535                            540                            545 | 1748 | |
| att gag gtc acc aag gag cct gag cac atg gca gcc ctt gcc aaa aac<br>Ile Glu Val Thr Lys Glu Pro Glu His Met Ala Ala Leu Ala Lys Asn<br>                  550                            555                            560 | 1796 | |
| agc gac tgg att gac cag ttc cgg gtg aag ttc ctg ggc tct gtc cag<br>Ser Asp Trp Ile Asp Gln Phe Arg Val Lys Phe Leu Gly Ser Val Gln<br>565                               570                           575 | 1844 | |
| gtt cct tat cac aag ggc aat gat gtc ctc tgt gct gct atg caa aag<br>Val Pro Tyr His Lys Gly Asn Asp Val Leu Cys Ala Ala Met Gln Lys<br>580                             585                          590                 595 | 1892 | |
| atc gcc acc acc cgc cgg ctc acc gtg cac ttt aac ccg ccc tcc agc<br>Ile Ala Thr Thr Arg Arg Leu Thr Val His Phe Asn Pro Pro Ser Ser<br>                  600                            605                            610 | 1940 | |
| tgt gtc ctt gaa atc agc gtt agg ggt gtc aag ata ggt gtc aaa gct<br>Cys Val Leu Glu Ile Ser Val Arg Gly Val Lys Ile Gly Val Lys Ala<br>                         615                            620                            625 | 1988 | |
| gat gaa gct cag gag gcc aag gga aat aaa tgt agc cac ttt ttc cag<br>Asp Glu Ala Gln Glu Ala Lys Gly Asn Lys Cys Ser His Phe Phe Gln<br>                  630                            635                            640 | 2036 | |
| cta aaa aac atc tct ttc tgt ggg tac cat cca aag aac aac aag tac<br>Leu Lys Asn Ile Ser Phe Cys Gly Tyr His Pro Lys Asn Asn Lys Tyr<br>645                               650                           655 | 2084 | |
| ttt ggg ttt atc act aag cac cct gct gac cac cgg ttt gcc tgc cat<br>Phe Gly Phe Ile Thr Lys His Pro Ala Asp His Arg Phe Ala Cys His<br>660                             665                          670                 675 | 2132 | |
| gtc ttt gtg tct gaa gat tcc acc aaa gcc ctg gca gag tct gtg ggg<br>Val Phe Val Ser Glu Asp Ser Thr Lys Ala Leu Ala Glu Ser Val Gly<br>                  680                            685                            690 | 2180 | |
| cgt gca ttt cag cag ttc tac aag caa ttt gtg gaa tat acc tgt cct<br>Arg Ala Phe Gln Gln Phe Tyr Lys Gln Phe Val Glu Tyr Thr Cys Pro<br>                       695                            700                           705 | 2228 | |
| aca gaa gat atc tac ttg gag tag cagcaacccc cctctctgca gcccctcagc<br>Thr Glu Asp Ile Tyr Leu Glu<br>                  710 | 2282 | |
| cccaggccag tactaggaca gctgactgct gacaggatgt tgtactgcca cgagagaatg | 2342 | |
| ggggagtgag ggctgttggg gtcgggggc aggggtttgg ggagaggcag atgcagttta | 2402 | |
| ttgtaatata tggggttaga ttaatctatg gaggacagta caggctctct cggggctggg | 2462 | |
| gaagggcagg gctggggtgg gggtcaggca tctggccaca aagggtccc ctagggacag | 2522 | |
| aggcgctgca ccatcctggg cttgtttcat actagaggcc ctggctttct ggctcttggg | 2582 | |
| tcctgccttg acaaagccca gccacctgga agtgtcacct tcccttgtcc acctcaccca | 2642 | |
| gtgccctgag ctcatgctga gcccaagcac ctccgaagga ctttccagta aggaaatggc | 2702 | |
| aacatgtgac agtgagaccc tgttctcatc tgtggggctc cggcagctcc gacccccagc | 2762 |

-continued

```
ctggccagca cgctgaccct ggcaagcttg tgtgttcaaa gaaggagagg gccacagcaa    2822
gccctgcctg ccagggaagg ttccctctca gctggcccca gccaactggt cactgtcttg    2882
tcacctggct actactatta aagtgccatt tcttgtctga aaaaaaaaaa aaaaaaaaa     2942 aaaaactcga g                                                         2953
```

<210> SEQ ID NO 103
<211> LENGTH: 714
<212> TYPE: PRT
<213> ORGANISM: Artificial
<220> FEATURE:
<223> OTHER INFORMATION: description of sequence: Protein encoded by
      Exon-Intron Boundary of the rIB1 Gene - Splice donor

<400> SEQUENCE: 103

```
Met Ala Arg Leu Ser Pro Gly Met Ala Glu Arg Glu Ser Gly Leu Ser
1               5                   10                  15

Gly Gly Ala Ala Ser Pro Pro Ala Ala Ser Pro Phe Leu Gly Leu His
            20                  25                  30

Ile Ala Ser Pro Pro Asn Phe Arg Leu Thr His Asp Ile Ser Leu Glu
        35                  40                  45

Glu Phe Glu Asp Glu Asp Leu Ser Glu Ile Thr Asp Glu Cys Gly Ile
    50                  55                  60

Ser Leu Gln Cys Lys Asp Thr Leu Ser Leu Arg Pro Pro Arg Ala Gly
65                  70                  75                  80

Leu Leu Ser Ala Gly Ser Ser Gly Ser Ala Gly Ser Arg Leu Gln Ala
                85                  90                  95

Glu Met Leu Gln Met Asp Leu Ile Asp Ala Ala Ser Asp Thr Pro Gly
            100                 105                 110

Ala Glu Asp Asp Glu Glu Asp Asp Glu Leu Ala Ala Gln Arg Pro
        115                 120                 125

Gly Val Gly Pro Ser Lys Ala Glu Ser Gly Gln Glu Pro Ala Ser Arg
    130                 135                 140

Ser Gln Gly Gln Gly Gln Gly Pro Gly Thr Gly Cys Gly Asp Thr Tyr
145                 150                 155                 160

Arg Pro Lys Arg Pro Thr Thr Leu Asn Leu Phe Pro Gln Val Pro Arg
                165                 170                 175

Ser Gln Asp Thr Leu Asn Asn Asn Ser Leu Gly Lys Lys His Ser Trp
            180                 185                 190

Gln Asp Arg Val Ser Arg Ser Ser Pro Leu Lys Thr Gly Glu Gln
        195                 200                 205

Thr Pro Pro His Glu His Ile Cys Leu Ser Asp Glu Leu Pro Pro Gln
    210                 215                 220

Gly Ser Pro Val Pro Thr Gln Asp Arg Gly Thr Ser Thr Asp Ser Pro
225                 230                 235                 240

Cys Arg Arg Thr Ala Ala Thr Gln Met Ala Pro Pro Ser Gly Pro Pro
                245                 250                 255

Ala Thr Ala Pro Gly Gly Arg Gly His Ser His Arg Asp Arg Ser Ile
            260                 265                 270

Ser Ala Asp Val Arg Leu Glu Ala Thr Glu Glu Ile Tyr Leu Thr Pro
        275                 280                 285

Val Gln Arg Pro Pro Asp Pro Ala Glu Pro Thr Ser Thr Phe Leu Pro
    290                 295                 300

Pro Thr Glu Ser Arg Met Ser Val Ser Ser Asp Pro Asp Pro Ala Ala
305                 310                 315                 320
```

Tyr Ser Val Thr Ala Gly Arg Pro His Pro Ser Ile Ser Glu Glu Asp
            325                 330                 335

Glu Gly Phe Asp Cys Leu Ser Ser Pro Glu Gln Ala Glu Pro Pro Gly
        340                 345                 350

Gly Gly Trp Arg Gly Ser Leu Gly Glu Pro Pro Pro Pro Arg Ala
    355                 360                 365

Ser Leu Ser Ser Asp Thr Ser Ala Leu Ser Tyr Asp Ser Val Lys Tyr
370                 375                 380

Thr Leu Val Val Asp Glu His Ala Gln Leu Glu Leu Val Ser Leu Arg
385                 390                 395                 400

Pro Cys Phe Gly Asp Tyr Ser Asp Glu Ser Asp Ser Ala Thr Val Tyr
            405                 410                 415

Asp Asn Cys Ala Ser Ala Ser Ser Pro Tyr Glu Ser Ala Ile Gly Glu
            420                 425                 430

Glu Tyr Glu Glu Ala Pro Gln Pro Arg Pro Pro Thr Cys Leu Ser Glu
        435                 440                 445

Asp Ser Thr Pro Asp Glu Pro Asp Val His Phe Ser Lys Lys Phe Leu
    450                 455                 460

Asn Val Phe Met Ser Gly Arg Ser Arg Ser Ser Ser Ala Glu Ser Phe
465                 470                 475                 480

Gly Leu Phe Ser Cys Val Ile Asn Gly Glu Glu His Glu Gln Thr His
            485                 490                 495

Arg Ala Ile Phe Arg Phe Val Pro Arg His Glu Asp Glu Leu Glu Leu
            500                 505                 510

Glu Val Asp Asp Pro Leu Leu Val Glu Leu Gln Ala Glu Asp Tyr Trp
        515                 520                 525

Tyr Glu Ala Tyr Asn Met Arg Thr Gly Ala Arg Gly Val Phe Pro Ala
    530                 535                 540

Tyr Tyr Ala Ile Glu Val Thr Lys Glu Pro Glu His Met Ala Ala Leu
545                 550                 555                 560

Ala Lys Asn Ser Asp Trp Ile Asp Gln Phe Arg Val Lys Phe Leu Gly
            565                 570                 575

Ser Val Gln Val Pro Tyr His Lys Gly Asn Asp Val Leu Cys Ala Ala
        580                 585                 590

Met Gln Lys Ile Ala Thr Thr Arg Arg Leu Thr Val His Phe Asn Pro
    595                 600                 605

Pro Ser Ser Cys Val Leu Glu Ile Ser Val Arg Gly Val Lys Ile Gly
610                 615                 620

Val Lys Ala Asp Glu Ala Gln Glu Ala Lys Gly Asn Lys Cys Ser His
625                 630                 635                 640

Phe Phe Gln Leu Lys Asn Ile Ser Phe Cys Gly Tyr His Pro Lys Asn
            645                 650                 655

Asn Lys Tyr Phe Gly Phe Ile Thr Lys His Pro Ala Asp His Arg Phe
            660                 665                 670

Ala Cys His Val Phe Val Ser Glu Asp Ser Thr Lys Ala Leu Ala Glu
        675                 680                 685

Ser Val Gly Arg Ala Phe Gln Gln Phe Tyr Lys Gln Phe Val Glu Tyr
    690                 695                 700

Thr Cys Pro Thr Glu Asp Ile Tyr Leu Glu
705                 710

<210> SEQ ID NO 104
<211> LENGTH: 711

```
<212> TYPE: PRT
<213> ORGANISM: Homo sapiens
<220> FEATURE:
<223> OTHER INFORMATION: description of sequence: human IB1 protein
      sequence

<400> SEQUENCE: 104
```

| | | | | | | | | | | | | | | | |
|---|---|---|---|---|---|---|---|---|---|---|---|---|---|---|---|
| Met | Ala | Glu | Arg | Glu | Ser | Gly | Gly | Leu | Gly | Gly | Ala | Ala | Ser | Pro | |
| 1 | | | | 5 | | | | | 10 | | | | | 15 | |
| Pro | Ala | Ala | Ser | Pro | Phe | Leu | Gly | Leu | His | Ile | Ala | Ser | Pro | Pro | Asn |
| | | | 20 | | | | | 25 | | | | | 30 | | |
| Phe | Arg | Leu | Thr | His | Asp | Ile | Ser | Leu | Glu | Glu | Phe | Glu | Asp | Glu | Asp |
| | | 35 | | | | | 40 | | | | | 45 | | | |
| Leu | Ser | Glu | Ile | Thr | Asp | Glu | Cys | Gly | Ile | Ser | Leu | Gln | Cys | Lys | Asp |
| 50 | | | | | 55 | | | | | 60 | | | | | |
| Thr | Leu | Ser | Leu | Arg | Pro | Pro | Arg | Ala | Gly | Leu | Leu | Ser | Ala | Gly | Gly |
| 65 | | | | | 70 | | | | | 75 | | | | | 80 |
| Gly | Gly | Ala | Gly | Ser | Arg | Leu | Gln | Ala | Glu | Met | Leu | Gln | Met | Asp | Leu |
| | | | | 85 | | | | | 90 | | | | | 95 | |
| Ile | Asp | Ala | Thr | Gly | Asp | Thr | Pro | Gly | Ala | Glu | Asp | Asp | Glu | Glu | Asp |
| | | | 100 | | | | | 105 | | | | | 110 | | |
| Asp | Asp | Glu | Glu | Arg | Ala | Ala | Arg | Pro | Gly | Ala | Gly | Pro | Pro | Lys | |
| | | 115 | | | | | 120 | | | | | 125 | | | |
| Ala | Glu | Ser | Gly | Gln | Glu | Pro | Ala | Ser | Arg | Gly | Gln | Gly | Gln | Ser | Gln |
| 130 | | | | | 135 | | | | | 140 | | | | | |
| Gly | Gln | Ser | Gln | Gly | Pro | Gly | Ser | Gly | Asp | Thr | Tyr | Arg | Pro | Lys | Arg |
| 145 | | | | | 150 | | | | | 155 | | | | | 160 |
| Pro | Thr | Thr | Leu | Asn | Leu | Phe | Pro | Gln | Val | Pro | Arg | Ser | Gln | Asp | Thr |
| | | | | 165 | | | | | 170 | | | | | 175 | |
| Leu | Asn | Asn | Asn | Ser | Leu | Gly | Lys | Lys | His | Ser | Trp | Gln | Asp | Arg | Val |
| | | | 180 | | | | | 185 | | | | | 190 | | |
| Ser | Arg | Ser | Ser | Ser | Pro | Leu | Lys | Thr | Gly | Glu | Gln | Thr | Pro | Pro | His |
| | | 195 | | | | | 200 | | | | | 205 | | | |
| Glu | His | Ile | Cys | Leu | Ser | Asp | Glu | Leu | Pro | Pro | Gln | Ser | Gly | Pro | Ala |
| 210 | | | | | 215 | | | | | 220 | | | | | |
| Pro | Thr | Thr | Asp | Arg | Gly | Thr | Ser | Thr | Asp | Ser | Pro | Cys | Arg | Arg | Ser |
| 225 | | | | | 230 | | | | | 235 | | | | | 240 |
| Thr | Ala | Thr | Gln | Met | Ala | Pro | Pro | Gly | Gly | Pro | Pro | Ala | Ala | Pro | Pro |
| | | | | 245 | | | | | 250 | | | | | 255 | |
| Gly | Gly | Arg | Gly | His | Ser | His | Arg | Asp | Arg | Ile | His | Tyr | Gln | Ala | Asp |
| | | | 260 | | | | | 265 | | | | | 270 | | |
| Val | Arg | Leu | Glu | Ala | Thr | Glu | Glu | Ile | Tyr | Leu | Thr | Pro | Val | Gln | Arg |
| | | 275 | | | | | 280 | | | | | 285 | | | |
| Pro | Pro | Asp | Ala | Ala | Glu | Pro | Thr | Ser | Ala | Phe | Leu | Pro | Pro | Thr | Glu |
| | | | | | 295 | | | | | 300 | | | | | |
| | | | 290 | | | | | | | | | | | | |
| Ser | Arg | Met | Ser | Val | Ser | Ser | Asp | Pro | Asp | Pro | Ala | Ala | Tyr | Pro | Ser |
| 305 | | | | | 310 | | | | | 315 | | | | | 320 |
| Thr | Ala | Gly | Arg | Pro | His | Pro | Ser | Ile | Ser | Glu | Glu | Glu | Glu | Gly | Phe |
| | | | | 325 | | | | | 330 | | | | | 335 | |
| Asp | Cys | Leu | Ser | Ser | Pro | Glu | Arg | Ala | Glu | Pro | Pro | Gly | Gly | Gly | Trp |
| | | | 340 | | | | | 345 | | | | | 350 | | |
| Arg | Gly | Ser | Leu | Gly | Glu | Pro | Pro | Pro | Pro | Arg | Ala | Ser | Leu | Ser | |
| | | 355 | | | | | 360 | | | | | 365 | | | |
| Ser | Asp | Thr | Ser | Ala | Leu | Ser | Tyr | Asp | Ser | Val | Lys | Tyr | Thr | Leu | Val |
| | | 370 | | | | | 375 | | | | | 380 | | | |

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
            405                 410                 415

Ala Ser Val Ser Ser Pro Tyr Glu Ser Ala Ile Gly Glu Glu Tyr Glu
            420                 425                 430

Glu Ala Pro Arg Pro Gln Pro Pro Ala Cys Leu Ser Glu Asp Ser Thr
            435                 440                 445

Pro Asp Glu Pro Asp Val His Phe Ser Lys Lys Phe Leu Asn Val Phe
450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
            485                 490                 495

Phe Arg Phe Val Pro Arg His Glu Asp Glu Leu Glu Leu Glu Val Asp
                500                 505                 510

Asp Pro Leu Leu Val Glu Leu Gln Ala Glu Asp Tyr Trp Tyr Glu Ala
            515                 520                 525

Tyr Asn Met Arg Thr Gly Ala Arg Gly Val Phe Pro Ala Tyr Tyr Ala
530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
595                 600                 605

Cys Val Leu Glu Ile Ser Val Arg Gly Val Lys Ile Gly Val Lys Ala
            610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
            675                 680                 685

Arg Ala Phe Gln Gln Phe Tyr Lys Gln Phe Val Glu Tyr Thr Cys Pro
            690                 695                 700

Thr Glu Asp Ile Tyr Leu Glu
705                 710

<210> SEQ ID NO 105
<211> LENGTH: 2136
<212> TYPE: DNA
<213> ORGANISM: Homo sapiens
<220> FEATURE:
<223> OTHER INFORMATION: description of sequence: nucleic acid sequence
      encoding human IB1 protein

<400> SEQUENCE: 105
atggcggagc gagaaagcgg cggcctggga ggggggccg cgtccccgcc cgccgcctcc      60
ccgttcctgg ggctgcacat cgcttcgcct cccaatttca ggctcaccca tgacatcagc     120

```
                                               -continued
ctggaggagt ttgaggatga agacctctcg gagatcactg atgagtgtgg catcagctta      180
cagtgcaaag acaccctgtc cttacggccc ccgcgcgccg ggctgctctc tgcgggcggc      240
ggcggcgcgg ggagccggtt gcaggccgag atgctgcaga tggacctgat cgacgcgacg      300
ggggacactc ccggggccga ggacgacgag gaggacgacg acgaggagcg cgcggcccgg      360
cggccgggag cggggccgcc caaggccgag tccggccagg agccggcgtc ccgcggccag      420
ggccagagcc aaggccagag ccagggcccg ggcagcgggg acacgtaccg gcccaagcgg      480
cccaccacgc tcaacctctt tccgcaggtg ccgcggtctc aggacacact gaataataat      540
tctctgggca aaaagcacag ttggcaggat cgggtgtctc gatcatcctc accctgaag      600 acagggagc agacaccacc gcatgaacac atctgcctga gcgatgagct gccccccccag      660 agcggccccg cccccaccac agatcgaggc acctccaccg acagcccttg ccgccgcagc      720
acagccaccc agatggcacc tccgggtggt cccctgctg ccccgcctgg gggtcggggc      780
cactcgcatc gagaccgaat ccactaccag gccgatgtgc gactagaggc cactgaggag      840
atctacctga ccccagtgca gaggccccca gacgctgcag agcccacctc cgccttcctg      900
ccgcccactg agagccggat gtcagtcagc tccgatccag accctgccgc ctacccctcc      960
acggcagggc ggccgcaccc ctccatcagt gaagaggaag agggcttcga ctgcctgtcg     1020
tccccagagc gggctgagcc ccaggcgga gggtggcggg ggagcctggg ggagccgccg     1080
ccacctccac gggcctctct gagctcggac accagcgccc tgtcctatga ctctgtcaag     1140
tacacgctgg tggtagatga gcatgcacag ctggagctgg tgagcctgcg gccgtgcttc     1200
ggagactaca gtgacgagag tgactctgcc accgtctatg acaactgtgc ctccgtctcc     1260
tcgccctatg agtcggccat cggagaggaa tatgaggagg ccccgcggcc ccagccccct     1320
gcctgcctct ccgaggactc cacgcctgat gaacccgacg tccatttctc caagaaattc     1380
ctgaacgtct tcatgagtgg ccgctcccgc tcctccagtg ctgagtcctt cgggctgttc     1440
tcctgcatca tcaacgggga ggagcaggag cagacccacc gggccatatt caggtttgtg     1500
cctcgacacg aagacgaact tgagctggaa gtggatgacc ctctgctagt ggagctccag     1560
gctgaagact actggtacga ggcctacaac atgcgcactg gtgcccgggg tgtctttcct     1620
gcctattacg ccatcgaggt caccaaggag cccgagcaca tggcagccct ggccaaaaac     1680
agtgactggg tggaccagtt ccgggtgaag ttcctgggct cagtccaggt tccctatcac     1740
aagggcaatg acgtcctctg tgctgctatg caaaagattg ccaccacccg ccggctcacc     1800
gtgcacttta acccgccctc cagctgtgtc ctggagatca gcgtgcgggg tgtgaagata     1860
ggcgtcaagg ccgatgactc ccaggaggcc aagggggaata aatgtagcca ctttttccag     1920
ttaaaaaaca tctctttctg cggatatcat ccaaagaaca acaagtactt tgggttcatc     1980
accaagcacc ccgccgacca ccggtttgcc tgccacgtct ttgtgtctga agactccacc     2040
aaagccctgg cagagtccgt ggggagagca ttccagcagt tctacaagca gtttgtggag     2100
tacacctgcc ccacagaaga tatctacctg gagtag                              2136
```